US012642472B2

(12) United States Patent
Ruppersberg et al.

(10) Patent No.: US 12,642,472 B2
(45) **Date of Patent: *Jun. 2, 2026**

(54) SYSTEMS, DEVICES, COMPONENTS AND METHODS FOR DETECTING THE LOCATIONS OF SOURCES OF CARDIAC RHYTHM DISORDERS IN A PATIENT'S HEART AND GENERATING AN ESTIMATE OR PROBABILITY OF THE PATIENT BEING FREE FROM ATRIAL FIBRILLATION

(71) Applicant: Boston Scientific Scimed, Inc., Maple Grove, MN (US)

(72) Inventors: Peter Ruppersberg, Blonay (CH); Philip Haeusser, Munich (DE); Melissa Huang Szu-Min Kong, West Lake Hills, TX (US); David Emanuel Luksic, Munich (DE); Kostiantyn Serhiyovich Ahapov, Munich (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 644 days.

This patent is subject to a terminal disclaimer.

(21) Appl. No.: 17/331,576

(22) Filed: May 26, 2021

(65) Prior Publication Data

US 2021/0282693 A1 Sep. 16, 2021

Related U.S. Application Data

(63) Continuation-in-part of application No. 16/387,873, filed on Apr. 18, 2019, now Pat. No. 11,291,395.
(Continued)

(51) Int. Cl.
*A61B 5/36* (2021.01)
*A61B 5/00* (2006.01)
(Continued)

(52) U.S. Cl.
CPC .............. *A61B 5/361* (2021.01); *A61B 5/343* (2021.01); *A61B 5/7275* (2013.01); *A61B 5/742* (2013.01)

(58) Field of Classification Search
CPC ................................ A61B 5/361; A61B 5/343
(Continued)

(56) References Cited

U.S. PATENT DOCUMENTS 930,236 A 8/1909 Schacht
987,217 A 3/1911 Connor et al.
(Continued)

FOREIGN PATENT DOCUMENTS

CN 111655130 A 9/2020
EP 2586363 A1 5/2013
(Continued)

OTHER PUBLICATIONS

Bellmann, Electrographic flow mapping—a novel technology for endocardial driver identification in patients . . . , 2017, Charite University Hospital, Berlin, Germany.
(Continued)

*Primary Examiner* — Nicole F Johnson
(74) *Attorney, Agent, or Firm* — Nelson Mullins Riley & Scarborough LLP

(57) ABSTRACT

Disclosed are various examples and embodiments of systems, devices, components and methods configured to detect the locations of sources of cardiac rhythm disorders in a patient's heart, and then to generate an estimate or probability of the patient being free from atrial fibrillation. The various embodiments employ at least one computing device to process a plurality of electrogram surfaces through time to generate at least one electrographical flow (EGF) map, representation, pattern, or data set, and then process the at least one EGF map, representation, pattern, or data set to
(Continued)

determine at least two of source activity levels, flow angle variability (FAV) levels, and active fractionation (AFR) levels corresponding thereto. On the basis of a combination of the determined at least two of source activity levels, FAV levels, and AFR levels, an electrographical volatility index (EVI) score or metric representative of the estimate or probability of the patient being free from AF is generated.

34 Claims, 61 Drawing Sheets
(49 of 61 Drawing Sheet(s) Filed in Color)

Related U.S. Application Data

(60) Provisional application No. 63/032,238, filed on May 29, 2020.

(51) Int. Cl.
 *A61B 5/343* (2021.01)
 *A61B 5/361* (2021.01)

(58) Field of Classification Search
 USPC ........................................................ 600/515
 See application file for complete search history.

(56) References Cited

U.S. PATENT DOCUMENTS

| | | | |
|---|---|---|---|
| 1,684,880 A | 9/1928 | Norton |
| 1,972,114 A | 9/1934 | Stephenson |
| 2,042,372 A | 5/1936 | Watson |
| 2,056,018 A | 9/1936 | Popp |
| 4,186,451 A | 2/1980 | Ruo |
| 4,622,702 A | 11/1986 | Allen |
| 4,745,641 A | 5/1988 | Tash |
| 5,172,699 A | 12/1992 | Svenson et al. |
| 5,239,708 A | 8/1993 | Irwin |
| 5,271,411 A | 12/1993 | Ripley et al. |
| 5,383,917 A | 1/1995 | Desai et al. |
| 5,427,112 A | 6/1995 | Noren et al. |
| 5,433,196 A | 7/1995 | Fiat |
| 5,433,198 A | 7/1995 | Desai |
| 5,450,846 A | 9/1995 | Goldreyer |
| 5,480,422 A | 1/1996 | Ben-Haim |
| 5,487,391 A | 1/1996 | Panescu |
| 5,549,108 A | 8/1996 | Edwards et al. |
| 5,582,173 A | 12/1996 | Li |
| 5,595,183 A | 1/1997 | Swanson et al. |
| 5,609,158 A | 3/1997 | Chan |
| 5,617,134 A | 4/1997 | Lamothe |
| 5,657,755 A | 8/1997 | Desai |
| 5,662,108 A | 9/1997 | Budd et al. |
| 5,687,737 A | 11/1997 | Branham et al. |
| 5,718,241 A | 2/1998 | Ben-Haim et al. |
| 5,752,518 A | 5/1998 | Mcgee et al. |
| 5,795,303 A | 8/1998 | Swanson et al. |
| 5,817,134 A | 10/1998 | Greenhut et al. |
| 5,840,025 A | 11/1998 | Ben-Haim |
| 5,848,972 A | 12/1998 | Triedman et al. |
| 5,868,680 A | 2/1999 | Steiner et al. |
| 5,954,665 A | 9/1999 | Ben-Haim |
| 6,052,618 A | 4/2000 | Dahlke et al. |
| 6,066,094 A | 5/2000 | Ben-Haim |
| 6,067,668 A | 5/2000 | Rudd |
| 6,115,628 A | 9/2000 | Stadler et al. |
| 6,188,924 B1 | 2/2001 | Swanson et al. |
| 6,236,883 B1 | 5/2001 | Ciaccio et al. |
| 6,256,540 B1 | 7/2001 | Panescu et al. |
| 6,301,496 B1 | 10/2001 | Reisfeld |
| 6,360,121 B1 | 3/2002 | Shoda et al. |
| 6,393,626 B1 | 5/2002 | Dhillon |
| 6,434,760 B1 | 8/2002 | Montalvo |
| 6,480,615 B1 | 11/2002 | Sun et al. |
| 6,480,815 B1 | 11/2002 | Olson et al. |
| 6,522,905 B2 | 2/2003 | Desai |
| 6,550,074 B1 | 4/2003 | Allenbaugh et al. |
| 6,584,345 B2 | 6/2003 | Govari |
| 6,684,417 B1 | 2/2004 | Schneider |
| 6,725,085 B2 | 4/2004 | Schwartzman et al. |
| 6,847,839 B2 | 1/2005 | Ciaccio et al. |
| 6,856,830 B2 | 2/2005 | He |
| 6,892,091 B1 | 5/2005 | Ben-Haim et al. |
| 6,920,350 B2 | 7/2005 | Xue et al. |
| 6,941,166 B2 | 9/2005 | Macadam et al. |
| 6,959,212 B2 | 10/2005 | Hsu et al. |
| 6,975,900 B2 | 12/2005 | Rudy et al. |
| 6,978,168 B2 | 12/2005 | Beatty et al. |
| 7,016,719 B2 | 3/2006 | Rudy et al. |
| 7,043,292 B2 | 5/2006 | Tarjan et al. |
| 7,081,114 B2 | 7/2006 | Rashidi |
| 7,117,030 B2 | 10/2006 | Berenfeld et al. |
| 7,123,954 B2 | 10/2006 | Narayan et al. |
| 7,206,630 B1 | 4/2007 | Tarler |
| 7,245,962 B2 | 7/2007 | Ciaccio et al. |
| 7,263,397 B2 | 8/2007 | Hauck et al. |
| 7,283,665 B2 | 10/2007 | Suzuki |
| 7,283,865 B2 | 10/2007 | Noren |
| 7,289,843 B2 | 10/2007 | Beatty et al. |
| 7,328,063 B2 | 2/2008 | Zhang et al. |
| 7,340,783 B2 | 3/2008 | Leaphart et al. |
| 7,505,810 B2 | 3/2009 | Harlev et al. |
| 7,515,954 B2 | 4/2009 | Harlev et al. |
| 7,736,785 B2 | 6/2010 | Oda et al. |
| 7,751,882 B1 | 7/2010 | Helland |
| 7,761,142 B2 | 7/2010 | Ghanem et al. |
| 7,761,150 B2 | 7/2010 | Ghanem et al. |
| 7,907,994 B2 | 3/2011 | Stolarski et al. |
| 7,930,018 B2 | 4/2011 | Harlev et al. |
| 7,930,020 B2 | 4/2011 | Zhang et al. |
| 8,048,063 B2 | 11/2011 | Aeby et al. |
| 8,150,502 B2 | 4/2012 | Kumar et al. |
| 8,160,682 B2 | 4/2012 | Kumar et al. |
| 8,165,666 B1 | 4/2012 | Briggs et al. |
| 8,165,671 B2 | 4/2012 | Freeman et al. |
| 8,175,702 B2 | 5/2012 | Efimov et al. |
| 8,244,335 B2 | 8/2012 | Kumar et al. |
| 8,521,266 B2 | 8/2013 | Narayan et al. |
| 8,538,503 B2 | 9/2013 | Kumar et al. |
| 8,560,046 B2 | 10/2013 | Kumar et al. |
| 8,594,777 B2 | 11/2013 | Briggs et al. |
| 8,639,325 B2 | 1/2014 | Efimov et al. |
| 8,647,284 B2 | 2/2014 | Afonso |
| 8,676,303 B2 | 3/2014 | Narayan |
| 8,700,140 B2 | 4/2014 | Narayan et al. |
| 8,838,222 B2 | 9/2014 | Narayan et al. |
| 8,838,223 B2 | 9/2014 | Narayan et al. |
| 8,852,130 B2 | 10/2014 | Govari |
| 8,868,169 B2 | 10/2014 | Narayan et al. |
| 8,911,917 B2 | 12/2014 | Sato et al. |
| 9,050,006 B2 | 6/2015 | Narayan et al. |
| 9,055,877 B2 | 6/2015 | Narayan et al. |
| 9,055,878 B2 | 6/2015 | Narayan et al. |
| 9,089,269 B2 | 7/2015 | Narayan et al. |
| 9,107,600 B2 | 8/2015 | Narayan et al. |
| 9,173,670 B2 | 11/2015 | Sepulveda et al. |
| 9,220,427 B2 | 12/2015 | Narayan et al. |
| 9,236,883 B2 | 1/2016 | Guha |
| 9,241,649 B2 | 1/2016 | Kumar et al. |
| 9,241,667 B2 | 1/2016 | Narayan et al. |
| 9,282,910 B2 | 3/2016 | Narayan et al. |
| 9,332,915 B2 | 5/2016 | Narayan et al. |
| 9,392,948 B2 | 7/2016 | Briggs et al. |
| 9,398,883 B2 | 7/2016 | Narayan et al. |
| 9,408,536 B2 | 8/2016 | Narayan et al. |
| 9,451,975 B2 | 9/2016 | Sepulveda et al. |
| 9,474,491 B2 | 10/2016 | Li et al. |
| 9,597,004 B2 | 3/2017 | Hughes et al. |
| 9,642,674 B2 | 5/2017 | Chmiel et al. |
| 9,730,603 B2 | 8/2017 | Laughner et al. |
| 9,808,171 B2 | 11/2017 | Balachandran et al. |
| 9,872,653 B2 | 1/2018 | Li et al. |
| 9,955,887 B2 | 5/2018 | Hughes et al. |

(56) References Cited

U.S. PATENT DOCUMENTS

| | | |
|---|---|---|
| 10,098,559 B2 | 10/2018 | Hughes et al. |
| 10,123,703 B2 | 11/2018 | Bardy et al. |
| 10,136,828 B2 | 11/2018 | Houben et al. |
| 10,143,374 B2 | 12/2018 | Ruppersberg |
| 10,201,277 B2 | 2/2019 | Ruppersberg |
| 10,221,551 B2 | 3/2019 | Gray |
| 10,271,754 B2 | 4/2019 | Bahney et al. |
| 10,299,691 B2 | 5/2019 | Hughes et al. |
| D852,965 S | 7/2019 | Bahney et al. |
| 10,362,952 B2 | 7/2019 | Basu et al. |
| 10,362,953 B2 | 7/2019 | Basu |
| 10,517,500 B2 | 12/2019 | Kumar et al. |
| 10,772,522 B2 | 9/2020 | Zadig |
| 10,806,343 B2 | 10/2020 | Ruppersberg |
| 10,820,800 B2 | 11/2020 | Ruppersberg |
| 10,888,236 B2 | 1/2021 | Ruppersberg |
| 10,980,418 B2 | 4/2021 | Ruppersberg |
| 11,291,395 B2 | 4/2022 | Ruppersberg |
| 11,389,102 B2 | 7/2022 | Haeusser et al. |
| 2001/0037522 A1 | 11/2001 | Pool et al. |
| 2001/0056245 A1 | 12/2001 | Mlynash et al. |
| 2002/0010392 A1 | 1/2002 | Desai |
| 2002/0016548 A1 | 2/2002 | Stadler et al. |
| 2002/0151808 A1 | 10/2002 | Schwartzman et al. |
| 2003/0079278 A1 | 5/2003 | Tash |
| 2003/0236466 A1 | 12/2003 | Tarjan et al. |
| 2004/0073262 A1 | 4/2004 | Lovett |
| 2004/0133113 A1 | 7/2004 | Krishnan |
| 2004/0243011 A1 | 12/2004 | Plaza |
| 2005/0148892 A1 | 7/2005 | Desai |
| 2005/0182336 A1 | 8/2005 | Sippens Groenewegen |
| 2005/0203502 A1 | 9/2005 | Boveja et al. |
| 2006/0084870 A1 | 4/2006 | Kim et al. |
| 2006/0084970 A1 | 4/2006 | Beatty et al. |
| 2006/0093891 A1 | 5/2006 | Issacci et al. |
| 2006/0111700 A1 | 5/2006 | Kunis et al. |
| 2006/0161069 A1 | 7/2006 | Li |
| 2006/0161206 A1 | 7/2006 | Efimov et al. |
| 2007/0055167 A1 | 3/2007 | Bullinga |
| 2007/0073179 A1 | 3/2007 | Afonso et al. |
| 2007/0208260 A1 | 9/2007 | Afonso |
| 2007/0219454 A1 | 9/2007 | Guzzetta et al. |
| 2007/0299351 A1 | 12/2007 | Harlev et al. |
| 2008/0009758 A1 | 1/2008 | Voth |
| 2008/0051704 A1 | 2/2008 | Patel et al. |
| 2008/0097539 A1 | 4/2008 | Belalcazar |
| 2008/0109041 A1 | 5/2008 | De Voir |
| 2008/0114258 A1 | 5/2008 | Zhang et al. |
| 2008/0161669 A1 | 7/2008 | Hauck et al. |
| 2008/0193308 A1 | 8/2008 | Korcoban |
| 2008/0245955 A1 | 10/2008 | Tachi et al. |
| 2008/0275367 A1 | 11/2008 | Barbagli et al. |
| 2009/0069704 A1 | 3/2009 | Macadam et al. |
| 2009/0099468 A1 | 4/2009 | Thiagalingam et al. |
| 2009/0112106 A1 | 4/2009 | Zhang |
| 2009/0112110 A1 | 4/2009 | Zhang |
| 2009/0112199 A1 | 4/2009 | Zhang et al. |
| 2009/0171274 A1 | 7/2009 | Harlev et al. |
| 2009/0177071 A1 | 7/2009 | Harlev et al. |
| 2009/0177072 A1 | 7/2009 | Harlev et al. |
| 2009/0177095 A1 | 7/2009 | Aeby et al. |
| 2009/0275828 A1 | 11/2009 | Shachar et al. |
| 2009/0299424 A1 | 12/2009 | Narayan |
| 2010/0000357 A1 | 1/2010 | Gutmann et al. |
| 2010/0030063 A1 | 2/2010 | Lee et al. |
| 2010/0035122 A1 | 2/2010 | Yamamoto et al. |
| 2010/0058519 A1 | 3/2010 | Davenport |
| 2010/0094274 A1 | 4/2010 | Narayan et al. |
| 2010/0129694 A1 | 5/2010 | Sugiura et al. |
| 2010/0204592 A1 | 8/2010 | Hatib et al. |
| 2010/0217143 A1 | 8/2010 | Whittington et al. |
| 2010/0249627 A1 | 9/2010 | Zhang et al. |
| 2010/0280402 A1 | 11/2010 | Dunbar et al. |
| 2010/0298729 A1 | 11/2010 | Zhang et al. |
| 2010/0305456 A1 | 12/2010 | Brainard, II |
| 2011/0087121 A1 | 4/2011 | Zhang et al. |
| 2011/0112425 A1 | 5/2011 | Muhlsteff et al. |
| 2011/0130801 A1 | 6/2011 | Maskara et al. |
| 2011/0196249 A1 | 8/2011 | Staeuber et al. |
| 2011/0213231 A1 | 9/2011 | Hall et al. |
| 2011/0219526 A1 | 9/2011 | Keegan |
| 2011/0251505 A1 | 10/2011 | Narayan et al. |
| 2011/0257547 A1 | 10/2011 | Zhang |
| 2011/0270046 A1 | 11/2011 | Paul et al. |
| 2011/0282227 A1 | 11/2011 | Zhang |
| 2012/0009502 A1 | 1/2012 | Darling et al. |
| 2012/0011643 A1 | 1/2012 | Schultz |
| 2012/0129071 A1 | 5/2012 | Sato et al. |
| 2012/0129073 A1 | 5/2012 | Spencer et al. |
| 2012/0232417 A1 | 9/2012 | Zhang |
| 2012/0233757 A1 | 9/2012 | Slot |
| 2012/0238889 A1 | 9/2012 | Yu et al. |
| 2012/0247519 A1 | 10/2012 | Dondurur et al. |
| 2012/0271135 A1 | 10/2012 | Burke et al. |
| 2012/0283590 A1* | 11/2012 | Afonso ............... A61B 5/339 |
| | | 600/523 |
| 2012/0321987 A1 | 12/2012 | Goto et al. |
| 2013/0006131 A1 | 1/2013 | Narayan et al. |
| 2013/0102868 A1 | 4/2013 | Fandrey et al. |
| 2013/0150740 A1 | 6/2013 | Narayan et al. |
| 2013/0150742 A1 | 6/2013 | Briggs et al. |
| 2013/0204142 A1 | 8/2013 | Bertholds et al. |
| 2013/0220032 A1 | 8/2013 | Packirisamy et al. |
| 2013/0226016 A1 | 8/2013 | Narayan et al. |
| 2013/0245476 A1 | 9/2013 | Takizawa et al. |
| 2013/0331718 A1 | 12/2013 | Narayan et al. |
| 2013/0337359 A1 | 12/2013 | Sugiura et al. |
| 2014/0066787 A1 | 3/2014 | Narayan et al. |
| 2014/0073981 A1 | 3/2014 | Narayan et al. |
| 2014/0088395 A1 | 3/2014 | Dubois et al. |
| 2014/0114204 A1 | 4/2014 | Narayan et al. |
| 2014/0209797 A1 | 7/2014 | Klimovitch |
| 2014/0228696 A1 | 8/2014 | Narayan et al. |
| 2014/0276152 A1 | 9/2014 | Narayan et al. |
| 2014/0343388 A1 | 11/2014 | Thakur et al. |
| 2014/0364848 A1 | 12/2014 | Heimbecher et al. |
| 2015/0057522 A1 | 2/2015 | Nguyen et al. |
| 2015/0065836 A1 | 3/2015 | Thakur et al. |
| 2015/0073246 A1 | 3/2015 | Chmiel et al. |
| 2015/0104729 A1 | 4/2015 | Ishida et al. |
| 2015/0105645 A1 | 4/2015 | Subramaniam et al. |
| 2015/0126840 A1* | 5/2015 | Thakur ............... A61B 5/287 |
| | | 606/41 |
| 2015/0126993 A1 | 5/2015 | Gelbart et al. |
| 2015/0164349 A1 | 6/2015 | Gopalakrishnan et al. |
| 2015/0208937 A1 | 7/2015 | Bullinga |
| 2015/0216438 A1 | 8/2015 | Bokan et al. |
| 2015/0250424 A1 | 9/2015 | Govari et al. |
| 2015/0254419 A1 | 9/2015 | Laughner et al. |
| 2015/0273541 A1 | 10/2015 | Kim |
| 2015/0289781 A1 | 10/2015 | Grunwald et al. |
| 2015/0313491 A1 | 11/2015 | Edwards et al. |
| 2015/0350502 A1 | 12/2015 | Lin |
| 2016/0000357 A1 | 1/2016 | Harlev et al. |
| 2016/0073960 A1 | 3/2016 | Jung et al. |
| 2016/0184028 A1 | 6/2016 | Warner et al. |
| 2016/0374582 A1 | 12/2016 | Wu et al. |
| 2017/0018205 A1 | 1/2017 | Santhanam et al. |
| 2017/0022694 A1 | 1/2017 | Broten |
| 2017/0027465 A1 | 2/2017 | Blauer et al. |
| 2017/0035497 A1 | 2/2017 | Nagale et al. |
| 2017/0065198 A1 | 3/2017 | Ruppersberg |
| 2017/0164858 A1 | 6/2017 | Basu |
| 2017/0178403 A1 | 6/2017 | Krummen et al. |
| 2017/0202471 A1 | 7/2017 | Urman et al. |
| 2017/0202515 A1 | 7/2017 | Zrihem et al. |
| 2017/0202521 A1 | 7/2017 | Urman et al. |
| 2017/0303807 A1 | 10/2017 | Laughner et al. |
| 2018/0342072 A1 | 11/2018 | Raudins |
| 2019/0125186 A1 | 5/2019 | Ruppersberg |
| 2019/0142271 A1 | 5/2019 | Ruppersberg |
| 2019/0284757 A1 | 9/2019 | Chopra et al. |
| 2019/0329302 A1 | 10/2019 | Wu |
| 2019/0357793 A1 | 11/2019 | Ruppersberg |

(56) References Cited

U.S. PATENT DOCUMENTS

| 2020/0024839 A1 | 1/2020 | Tapper |
| 2020/0046245 A1 | 2/2020 | Qu et al. |
| 2020/0240127 A1 | 7/2020 | Tash |
| 2020/0245885 A1 | 8/2020 | Haeusser et al. |
| 2020/0345261 A1 | 11/2020 | Haeusser et al. |
| 2021/0000369 A1 | 1/2021 | Luksic et al. |
| 2021/0068694 A1 | 3/2021 | Chou et al. |
| 2021/0259765 A1 | 8/2021 | Narayan |
| 2021/0393187 A1 | 12/2021 | Amos et al. |
| 2022/0245885 A1 | 8/2022 | Pags et al. |
| 2022/0345261 A1 | 10/2022 | Ali et al. |
| 2022/0387099 A1 | 12/2022 | Cohen et al. |
| 2024/0033008 A1 | 2/2024 | Govari et al. |

FOREIGN PATENT DOCUMENTS

| EP | 2638852 A1 | 9/2013 | |
| EP | 2641557 A1 | 9/2013 | |
| EP | 3192445 A1 | 7/2017 | |
| EP | 3346914 A1 | 7/2018 | |
| EP | 3346915 A1 | 7/2018 | |
| EP | 3375365 A2 | 9/2018 | |
| EP | 3192438 B1 | 8/2019 | |
| EP | 3 556 284 A2 | 10/2019 | |
| EP | 3686899 A1 | 7/2020 | |
| EP | 3747356 A1 | 12/2020 | |
| EP | 21176633.2 | 11/2021 | |
| EP | 3984457 A1 | 4/2022 | |
| EP | 4029449 A1 | 7/2022 | |
| EP | 4098198 A2 | 12/2022 | |
| EP | 4119054 A1 | 1/2023 | |
| EP | 4248859 A1 | 9/2023 | |
| ES | 2706537 A1 | 3/2019 | |
| JP | 63-270026 A | 11/1988 | |
| JP | 2012-164467 A | 8/2012 | |
| WO | 01/67950 A1 | 9/2001 | |
| WO | 2012/092016 A1 | 7/2012 | |
| WO | 2012/173697 A1 | 12/2012 | |
| WO | WO-2013106559 A2 * | 7/2013 | ......... A61B 5/04014 |
| WO | 2014/007871 A1 | 1/2014 | |
| WO | 2014/124231 A1 | 8/2014 | |
| WO | 2014/168987 A1 | 10/2014 | |
| WO | 2015/000870 A1 | 1/2015 | |
| WO | 2015/001097 A1 | 1/2015 | |
| WO | 2015/066678 A2 | 5/2015 | |
| WO | 2015/113770 A1 | 8/2015 | |
| WO | 2015/120961 A1 | 8/2015 | |
| WO | 2015/130824 A1 | 9/2015 | |
| WO | 2016/077786 A1 | 5/2016 | |
| WO | 2017/041892 A1 | 3/2017 | |
| WO | 2017/042623 A1 | 3/2017 | |
| WO | 2017/125114 A1 | 7/2017 | |
| WO | 2019/063861 A1 | 4/2019 | |

OTHER PUBLICATIONS

Bellmann, Indentification of active atrial fibrillation sources and their discrimination from passive rotors . . . , Clinical Research in Cardiology, 2018, 107: 1021-1032.

Kalifa, Mechanisms of wave fractionation at boundaries of high frequency excitation in the posterior left atrium of the Isolated Sheep . . . , Circulation 2006; 113:626-33.

Sohal, "Is Mapping of Complex Fractionated Electrograms Obsolete," Arrhythm. Electrophysiol. Rev. Aug. 2015; 4(2): 109-115.

Atienza et al., "Mechanisms of Fractionated Electrograms Formation in the Posterior Left Atrium During Paroxysmal . . . ," J Am Coll Cardiol. Mar. 1, 2011; 57(9): 1081-1092.

Correa de Sa et al., "Electrogram Fractionation—The Relationship between Spatiotemporal Variation of Tissue . . . ," Circ. Arrhythm. Electrophysiol. Dec. 2011; 4(6): 909-16.

Cantwell, C.D., "Techniques for automated local activation time annotation & conduction velocity estimation in cardiac mapping," Com. Bio. Med. 65 (2015) 229-242, Elsevier, NL.

"An Iterative Image Registration Technique with an Application to Stereo Vision," Bruce D. Lucas, Takeo Kanade, Proceedings of Imaging Understanding Workshop, pp. 121-130(1).

"Chaste: An Open Source C++ Library for Computational Physiology and Biology," Gary R. Mirams, et al. PLOS Computational Biology, Mar. 14, 2013, vol. 9, Issue3, e1002970.

"Horn-Schunck Optical Flow with a Multi-scale Strategy," Enric Meinhardt-Llopis et al., Image Processing On Line, 3 (2013), pp. 151-172.

"Impact of Rotor Ablation in Nonparoxysmal Atrial Fibrillation Patients," Sanghamitra Mohanty, et al., J. of the American College of Cardiology, vol. 68, No. 3, 2016.

"Interpolation with Splines in Tension: A Green's Function Approach," Paul Wessel and David Bercovici, Mathematical Geology, 77-93, vol. 30, No. 1, 1998.

"Lucas/Kanada Meets Horn/Schunck: Combining Local and Global Optic Flow Methods," Andres Bruhh, Joachim Waickert, Christoph Schnorr, International Journal of Computer Vision.

"Moving Surface Spline Interpolation Based on Green's Function," Xingsheng Deng and Zhong-an Tang, Math, Geosci (2011). 43:663-680.

"Novel Sirategy for Improved Substrate Mapping of the Atria Omnipolar Catheter and Signal Processing Technology Assesses Electrogram Signals Along Physiologic and Anatomic Directions," Deno et al., Circulation; Nov. 10, 2015, vol. 132, Issue Suppl. 3.

"Prospectively Quantifying the Propensity for Atrial Fibrillation: A Mechanistic Formulation," Carrick et al. ; Mar. 13, 2015, PLOS One, DOI:10.1371 journal.pone.0118746.

"Segmental Boundary Profile of Myocardial Motion to Localize Cardiac Abnormalities," Slamet Riyadi et al, Proceedings of the World Congress on Engineering 2010, vol. 1.

"SimpleFlow: A Non-Iterative, Sublinear Optical Flow Algorithm," Michael Tao et al. Eurographics 2012, vol. 31 (2012), No. 2.

Bellmann et at . Identif of active atrial fibr. srcs and their discrim from passive rotors using electro. flow map. Clinical Research in Cardiology, 107(11}:1021-1032, 2018.

Bellmann, "Velocity characteristics of atrial fibrillation sources determined by electrographic flow mapping before and after catheter ablation," Int'l Journal of Card., Feb. 2019, vol. 286, pp. 56-60, Elsevier, NL.

Bellmann, B., Electrographic Flow Mapping—A New Technology for Identification of Atrial Fibrillation Drivers; Jun. 1, 2017; P239; vol. 19; pp. iiiS4-iii55.Europace; Oxford, UK.

Cabral et al, "Imaging vector fields using line integral convolution," Technical report, Lawrence Livermore National Lab., CA (United States), 1993.

Catmull et al, "A class of local interpolating splines," Computer Aided Geometric Design, 317-326. Elsevier, 1974.

Correll et al, 2006, "SwisTrack: A Tracking Tool for Multi-Unit Robotic and Biological Systems," IEEE International Conference on Intelligent Robots and Systems. 2185-2191.

Eugene K. Lee et al., Machine learning plus optical flow a simple and sensitive method to detect cardioactive drugs, Nature, vol. 5, Jul. 3, 2015, pp. 1-12.

Ferrer ET, "Detailed Anatomical and Electrophysiological Models of Human Atria and Torso for the Simulation of Atrial Activation" PLOS One, Nov. 2, 2015.

Gall et al, "Functional Categorization of Objects using Real-time Markerless Motion Capture," IEEE Conf. on Computer Vision and Pattern Recognition (CVPR''11), 1969-1976, 2011.

Golemati et al., "Ultrasound-Image-Based Cardiovascular Tissue Motion Estimation," in IEEE Reviews in Biomedical Engineering, vol. 9, pp. 208-218, 2016.

He et al, "Video Target Tracking Based on Adaptive Kalman Filtering, Communications, Signal Processing, and Systems," CSPS 2019. Lecture Notes, vol. 571, Springer, Singapore.

Horn, et al., "Determining Optical Flow," Artificial Intelligence, vol. 17, pp. 185-204, 1981.

Hummel et al., "Atrial mapping with basket catheters—A Basket case?," JACC: Clinical Electrophysiology, vol. 2 Issue 1, Feb. 2016, pp. 66-68. (Hummel et al., continued) published by Elsevier in the Netherlands.

(56)                    References Cited

OTHER PUBLICATIONS

Kirchhof et al, "2016 ESC guidelines for the management of atrial fibrillation developed in collaboration with EACTS," European Heart Journal, vol. 37, Issue 38 2016.

Laughner et al., "Practical Considerations of Mapping Persistent Atrial Fibrillation With Whole-Chamber Basket Catheters," JACC: Clinical Electrophysiology, vol. 2, Issue 1, Feb. 2016, pp. 55-65. Published by Hindawi in Egypt.

Liu et al, 2018, "Visual tracking in high-dimensional particle filter," PLOS One 13 (8): e0201872, Aug. 23, 2018.

Lochmatter et al, "SwisTrack—A Flexible Open Source Tracking Software for Multi-Agent Systems," 2008 IEEE/RSJ Int'l Conf. Intell. Robots and Systems, France 2008, pp. 4004-4010.

Mcewan et al, "Efficient computational noise in GLSL," Journal of Graphics Tools, 16(2}:85-94, 2012.

Miroslav Dura et al , "Toward panoramic in situ mapping of action potential propagation in transgenic hearts to investigate initiation and therapeutic control of arrhythmias," Frontiers in Physiology, vol. 5, Sep. 8, 2014 pp. 1-7.

Murali et al., "Cardiac Ambulatory Monitoring. New Wireless Device Validated Against Conventional Holter Monitoring in a Case Series," Front. Cardiovasc. Med., Nov. 30, 2020, vol. 7, Lausanne, Switzerland.

Oesterlein et al, "Basket-Type Catheters: Diagnostic Pitfalls Caused by Deformation and Limited Coverage," BioMed Research International, vol. 2016 Article ID 5340574, published by Elsevier in the Netherlands.

Potse, "Scalable and Accurate ECG Simulation for Reaction-Diffusion Models of the Human Heart," Apr. 20, 2018, 1-14, vol. 9, Art. 370, Frontiers in Physiology, Switzerland.

Rios-Munoz, "Real-time rotational activity detection in atrial fibrillation," Frontiers in Physiology, Mar. 2018, vol. 9, pp. 1-17, Frontiers Media SA, CH.

Rios-Munoz., "Rotor Detection in Atrial Fibrillation," Doctoral Thesis. Universidad Carios III de Madrid. Jun. 2018 159 pages.

Rodrigo, et al, "Body surface localization of left and right atrial high-frequency rotors in atrial fibrillation patients: A clinical-computational study," Heart Rhythm, Sep. 2014.

Smith et al, "Interactive Computer-Assisted Tracking of Speckle Trajectories in Fluorescence Microscopy: Application to Actin Polymerization and Membrane Fusion," Biophysical Journal. 2011. 101. 1794-804. 10.1016/j.bpj.2011.09.007.

Strintzis et al., "Maximum likelihood motion estimation in ultrasound image sequences," in IEEE Signal Processing Letters, vol. 4, No. 6, pp. 156-157, Jun. 1997.

Tinevez et al, "TrackMate: An Open and Extensible Platform for Single-Particle Tracking," Methods. 2016. 115. 10.1016/j.ymeth. 2016.09.016.

Vassilis Georgiadis et al, "Multielec: A MATLAB Based Application for MEA Data Analysis," PLOS One, Jun. 15, 2015, pp. 1-17.

Zhu et al, "Real-Time Motion Capture: An Overview," Complex Intelligent and Software Intensive Systems (CISIS) 2016 10th International Conference on, pp. 522-525, 2016.

Extended European Search Report and Search Opinion received for European Application No. 25204955.6, mailed on Mar. 12, 2026, 7 pages.

* cited by examiner

200

NORMALIZE/ADJUST AMPLITUDES, FILTER ELECTROGRAM SIGNALS — 210

GENERATE 2D REPRESENTATION/MAP/GRID OF ELECTRODE POSITIONS — 230

GENERATE 3D ELECTROGRAM SURFACES FOR EACH TIME SLICE — 240

GENERATE A VELOCITY VECTOR MAP FROM THE TIME SLICE 3D ELECTROGRAM SURFACES — 250

IDENTIFY LOCATION AND SOURCE OF CARDIAC RHYTHM DISORDER — 260

MITRAL VALVE IMPACT

40

43

ROTOR: ARROW
DIRECTION SHOWS IF
ROTOR IS PASSIVE

FIBROTIC AREAS

BREAKTHROUGH
POINT

ABLAMAP IMAGE
SINGLE ACTIVE ROTOR
(64 ELECTRODES)

ablamap® Mapping System

***Ablamap®* First Electrographic Flow Mapping System**

Novel system for the identification of AF sources and therapy guidance based on Ablacon's proprietary Electrographic Flow (EGF®) algorithm technology

- Sub-electrode spatial resolution
- Patient classification based on long-term stability maps of AF sources
- Distinction of active and passive Rotors, Drivers and Triggers
- Continuous quantitative therapy monitoring during ablation
- Multi-Core Workstation

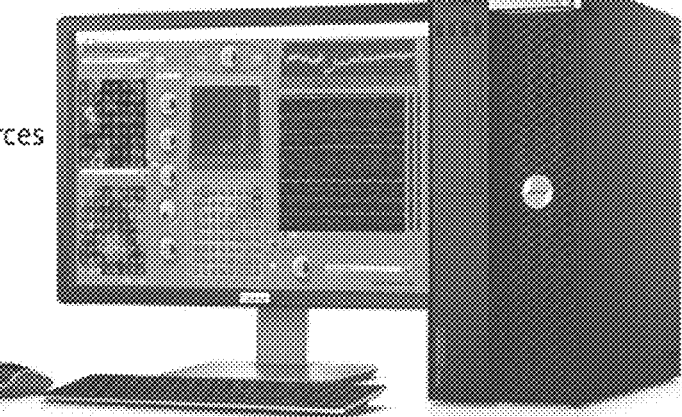

Fig. 15

- Basket catheter
- Standard Boston Scientific (Bard) LABSYSTEM PRO™ with Navigation and 3D Visualization (Biosense Webster, St. Jude)
- ablamap® Mapping Workstation (OEM made by Dell)

Fig. 17

EGF: Velocity Vectors Calculated as Optical Flow

Unipolar action potential travel on the atrial surface. They superimpose and interfere like image elements.

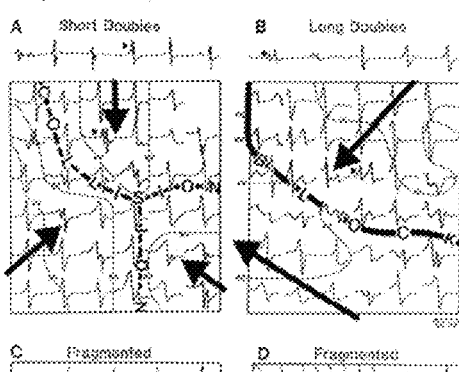

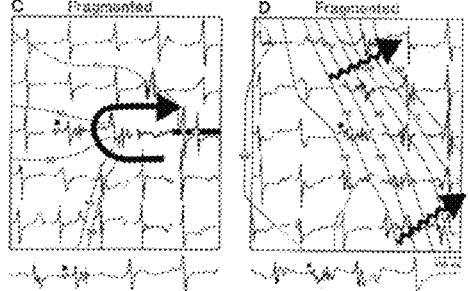

If the movement is small the spatial gradient of *I* is equal to the temporal derivative for each point of the action potential wave $$(1)\ \partial I/\partial u + \partial I/\partial v = -\partial I/\partial t$$

Equation (1) could be used to find the vector components u and v according to Horn and Schunck, 1981, by minimizing:

$$(2)\ \mathcal{E}_c = \iint (I_x u + I_y v - I_t)^2\ dx\,dy$$

If there is another constraint, where we accordingly use a minimization of the Smoothness Error:

$$(3)\ \mathcal{E}_s = \iint \{(u_x^2 + u_y^2) + (v_x^2 + v_y^2)\}\ dx\,dy$$

Minimisation is achieved by an iterative process according to Horn and Schunck, 1981, using a fixed scheme of five iterations.

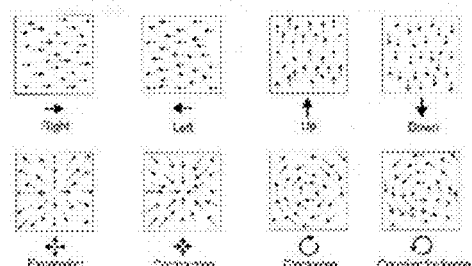

From: Configuration of Unipolar Atrial Electrograms During Electrically Induced Atrial Fibrillation in Humans. Karen T.S. Konings, Joep L.R.M. Smeets, Olaf C. Penn, Hein J.J. Wellens, Maurits A. Allessie https://... Circulation. 1997;95:1231-1241

How to Determine Electrographic Flow

• To determine the set of flow vectors that morph one electrographic voltage profile into the next.

• Infinite number of solutions!

• Best morph at minimal total vector amplitude.

• Learning from 1.9 s of samples: minimize deviation from previous result.

The Ablamap EGF Solution Validated in Sheep Heart

Optical mapping of
action potentials with
fluorescent dye

Simulation of basket
catheter data

EGF Analysis with
Ablamap

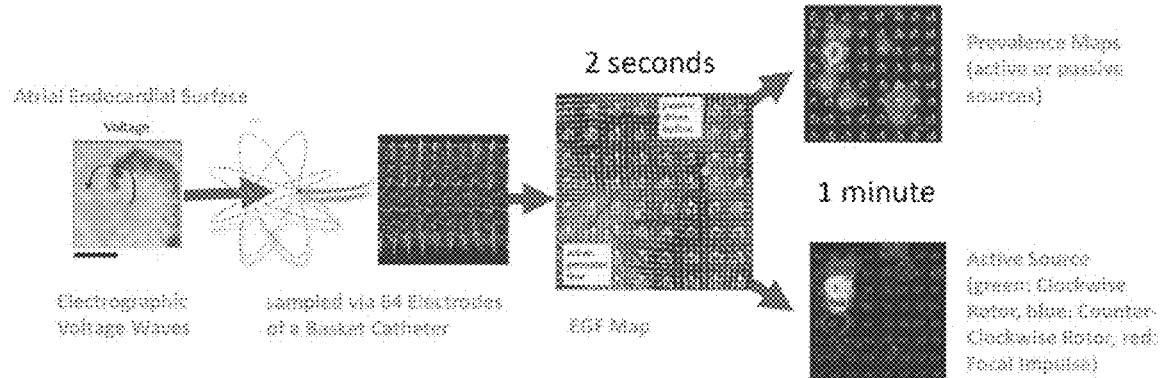

- 2 seconds of electrogram data yield a single EGF Map
- Each EGF Map is automatically analyzed with respect to active Sources of EGF, Source characteristics (Rotor, Focal Impulse) and passive Rotors.
- 1 minute of EGF Maps (i.e. 29 maps) yield one Prevalence map
- Prevalence Maps are statistical summaries of EGF behavior during one minute.
- Different types of AF sources can be identified, RF-ablated and ablation outcome directly confirmed.

Fig. 20

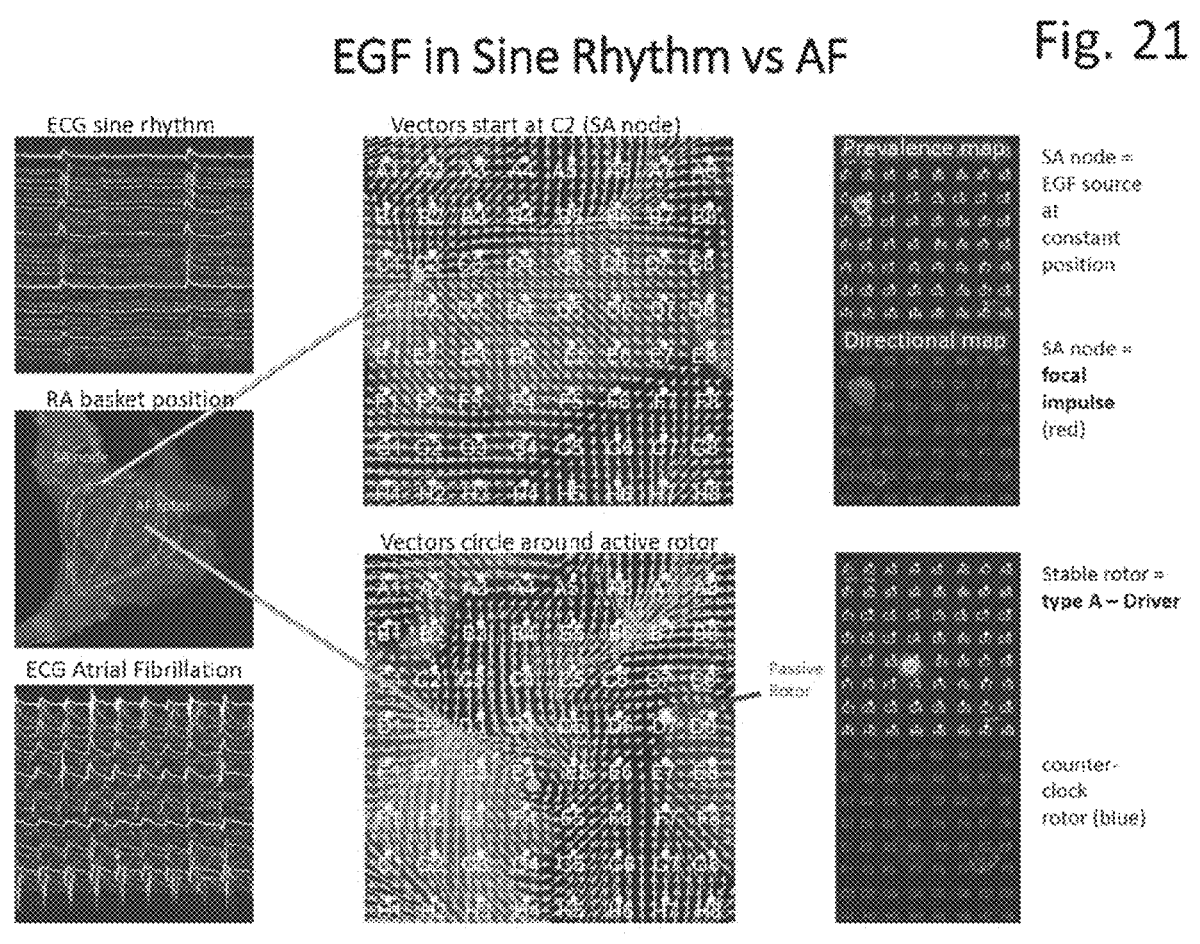

EGF in Sine Rhythm vs AF     Fig. 21

Discrimination between Active and Passive Rotors
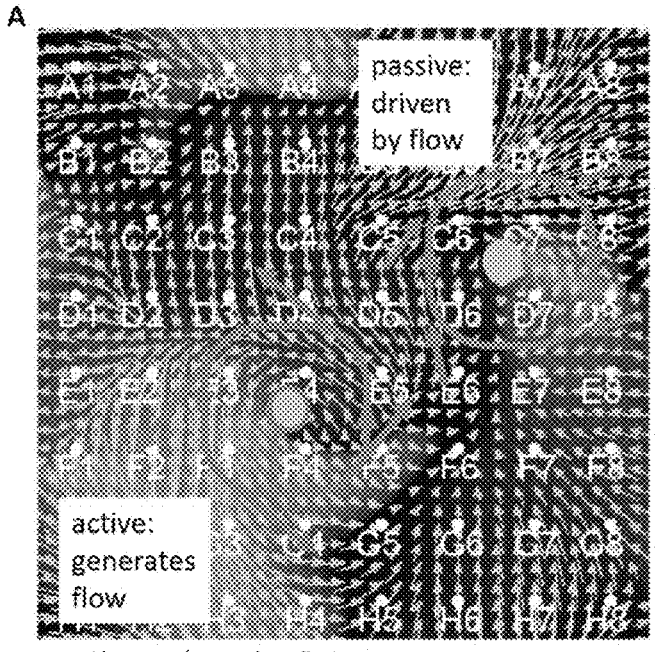
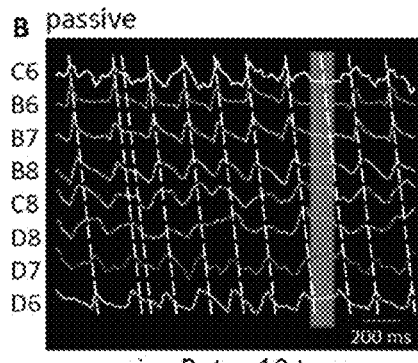
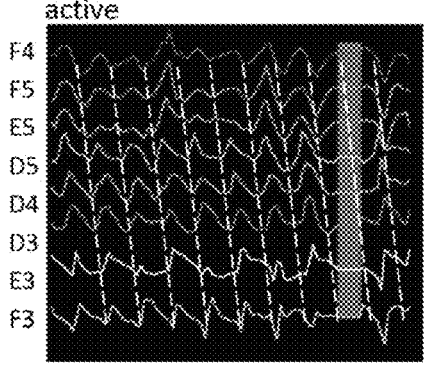
Fig. 22

Passive Rotors driven by Focal Impulse

FIRM vs EGF Comparison    Fig. 24

In 25 persistent AF patients treated with FIRM we found with EGF-Mapping:

|  | FIRM Rotors | Active EGF Sources | EGF Passive | EGF not Identified |
|---|---|---|---|---|
| RA | 15 | 5 | 9 | 1 |
| LA | 29 | 19 | 7 | 3 |
| Total | 44 | 24 | 16 | 4 |

Long term EFG monitoring during RF-Ablation shows successful removal of sources of excitation Patient Classification ( A, B and C )
by "Leading Source EGF Stability"

Prognostic Relevance (Body Surface)

• Nearly half of treated patients had recurrence of AF

• In retrospective EGF mapping using Ablamap:
Some had stable (present >50% of the time) A-type sources (drivers),
Most had On/Off switching B-type sources (triggers),
Some had only instable* chaotic C-type sources.

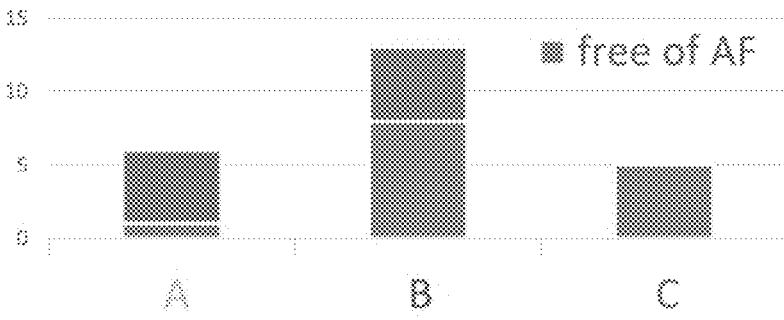

Correlation between the
type of sources and the
outcome was significant
(p value = 0.027)

Fig. 27

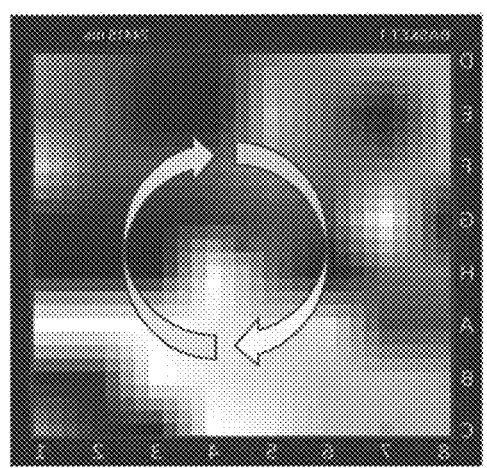
FIRM: One Rotor at GH45
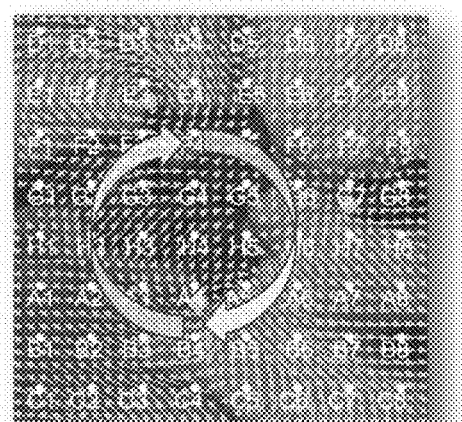
Ablamap: EGF B-type, two sources detected at E3 and A4
(together causing the rotation detected by FIRM)
Fig. 28

B-type patient : therapy guided by Ablamap

Prediction of Outcome During Procedure

In patients treated with FIRM:

Source was eliminated in some no stable Source was present in some

Source was missed in half (incorrect target)

Outcome:

AF-free

Strong and significant correlation between stable sources present/absent after ablation and outcome Recurrence

Electrographic Volatility Index – EVI Based on Three Mechanisms of AF

1.  Low Activity of Sources (Focal Impulse and Rotational Sources, A- and B-type)
2.  High Flow Angle Variability of Electrographic Flow Patterns (D-type)
3.  Lack of Active Fractionations (Colocalization of Fractionation and Action Potential Origins, E-type)

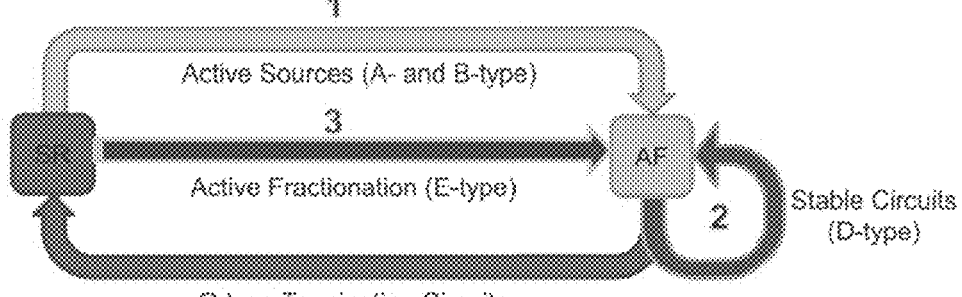

$$EVI = (1 - p\,(source))^{\alpha} \cdot p(variability)^{\beta} \cdot (1 - p\,(active\_fractionation))^{\gamma}$$

Fig. 31

EGF Visualized Patterns of Cardiac Action Potential Flow Correspond to Distinct AF Mechanisms 1) Sources that drive or trigger AF
   → manifests as an AF source in Ablamap (A- and/or B-type)

2) Stable reentry patterns (stable flow fields and/or "passive" rotational phenomena)
   → manifests as very low flow angle variability (FAV) area and perpetuates AF circuits (D-type)

3) Highly fractionated areas that emanate action potentials (AFR)
   → detected by a combination of active fractionation and action potential flow origins (E-type)

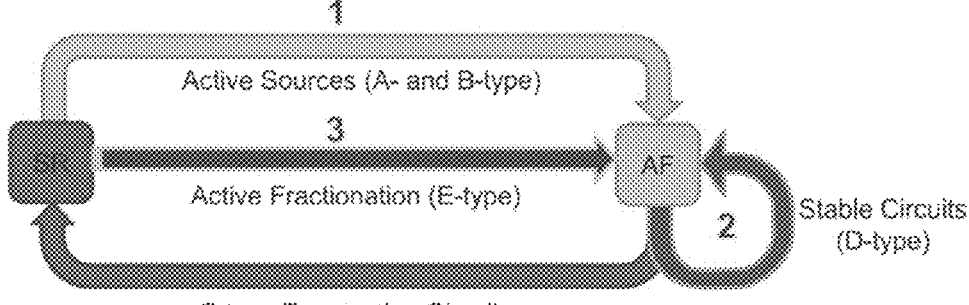

Fig. 34

EGF Source Activity Alone Cannot Provide a Complete Picture of a Patient's AF Status

- Active PV-type, A-type, B-type sources matter and can be targeted and eliminated

- 25 patients each point in sliding average

- Activity $R^2 = 0.58$

- Binary Prediction Correctness 70%

EGF Flow Angle Variability Alone Cannot Predict Freedom from AF

- Stable D-type circuits can be simulated and form a circuitry that we can understand and quantitatively analyze

- 25 patients each point in sliding average

- FAV Correlation $R^2$ = 0.43

- Binary Prediction Correctness 63%

Act and FAV: Development and Validation Cohorts

1. Development Cohort: Training Population patients 25 sliding average sorted according to:
ProbAF-free = Prob1^(weightA) * Prob2^(weightB)
Optimization for linear relationship between Score and ProbAF-free
Result Slope 0.9, R²=0.88, WeightA = 2.4, WeightB = 0.89

2. Internal Validation Cohort: Test Population patients sorted according to:
ProbAF-free = Prob1^(weightA) * Prob2^(weightB)
Calculated with formula fitted to Development Cohort
Result Slope 0.8, R²=0.88 same corrCoeff as Development Cohort

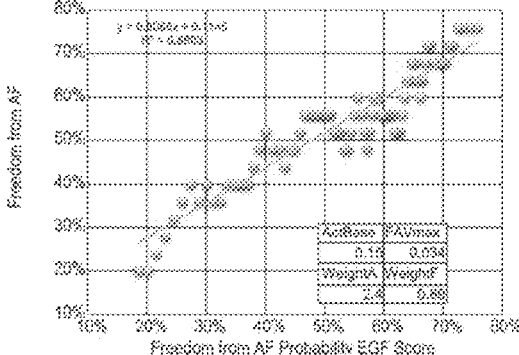

Fig. 38

Further Improving Prediction: Adding Active Fractionation Parameter

- E-type highly fractionated areas that emanate action potentials can be detected by a combination of fractionation and action potential origins (Active Fractionation)

- No significant source activity in standard EGF map but co-localization between:

- Active Fractionation Score above 0.8 and

- High Action Potential Flow Origin Density

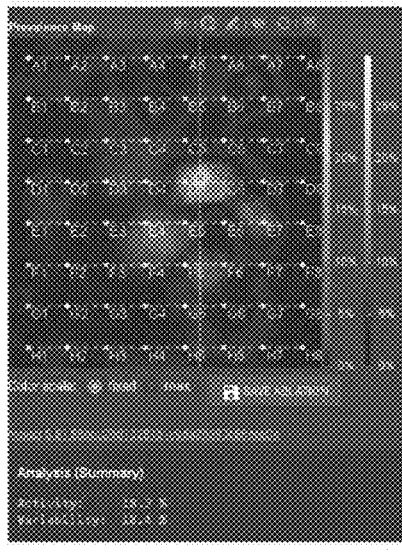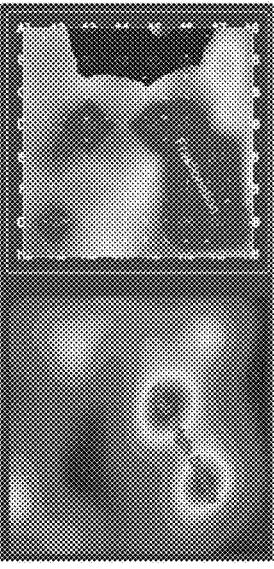

Fig. 39

Electrographic Volatility Index: Development and Validation Cohorts
1. Training Fit: Least square fit of EVI vs.
Outcome (% AF-free).
Plot: Sliding average over 25 patients, R² from linear
fit vs. sliding average
2. Validation: Fit result parameters from development
cohort applied to internal test cohort.
Result: Even better correlation R² = 0.9371 (no
overfitting)
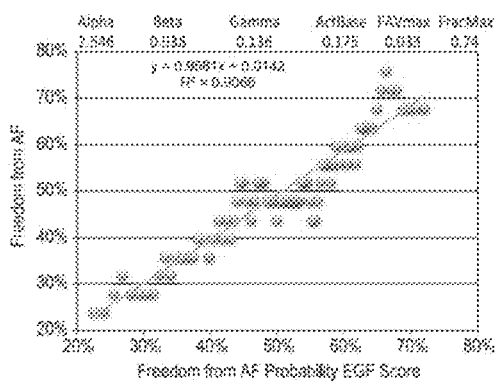 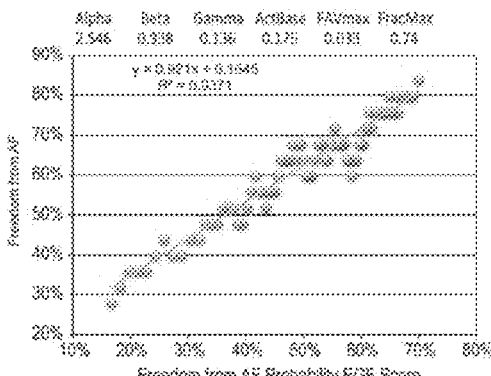
Fig. 40

EGF-Score of All Patients Combining Training and Test Populations

EGF-Identified Sources Matter: Retrospective Data Analysis

- Ablation of sources above threshold resulted in incremental improvement in 12-month freedom from AF compared with all-comers or those patients without any sources above threshold

- If a source above threshold was NOT ablated, chance of recurrence was very high

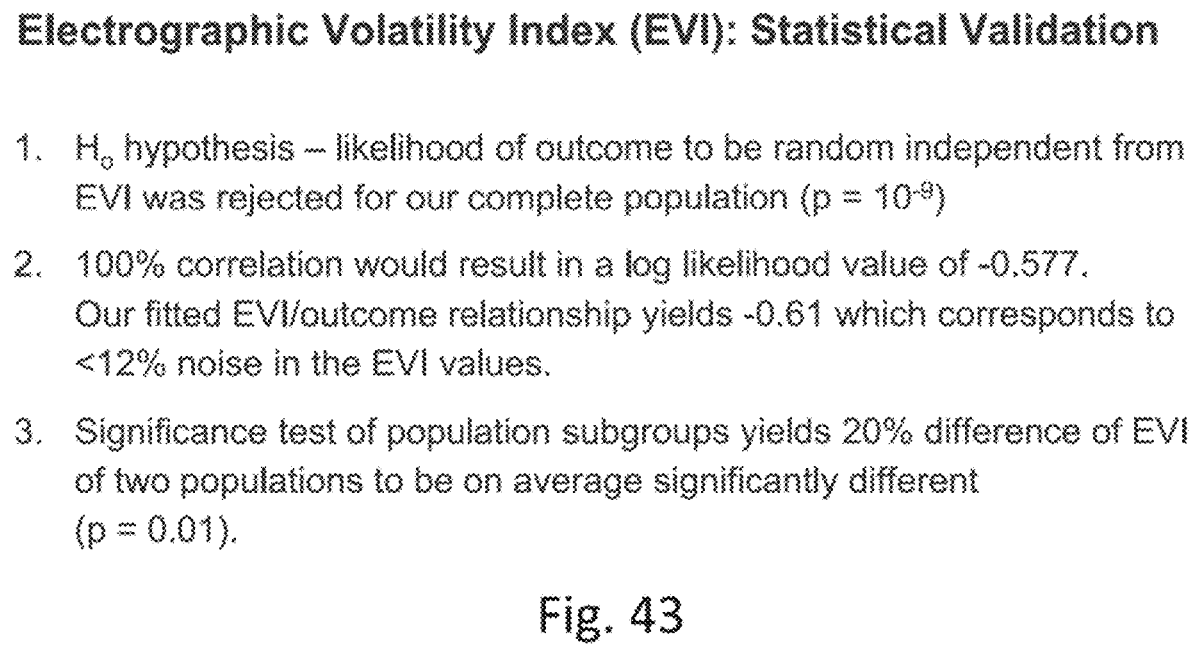

Electrographic Volatility Index (EVI): Statistical Validation

1. $H_0$ hypothesis – likelihood of outcome to be random independent from EVI was rejected for our complete population ($p = 10^{-9}$)

2. 100% correlation would result in a log likelihood value of -0.577. Our fitted EVI/outcome relationship yields -0.61 which corresponds to <12% noise in the EVI values.

3. Significance test of population subgroups yields 20% difference of EVI of two populations to be on average significantly different ($p = 0.01$).

Fig. 43

EGF Score: Comparison of Re-Do Patients with Persistent Patients
1. Re-do population: 92% Correlation;
   Slope 1.1; Range from 30% to 75%
2. De novo persistent AF population: 92% Correlation;
   Slope 1.0; Range from 15% to 85%
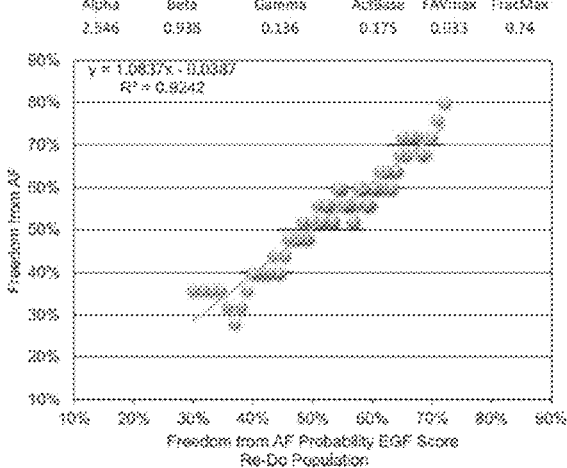
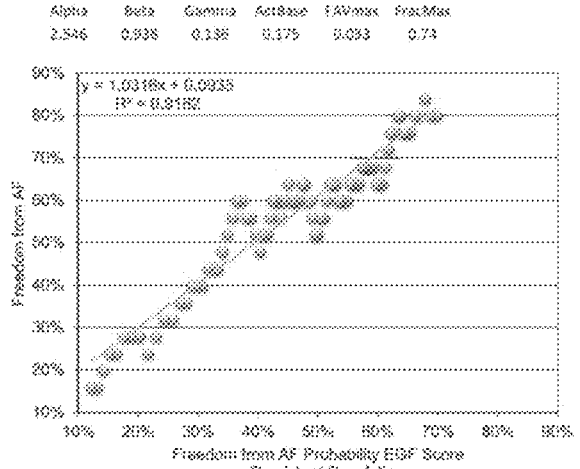
Fig. 44

EGF Score: Comparison of Re-Do Patients with Persistent Patients

1. Re-do population: All three scores contribute

2. De novo persistent AF population. Source Activity and Flow Stability score dominate. Active Fractionation Score shows inverse correlation with outcome

EGF Score: Comparison of Re-Do Patients with Persistent Patients
1. Re-do population: Source Activity score shows no strong correlation with outcome
2. De novo persistent AF population: Source Activity score shows very strong correlation at intermediate probabilities
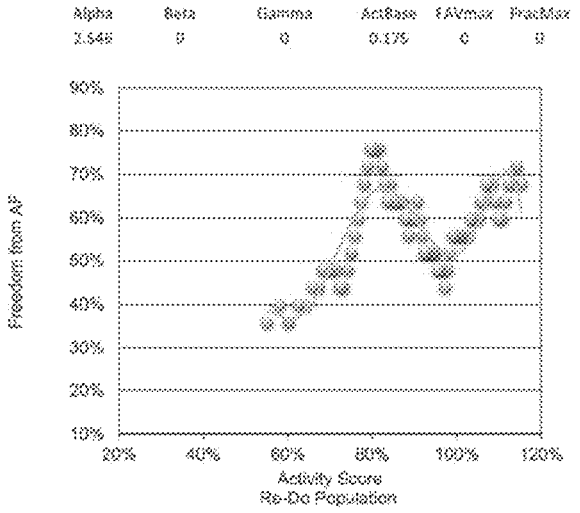
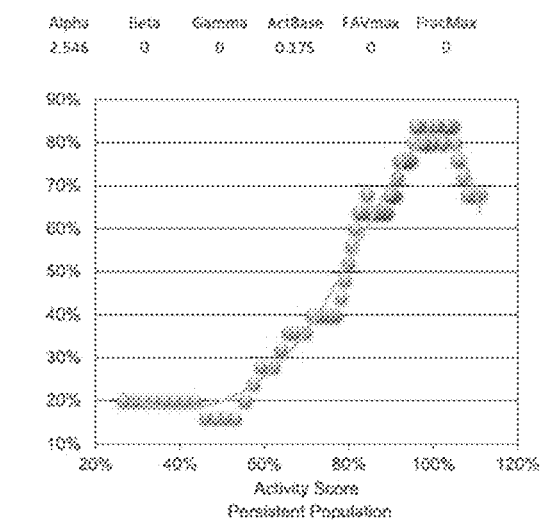
Fig. 46

EGF Score: Comparison of Re-Do Patients with Persistent Patients
1. Re-do population: Flow Angle Variability Score (D-type) shows significant correlation with outcome
2. De novo persistent AF population: Flow Angle Variability Score (D-type) shows no clear correlation with outcome
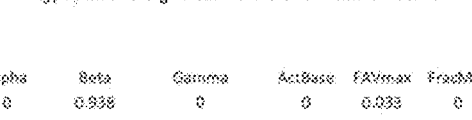
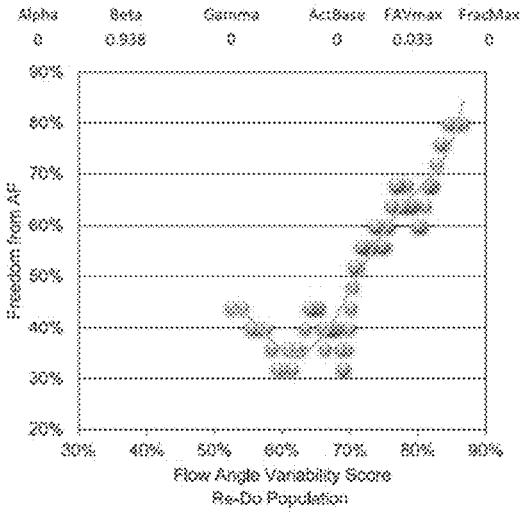
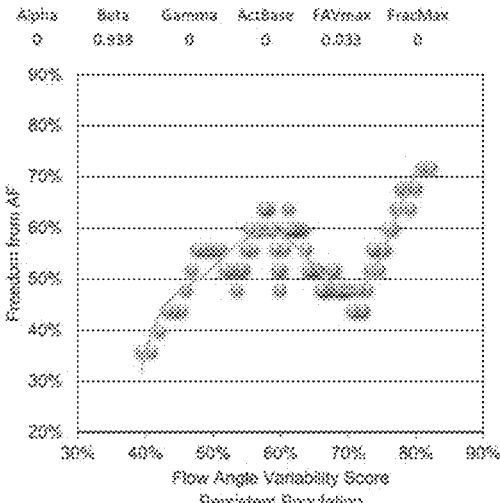
Fig. 48

EGF Score: Comparison of Re-Do Patients with Persistent Patients

Conclusions:

1.  The EGF Score can judge a wide spectrum of AF patients, based on its three components.

2.  De novo persistent AF patients are dominated by the existence of focal or rotational sources (A- and B-type). Stable circuits maintaining AF play an inferior role and Active Fractionation is only a small component of the activity.

3.  In Re-Do AF patients, in contrast, active sources play only a minor role. AF recurrence depends on stable circuits maintaining AF, and on active fractionation.

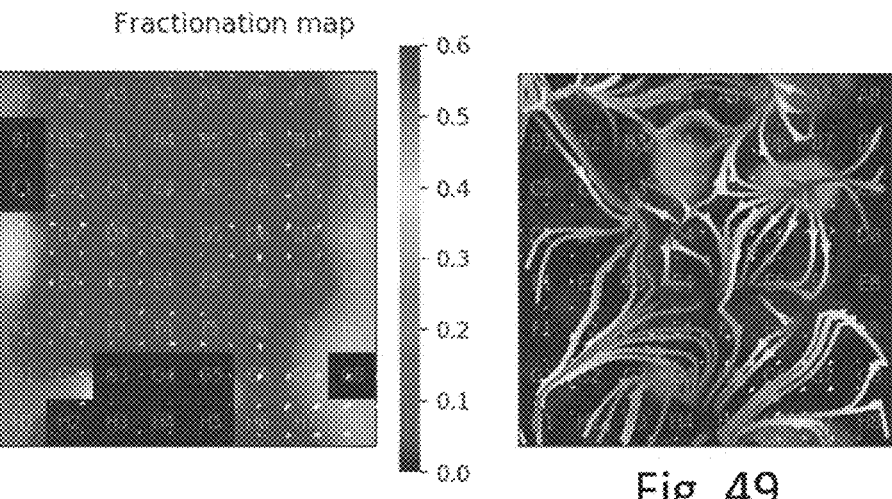

Fractionation map

Fig. 49

SYSTEMS, DEVICES, COMPONENTS AND METHODS FOR DETECTING THE LOCATIONS OF SOURCES OF CARDIAC RHYTHM DISORDERS IN A PATIENT'S HEART AND GENERATING AN ESTIMATE OR PROBABILITY OF THE PATIENT BEING FREE FROM ATRIAL FIBRILLATION

RELATED APPLICATIONS

This application claims priority and other benefits from U.S. Provisional Patent Application Ser. No. 63/032,238 to Ruppersberg et al. filed on May 29, 2020, which is entitled "Systems, Devices, Components and Methods for Detecting the Locations of Sources of Cardiac Rhythm Disorders in a Patient's Heart and Classifying Same, Including with the Use of Electrographic Volatility Indices and/or Active Fractionation" (hereafter "the '238 patent application").

This application is also a continuation-in-part of, and claims priority and other benefits from, U.S. patent application Ser. No. 16/387,873 to Ruppersberg filed on Apr. 18, 2019, which is entitled "Systems, Devices, Components and Methods for Detecting the Locations of Sources of Cardiac Rhythm Disorders in a Patient's Heart and Classifying Same" (hereafter "the '873 patent application").

The '238 and '873 patent applications are hereby incorporated by reference herein, each in its respective entirety Also incorporated by reference herein are any patent applications, documents or publications incorporated by reference into any of the patents or patent applications to which this patent application claims priority or other benefits above, and/or through the '873 patent application.

FIELD OF THE INVENTION

Various embodiments described and disclosed herein relate to the field of medicine generally, and more particularly to diagnosing and treating cardiac rhythm disorders in a patient's heart using electrophysiological mapping techniques, as well as in some embodiments using imaging, navigation, cardiac ablation and other types of medical systems, devices, components, and methods. Various embodiments described and disclosed herein also relate to systems, devices, components and methods for discovering with enhanced precision the location(s) and classifications of the source(s) of different types of cardiac rhythm disorders and irregularities in a patient's heart, such as, by way of example, active rotors, passive rotors, areas of fibrosis, breakthrough points and focus points.

BACKGROUND

Persistent atrial fibrillation (AF) is assumed to be caused by structural changes in atrial tissue, which can manifest themselves as multiwavelet re-entry and/or stable rotor mechanisms (see, e.g., De Groot M S et al., "Electropathological Substrate of Longstanding Persistent Atrial Fibrillation in Patients with Structural Heart Disease Epicardial Breakthrough," Circulation, 2010, 3: 1674-1682). Radio frequency (RF) ablation targeting such host drivers of AF is generally accepted as the best therapeutic approach. RF ablation success rates in treating AF cases are currently limited, however, by a lack of diagnostic tools that are capable of precisely determining the source (or type), and location, of such AF drivers. Better diagnostic tools would help reduce the frequency and extent of cardiac ablation procedures to the minimum amount required to treat AF, and would help balance the benefits of decreased fibrillatory burden against the morbidity of increased lesion load.

One method currently employed to localize AF drivers is the TOPERA® RhythmView® system, which employs a basket catheter having 64 electrodes arranged in an 8×8 pattern from which the system records unipolar electrograms or electrogram signals (EGMs). The RhythmViewQ® algorithm creates a propagation map of the 64 electrodes through a phase analysis of EGM peaks after improving the signal to noise ratio through filtering and subtraction of a simulated compound ECG artifact. The RhythmView® algorithm detects where peak sequences between electrodes show a circular pattern candidate for a re-entry cycle and indicates those locations in a Focal Impulse and Rotor Map (FIRM) using A1 to H8 chess field coordinates for the electrodes. The resolution of the TOPERA system is limited by the spacing of the electrodes and consequently does not show the details of the AF drivers. In particular, the TOPERA system cannot show if a circular EGM wavefront is actively generated by a re-entry mechanism and is therefore is a driver of AF (i.e., an active rotor), or whether a circular EGM wavefront simply represents turbulence passively generated by an EGM wavefront hitting a barrier (i.e., a passive rotor). In addition, the TOPERA system does not show the direction of AF wavefront propagation, and does not provide the spatial or temporal resolution required to detect singularities associated with the generation of an active rotor.

A recent independent multicenter study ("OASIS, Impact of Rotor Ablation in Non-Paroxysmal AF Patients: Results from a Randomized Trial," Sanghamitra Mohanty, et al. and Andrea Natale, J Am Coll Cardiol. 2016) reported that the results obtained using TOPERA FIRM technology were inferior to those provided by non-specific ablation of the posterior wall of the left atrium. Moreover, the results suggested that FIRM based ablation is not sufficient for therapeutic success without pulmonary vein isolation (PVI) being performed in parallel. Although there are some questions about the methodology of this trial, many experts are convinced that the resolution and interpretability of the TOPERA system need to be improved.

In another approach to the problem, Toronto scientists recently presented a strategy to analyze EGM wave propagation using "Omnipolar Mapping," which seeks to measure beat-by-beat conduction velocity and direction (see, e.g., "Novel Strategy for Improved Substrate Mapping of the Atria: Omnipolar Catheter and Signal Processing Technology Assesses Electrogram Signals Along Physiologic and Anatomic Directions," D. Curtis Deno et al. and Kumaraswamy Nanthakumar; Circulation. 2015; 132-A19778). This approach starts with the time derivative of a unipolar EGM as measured by a set of electrodes having known distances to one other. Assuming constant velocity, the velocity and direction representing the best fit for a spatial derivative of the measured EGM are calculated and used to represent an estimate of the E field. According to a communication by Dr. Nanthakumar at the 2016 CardioStim Convention in Nice, France, however, this method remains incapable of dealing successfully with complex data sets, such as those obtained during an episode of AF.

What is needed are improved means and methods of acquiring and processing intracardiac electrogram signals that reliably and accurately yield the precise locations and sources of cardiac rhythm disorders in a patient's heart. Doing so would enable cardiac ablation procedures to be carried out with greater locational precision, and would result in higher rates of success in treating cardiac rhythm disorders such as AF.

SUMMARY

In some embodiments, there are provided systems configured to generate an estimate or probability of a patient being free from atrial fibrillation (AF), the systems comprising at least one computing device comprising at least one non-transitory computer readable medium configured to store instructions executable by at least one processor to determine the source and location of the atrial fibrillation in the patient's heart, the computing device being operably connected to a display or monitor, the computing device being configured to: (a) receive electrogram signals; (b) assign positions of the electrodes on a mapping electrode assembly employed to acquire the electrogram signals to their corresponding electrogram signals; (c) provide or generate a map, representation, or data set of the electrode positions; (d) process the electrogram signals to generate a plurality of electrogram surfaces corresponding at least partially to the map, representation, or data set; (e) process the plurality of electrogram surfaces through time to generate at least one electrographical flow (EGF) map, representation, pattern, or data set; (f) process the at least one EGF map, representation, pattern, or data set to determine at least two of source activity levels, flow angle variability (FAV) levels, and active fractionation (AFR) levels corresponding thereto; (g) determine and generate, on the basis of a combination of the determined at least two of source activity levels, FAV levels, and AFR levels, an electrographical volatility index (EVI) representative of the estimate or probability of the patient being free from AF, wherein at least one of the EVI and the estimate or probability of the patient being free from AF is presented on a display, monitor, or printer to a user.

In some embodiments, such systems can further comprise any one or more of: (a) the computing device being configured to convolve at least two of the determined source activity levels, the determined flow angle variability levels, and the determined active fractionation levels with one another to provide the estimate or probability of the patient being free from AF; (b) the determined source activity levels corresponding to at least one of Type A atrial behavior exhibiting stable rotors and drivers and Type B atrial behavior where rotors switch on and off; (c) the determined flow angle variability levels corresponding to Type D atrial behavior exhibiting stable reentry patterns with low FAV; (d) the determined active fractionation levels corresponding to Type E atrial behavior exhibiting a combination of active fractionation and action potential flow origins; (e) the activity level corresponding to a percentage of time a detected source is determined to be on or active; (f) when the percentage of time the detected source is on or active is greater than about 25% the activity level is deemed to be high, and the probability the patient is free from AF is lower; (f) when the percentage of time the detected source is on or active is greater than between about 26% and about 30% the activity level is deemed to be high; (g) when the percentage of time the detected source is on or active is less than about 30% the activity level is deemed to be low, and the probability the patient is free from AF is deemed to be higher; (h) when the percentage of time the detected source is on or active is less than between about 26% and about 30% the activity level is deemed to be low, and the probability the patient is free from AF is deemed to be higher, (i) the flow angle variability level corresponding to one or more EGF flow angles computed over a predetermined period of time; (j) a flow angle level exceeding a range between about 4 and 5 degrees measured over about 20 milliseconds is deemed to be high, and the probability the patient is free from AF is deemed to be higher; (k) a flow angle level less than a range between about 4 and 5 degrees measured over about 20 milliseconds is deemed to be low, and the probability the patient is free from AF is deemed to be lower; (l) the active fractionation level corresponds to a combination of measuring divergence in EGF flow patterns indicative of action potential origins and measuring a percentage of a surface area of the patient's atrium determined to be fractionated on the basis of divergent EGF flow patterns; (l) when the active fractionation level exceeds a level between about 27 percent and about 31 percent of a surface area of an analyzed portion of the patient's atrium exhibiting divergence in EGF flow patterns over a predetermined period of time, the probability the patient is free from AF is lower; (m) when the active fractionation level falls below a level between about 27 percent and about 31 percent of a surface area of an analyzed portion of the patient's atrium exhibiting divergence in EGF flow patterns over a predetermined period of time, the probability the patient is free from AF is higher; (n) the EVI is generated in accordance with the formula: $EVI=(1-p$ (source activity)$^\alpha \cdot p$ (flow angle variability)$^\beta \cdot (1-p$ (active fractionation))$^\gamma$, where the symbol "·" denotes convolution.

In further embodiments, there are provided methods of generating an estimate or probability of a patient being free from atrial fibrillation (AF), the method employing at least one computing device comprising at least one non-transitory computer readable medium configured to store instructions executable by at least one processor to determine the source and location of the atrial fibrillation in the patient's heart, the computing device being operably connected to a display or monitor, the methods comprising: (a) receiving electrogram signals acquired from electrodes located inside the patient's heart; (b) using the computing device, assigning positions of the electrodes on a mapping electrode assembly employed to acquire the electrogram signals to their corresponding electrogram signals; (c) using the computing device, providing or generating a map, representation, or data set of the electrode positions; (d) using the computing device, processing the electrogram signals to generate a plurality of electrogram surfaces corresponding at least partially to the map, representation, or data set; (e) using the computing device, processing the plurality of electrogram surfaces through time to generate at least one electrographical flow (EGF) map, representation, pattern, or data set; (f) using the computing device, processing the at least one EGF map, representation, pattern, or data set to determine at least two of source activity levels, flow angle variability (FAV) levels, and active fractionation (AFR) levels corresponding thereto; (g) using the computing device, determining and generating, on the basis of a combination of the determined at least two of source activity levels, FAV levels, and AFR levels, an electrographical volatility index (EVI) representative of the estimate or probability of the patient being free from AF, and (h) presenting at least one of the EVI and the estimate or probability of the patient being free from AF on a display, monitor, or printer to a user.

In some embodiments, such methods can further comprise any one or more of: (a) the computing device convolving at least two of the determined source activity levels, the determined flow angle variability levels, and the determined active fractionation levels with one another to provide the estimate or probability of the patient being free from AF; (b) the determined source activity levels corresponding to at least one of Type A atrial behavior exhibiting stable rotors and drivers and Type B atrial behavior where rotors switch on and off; (c) the determined flow angle variability levels corresponding to Type D atrial behavior exhibiting stable reentry patterns with low FAV; (d) the determined active fractionation levels corresponding to Type E atrial behavior exhibiting a combination of active fractionation and action potential flow origins; (e) the activity level corresponding to a percentage of time a detected source is determined to be on or active; (f) when the percentage of time the detected source is on or active is greater than about 25% the activity level is deemed to be high, and the probability the patient is free from AF is lower; (g) when the percentage of time the detected source is on or active is greater than between about 26% and about 30% the activity level is deemed to be high; (h) when the percentage of time the detected source is on or active is less than about 30% the activity level is deemed to be low, and the probability the patient is free from AF is deemed to be higher; (i) when the percentage of time the detected source is on or active is less than between about 26% and about 30% the activity level is deemed to be low, and the probability the patient is free from AF is deemed to be higher; (j) the flow angle variability level corresponds to one or more EGF flow angles computed over a predetermined period of time; (k) a flow angle level exceeding a range between about 4 and 5 degrees measured over about 20 milliseconds is deemed to be high, and the probability the patient is free from AF is deemed to be higher; (l) a flow angle level less than a range between about 4 and 5 degrees measured over about 20 milliseconds is deemed to be low, and the probability the patient is free from AF is deemed to be lower; (m) the active fractionation level corresponds to a combination of measuring divergence in EGF flow patterns indicative of action potential origins and measuring a percentage of a surface area of the patient's atrium determined to be fractionated on the basis of divergent EGF flow patterns; (n) when the active fractionation level exceeds a level between about 27 percent and about 31 percent of a surface area of an analyzed portion of the patient's atrium exhibiting divergence in EGF flow patterns over a predetermined period of time, the probability the patient is free from AF is lower, (o) when the active fractionation level falls below a level between about 27 percent and about 31 percent of a surface area of an analyzed portion of the patient's atrium exhibiting divergence in EGF flow patterns over a predetermined period of time, the probability the patient is free from AF is higher; and (p) generating the EVI is determined in accordance with the formula: $EVI=(1-p \text{ (source activity)})^{\alpha} \cdot p \text{ (flow angle variability)}^{\beta} \cdot (1-p \text{ (active fractionation)})^{\gamma}$, where the symbol "·" denotes convolution.

Further embodiments are disclosed herein or will become apparent to those skilled in the art after having read and understood the claims, specification and drawings hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Different aspects of the various embodiments will become apparent from the following specification, drawings and claims in which:

FIGS. 15 through 30 illustrate various aspects of some embodiments of electrographic flow (EGF) mapping and applications, and methods, systems, devices and components associated therewith.

FIG. 31 shows a schematic representation of one embodiment of an Electrographic Volatility Index (EVI);

FIG. 34 shows a schematic representation of another embodiment of an Electrographic Volatility Index (EVI);

FIG. 38 shows results obtained by generating probability of freedom from AF statistics from development and validation cohorts;

FIG. 39 shows an example of the results that can be obtained by adding an active fractionation mechanism to the generation of EVI;

FIG. 40 shows further results obtained by generating probability of freedom from AF statistics from development and validation cohorts;

FIG. 43 shows a summary of EVI statistical validation;

FIGS. 44-48 show comparisons of EVI scores generated for re-do AF patients and persistent AF patients, and FIG. 49 shows a summary of the results obtained by comparing EVI scores generated for re-do AF patients and persistent AF patients.

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for diagnosing and treating cardiac rhythm disorders in a patient's heart using electrophysiological mapping techniques, as well as imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities. Such cardiac rhythm disorders and irregularities, include, but are not limited to, arrhythmias, atrial fibrillation (AF or A-fib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

Figure 1A:
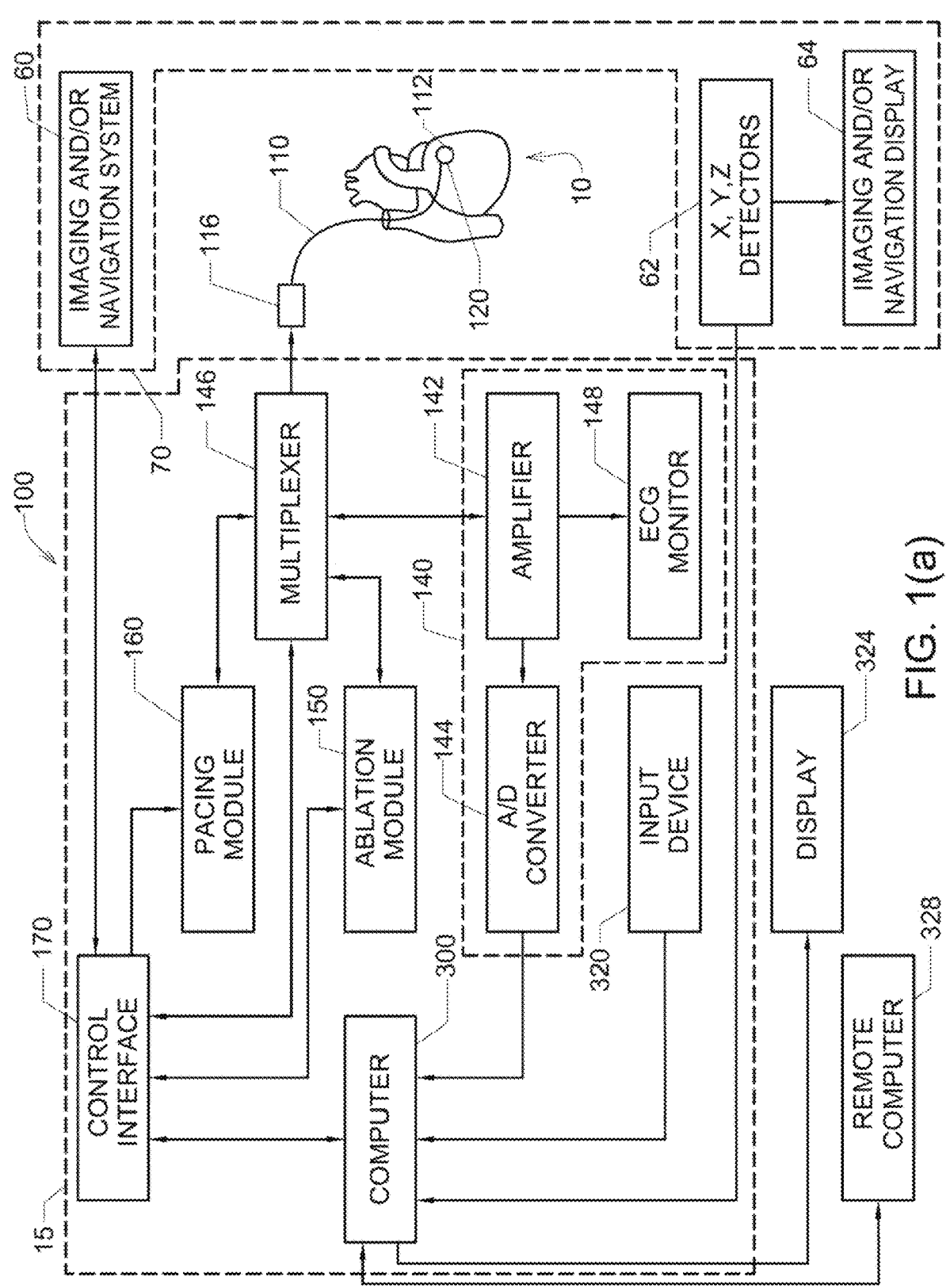
FIG. 1(a) shows one embodiment of a combined cardiac electrophysiological mapping (EP), pacing and ablation system 100.

Referring now to FIG. 1(*a*), there is illustrated one embodiment of a combined cardiac electrophysiological mapping (EP), pacing and ablation system 100. Systems 100 and 300 may also include operable connections to other systems, computers, computing devices, servers, LANs, and WANs, the Cloud, and other devices through internet connections. WiFi and Bluetooth connections, LAN and WAN connections, and other connecting means, systems and devices known to those skilled in the art of computing systems, devices, and components.

Note that in some embodiments system 100 may not include ablation module 150 and/or pacing module 160. Among other things, the embodiment of system 100 shown in FIG. 1(*a*) is configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 is further configured to treat the location of the source of the cardiac rhythm disorder or irregularity, for example by ablating the patient's heart at the detected location.

The embodiment of system 100 shown in FIG. 1(*a*) comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer 300 may be displayed on display or monitor 324 or other output devices (not shown in FIG. 1(*a*)). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 is typically introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters, including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 includes a plurality of 64 electrodes, probes and/or sensors A1 through H8 arranged in an 8×8 grid that are included in electrode mapping assembly 120, which is configured for insertion into the patient's heart through the patient's blood vessels and/or veins. Other numbers, arrangements, configurations and types of electrodes in catheter 110 are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal end 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes against a site of the endocardium at a location that is to be mapped, such as through the use of a Biosense Webster® PENTARAY® EP mapping catheter. The intracardiac or electrogram signals detected by the catheter's electrodes provide data sampling of the electrical activity in the local site spanned by the array of electrodes.

In one embodiment, the electrogram signal data are processed by computer 300 to produce a display showing the locations(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10. This permits a medical practitioner to move interactively and quickly the electrodes of catheter 110 towards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magneto-cardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10.

Many different permutations and combinations of the various components of system 100 are contemplated having, for example, reduced, additional or different numbers of electrical sensing and other types of electrodes, sensors and/or transducers.

Continuing to refer to FIG. 1(*a*), EP mapping system or data acquisition device 140 is configured to condition the analog electrogram signals delivered by catheter 110 from electrodes A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 or data acquisition device 140.

In some embodiments, the rate at which individual electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARDS LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARDS CLEARSIGN™ amplifier, which is configured to amplify and condition electrocardiographic signals of biologic origin and pressure transducer input, and transmit such information to a host computer (e.g., computer 300 or another computer).

As shown in FIG. 1(*a*), and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1(*a*)). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170.

Control of ablation module 150 can initiate the delivery of a programmed series of electrical energy pulses to the endocardium via catheter 110 (or a separate ablation catheter, not shown in FIG. 1(*a*)). One embodiment of an ablation method and device is disclosed in U.S. Pat. No. 5,383,917 to Desai et al., the entirety of which is hereby incorporated by reference herein.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1(*a*)). One embodiment of a pacing module is disclosed in M. E. Josephson et al., in "VENTRICULAR ENDOCARDIAL PACING II, The Role of Pace Mapping to Localize Origin of Ventricular Tachycardia," The American Journal of Cardiology, vol. 50, November 1982.

Computing device or computer 300 is appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1(*a*), system 100 also comprises a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the inserted catheter 110 and its electrodes A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 70 is used to help identify and determine the precise two- or three-dimensional positions of the various electrodes included in catheter 110 within patient's heart 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers for imaging or navigation system 70.

Medical navigation systems suitable for use in the various embodiments described and disclosed herein include, but are not limited to, image-based navigation systems, model-based navigation systems, optical navigation systems, electromagnetic navigation systems (e.g., BIOSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC® STEALTHSTATION® system).

In view of the structural and functional descriptions provided herein, those skilled in the art will appreciate that portions of the described devices and methods may be configured as methods, data processing systems, or computer algorithms. Accordingly, these portions of the devices and methods described herein may take the form of a hardware embodiment, a software embodiment, or an embodiment combining software and hardware, such as shown and described with respect to computer system 300 illustrated in FIG. 1(*b*). Furthermore, portions of the devices and methods described herein may be a computer algorithm or method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer algorithm products. It will be understood that such block diagrams, and combinations of blocks diagrams in the Figures, can be implemented using computer-executable instructions. These computer-executable instructions may be provided to one or more processors of a general-purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

Figure 1B:
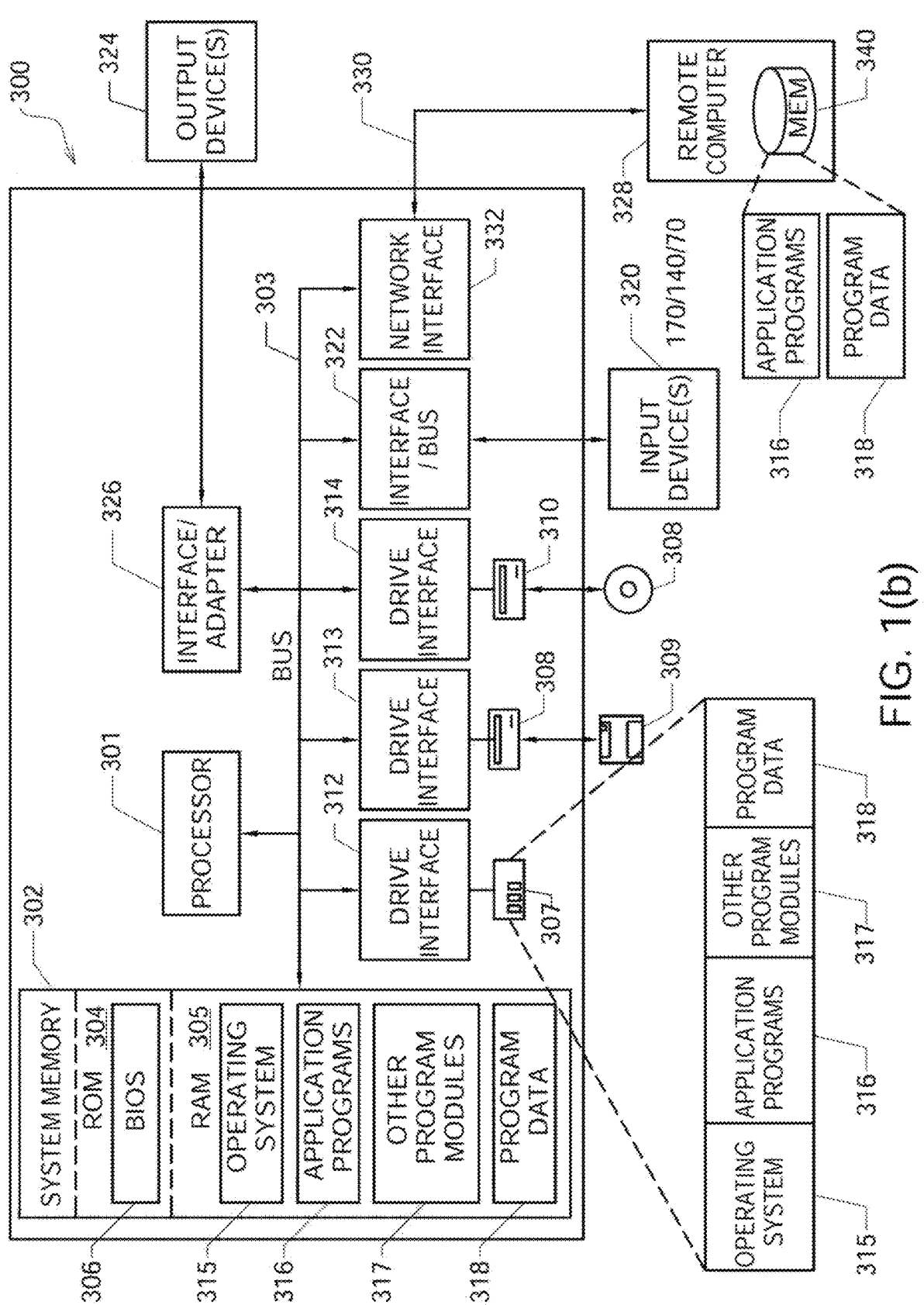
FIG. 1(b) shows one embodiment of a computer system 300.

In this regard, FIG. 1(b) illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate devices/ nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random-access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient for assessing heart function and/or for determining parameters for delivering a therapy and/or assessing heart function, such as shown and described herein with respect to FIGS. 1-10(f).

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing algorithm or method (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 2:
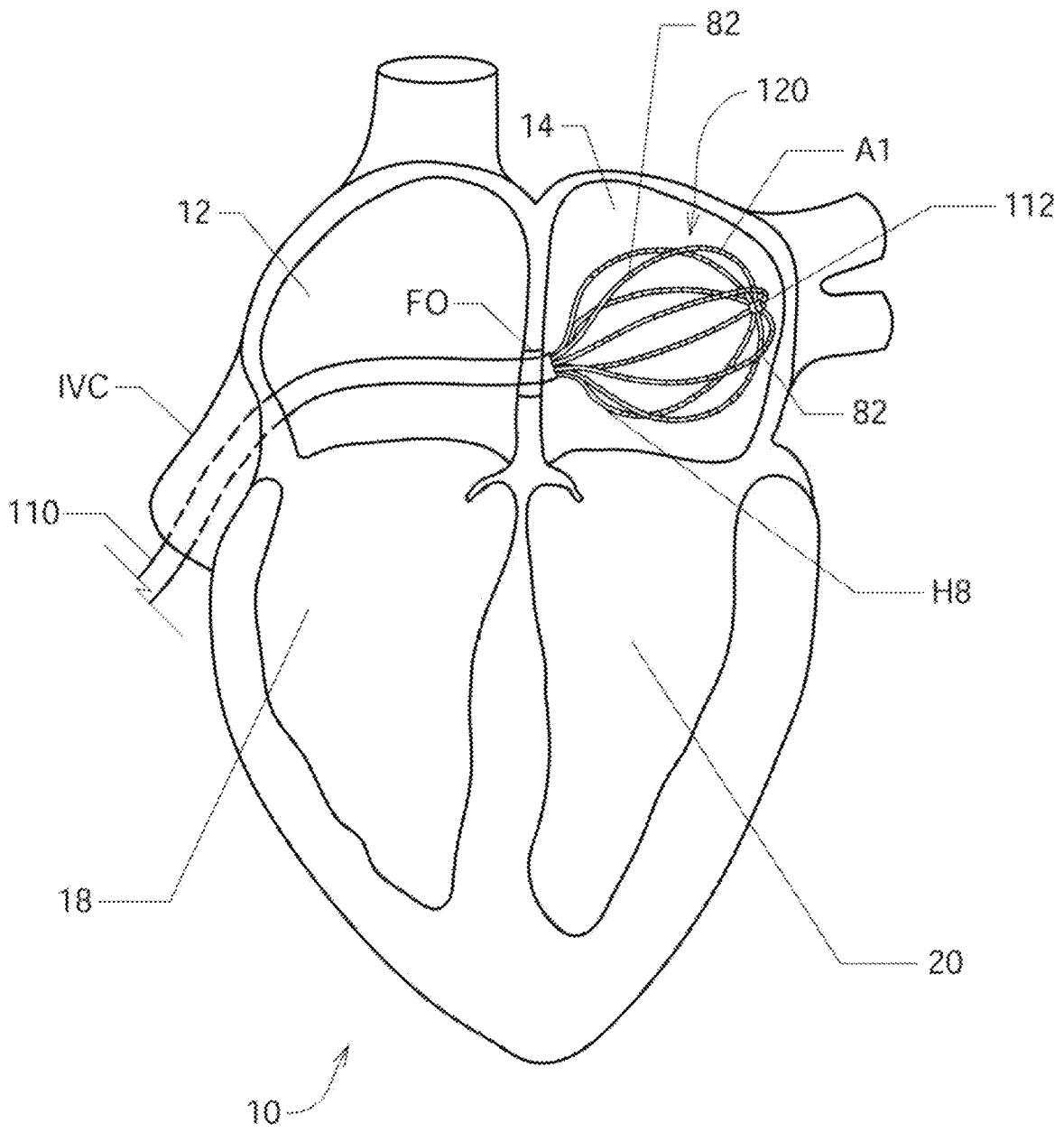
FIG. 2 shows an illustrative view of one embodiment of a distal portion of catheter 110 inside a patient's left atrium 14.

Referring now to FIG. 2, there is shown an illustrative view of one embodiment of a distal portion of catheter 110 inside a patient's left atrium 14. As shown in FIG. 2, heart 10 includes right atrium 12, left atrium 14, right ventricle 18, and left ventricle 20. Mapping electrode assembly 120 is shown in an expanded or open state inside left atrium 13 after it has been inserted through the patient's inferior vena cava and foramen ovalen ("IVC" and "FO" in FIG. 2), and in one embodiment is configured to obtain electrogram signals from left atrium 12 via an 8×8 array of electrodes A1 through H8, which as shown comprises individual electrodes 82. Mapping electrode assembly and catheter 110 may also be positioned within the patient's right atrium 12, left ventricle 18 and right ventricle 20.

Figure 3:
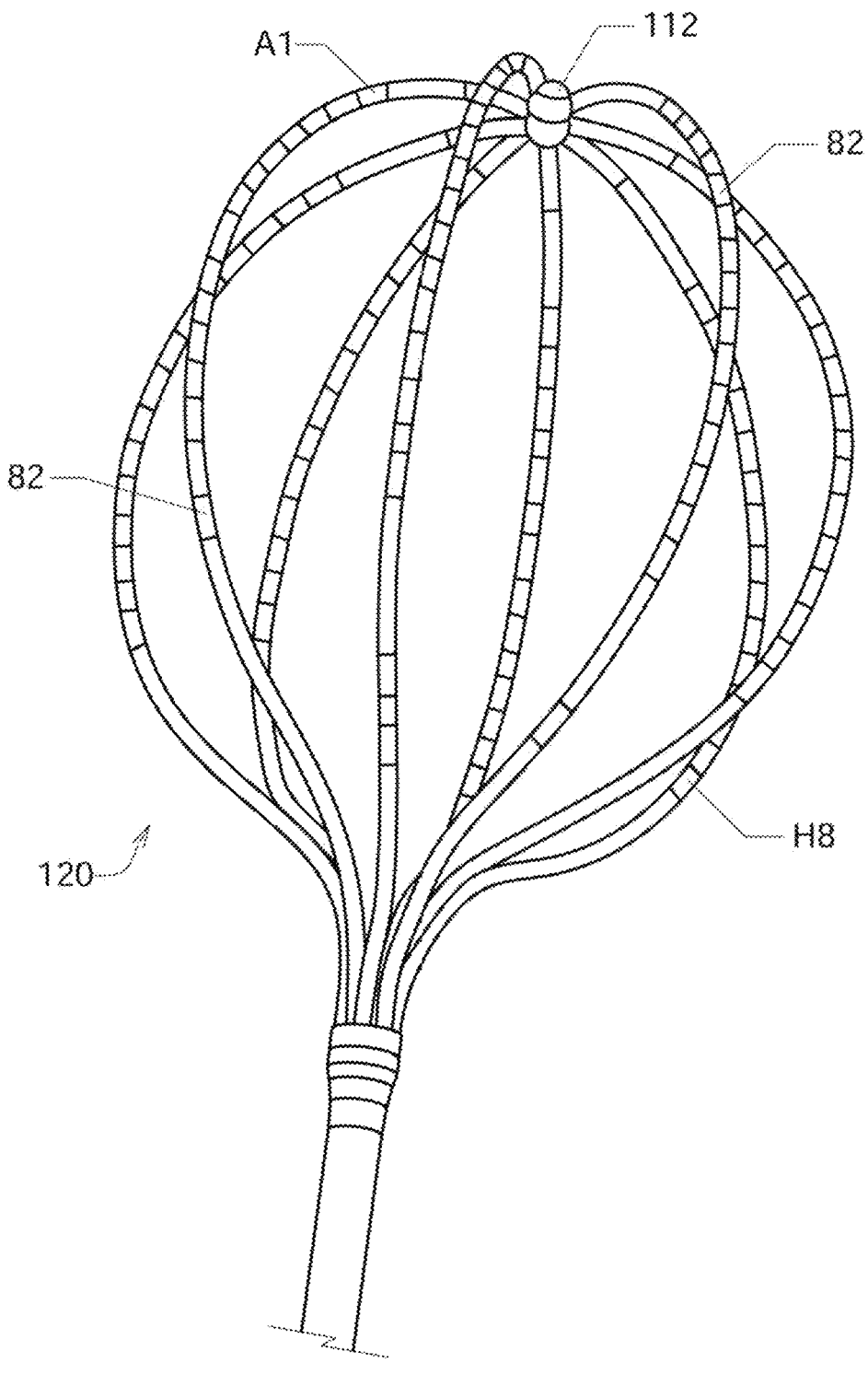
FIG. 3 shows an illustrative embodiment of a mapping electrode assembly 120.

FIG. 3 shows an illustrative embodiment of a mapping electrode assembly 120, which in FIG. 3 forms a distal portion of a Boston Scientific® CONSTELLATION® full contact mapping catheter. The CONSTELLATION EP catheter permits full-contact mapping of a patient's heart chamber, and may also be employed to facilitate the assessment of entrainment, conduction velocity studies, and refractory period in a patient's heart 10. Mapping electrode assembly 120 shown in FIG. 3 permits the simultaneous acquisition of longitudinal and circumferential signals for more accurate 3-D mapping, and features a flexible basket design that conforms to atrial anatomy and aids aid in accurate placement. Sixty-four electrodes A1 through H8 (or individual electrodes 82) can provide comprehensive, real-time 3-D information over a single heartbeat.

Figure 4:
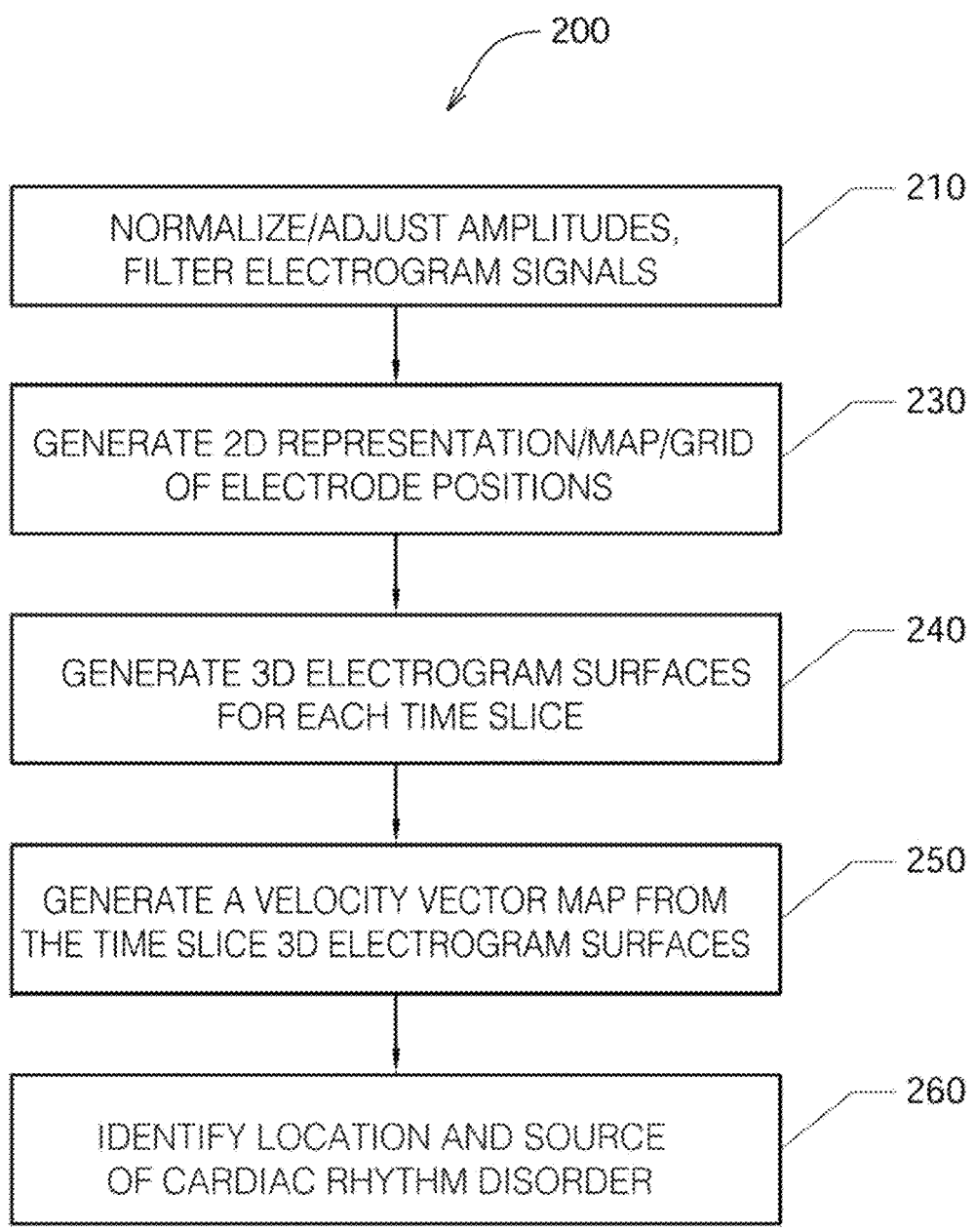
FIG. 4 shows one embodiment of an algorithm or method 200 of detecting a location of a source of at least one cardiac rhythm disorder in a patient's heart.
Figure 5A:
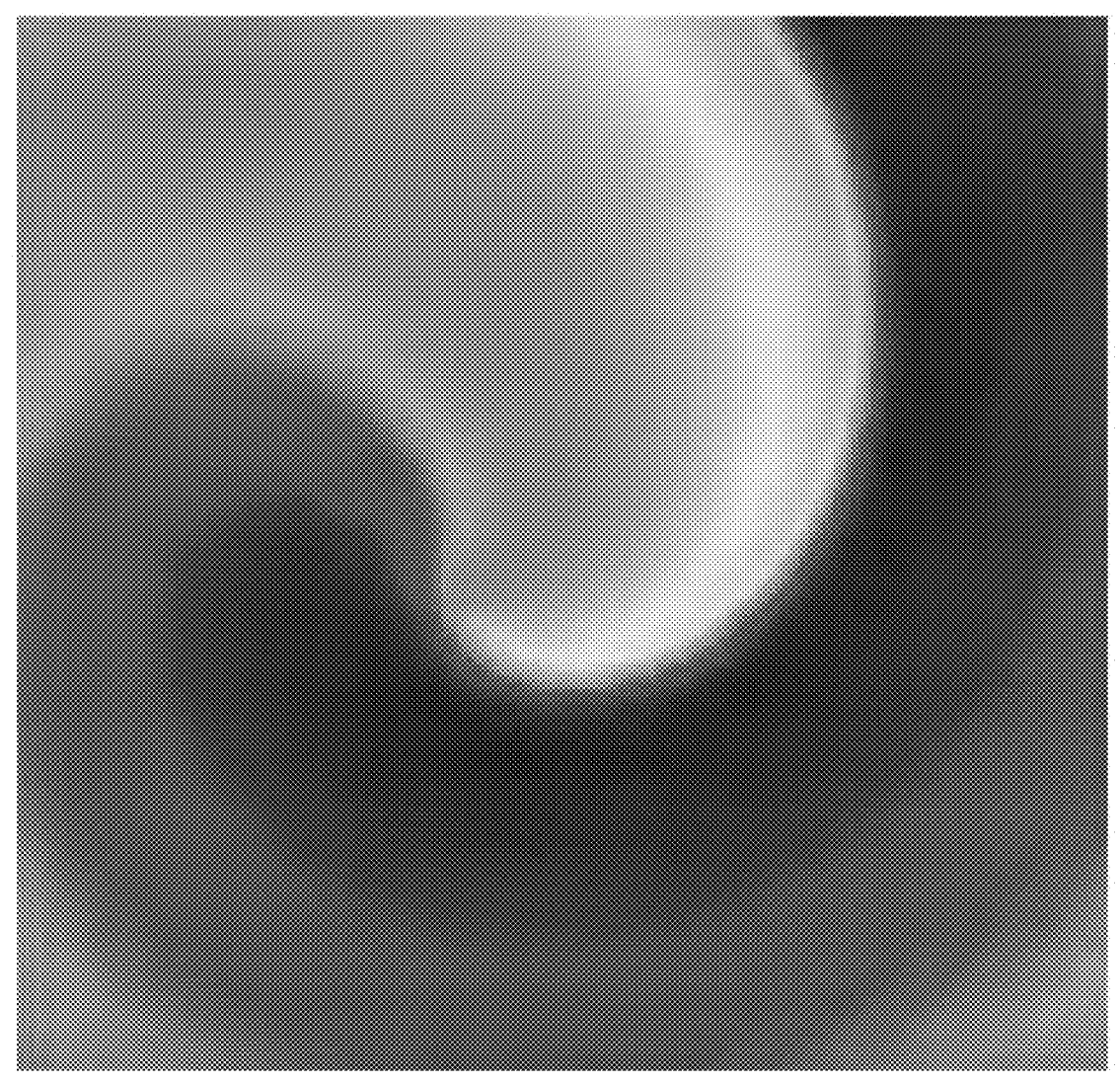
FIG. 5(a) shows a simple rotor model.
Figure 5B:
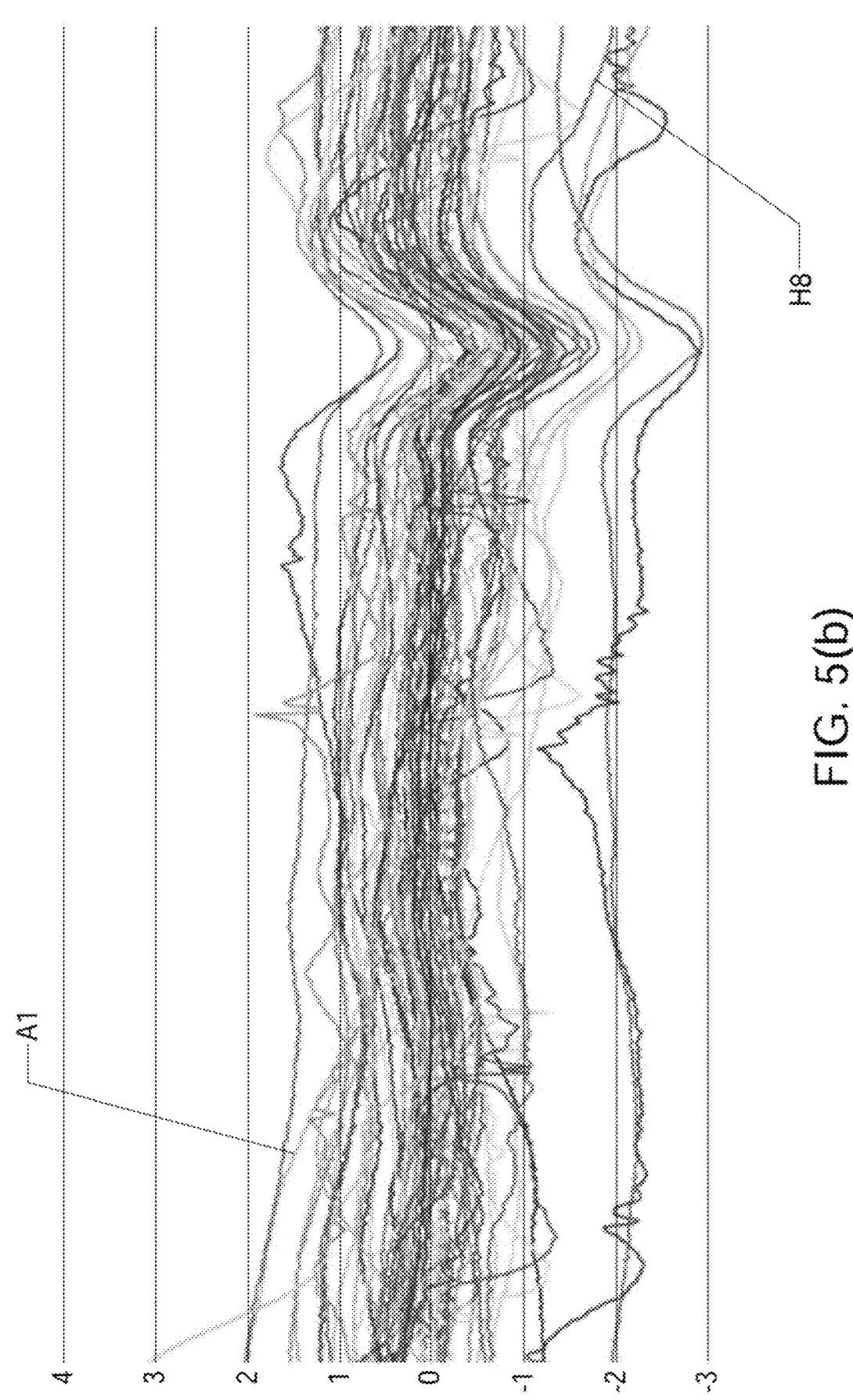
FIG. 5(b) shows sensed artifacts in electrogram signals.
Figure 5C:
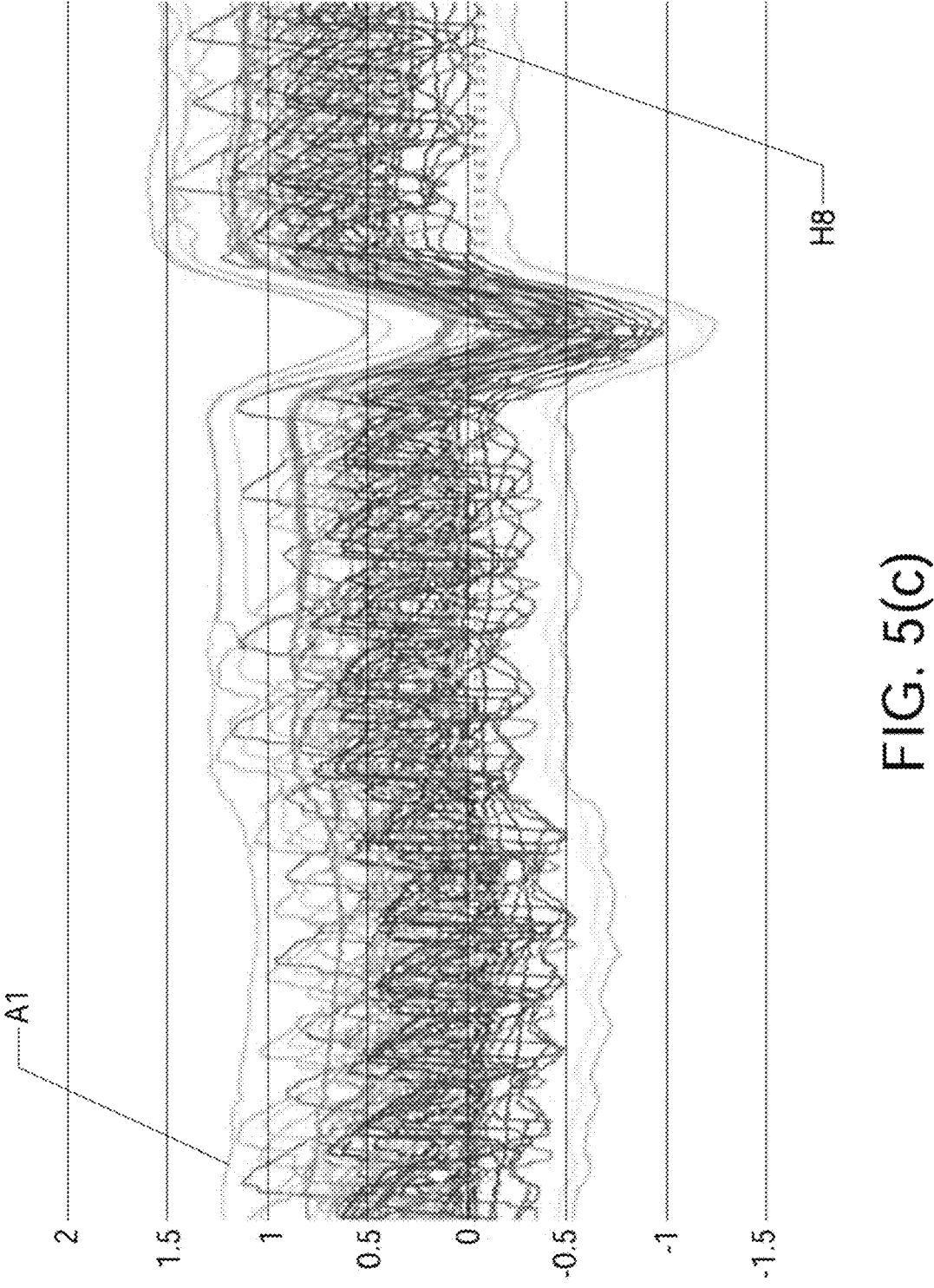
FIG. 5(c) shows the artifacts of FIG. 5(b) superimposed on simulated ECG signals.
Figure 5D:
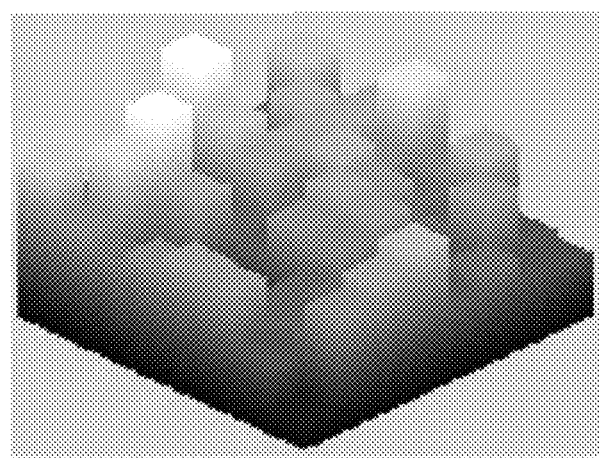
FIG. 5(d) shows a box plot corresponding to an 8×8 array of 64 electrode signals.
Figure 5E:
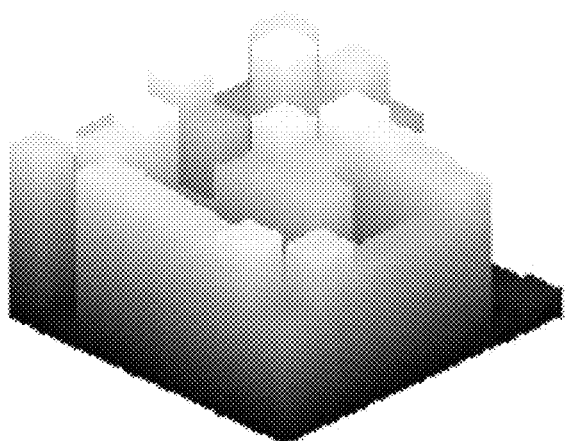
FIG. 5(e) shows the data of FIG. 5(d) after they have been subjected to an electrode signal normalization, adjustment and filtering process.
Figure 5F:
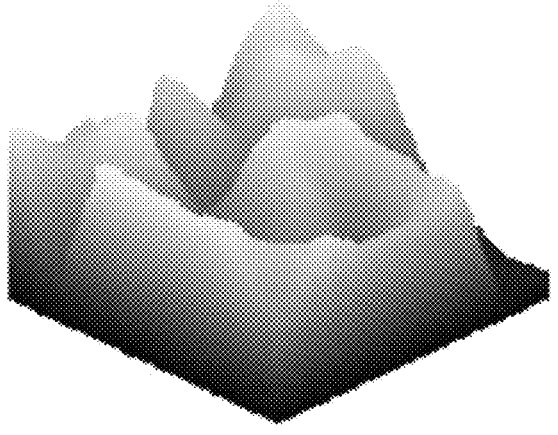
FIG. 5(f) shows a surface generated from the data shown in FIG. 5(e)
Figure 5G:
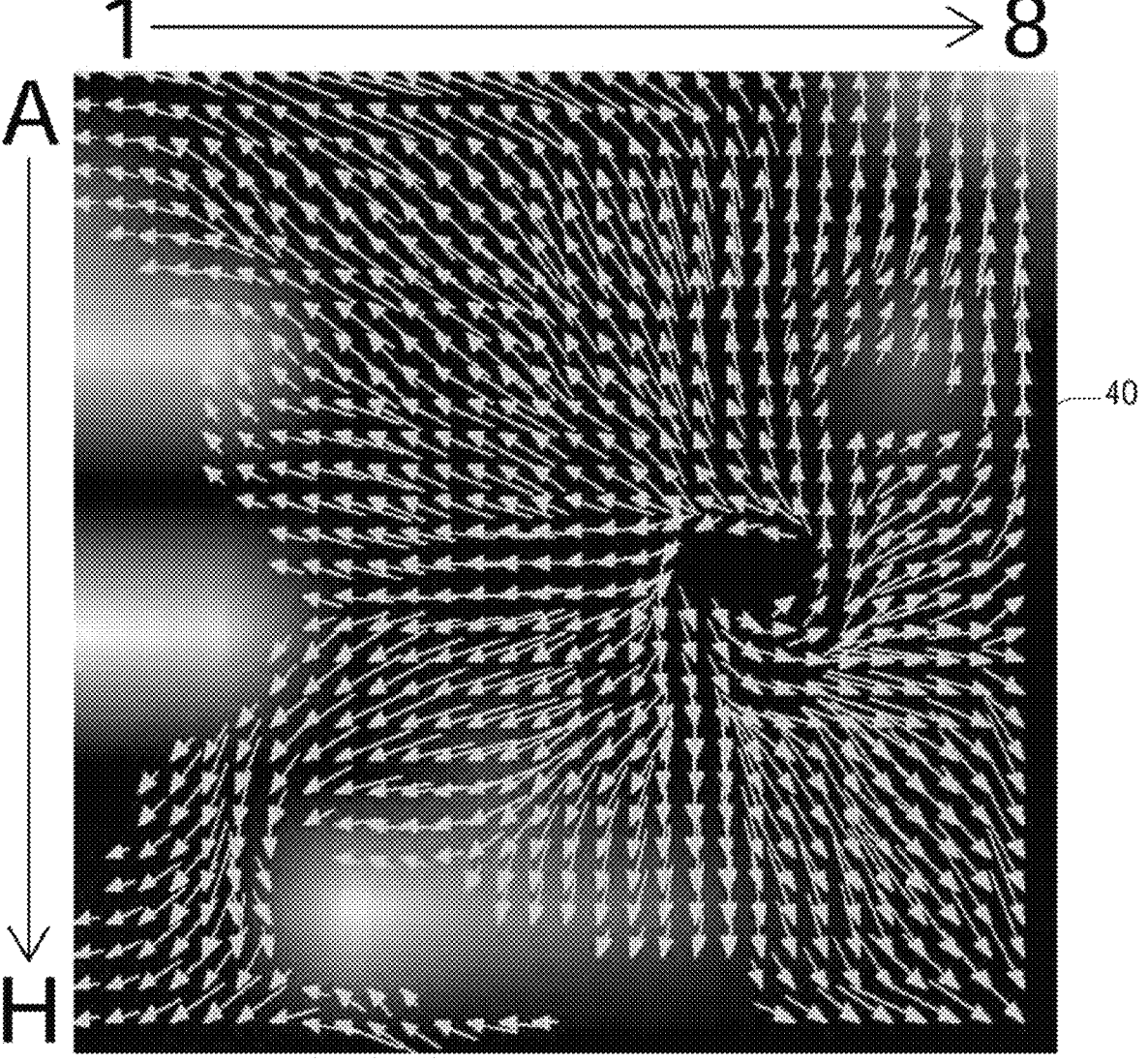
FIG. 5(g) shows wavefront velocity vectors.

FIG. 4 shows one embodiment of a method 200 of detecting a location of a source of at least one cardiac rhythm disorder in a patient's heart. At step 210, the amplitudes of electrogram signals acquired from electrodes located inside a patient's heart are normalized or adjusted. At step 230, positions A1 through H8 corresponding to each of the electrodes of mapping electrode assembly 120 are assigned to the individual electrogram signals that have been acquired. At step 230, a two-dimensional (2D) spatial map of electrode positions A1 through H8 is generated or provided. In some embodiments, a three-dimensional (3D) spatial map of electrode positions A1 through H8 is generated or provided. (As discussed above, fewer or more than 64 electrodes may be used to measure electrogram signals and/or surface ECGs, and electrode arrays other than 8×8 or rectangular grids are contemplated in the various embodiments.)

For discrete or selected times over which the electrogram signals are being analyzed and processed, at step 240 the amplitude-adjusted electrogram signals are processed to generate a plurality of three-dimensional electrogram surfaces (which according to one embodiment may be smoothed electrogram surfaces) corresponding at least partially to the 2D (or 3D) map, one surface being generated for each such discrete time. At step 250, the plurality of three-dimensional electrogram surfaces that have been generated through time are processed to generate a velocity vector map corresponding at least partially to the 2D (or 3D) map. The velocity vector map is configured to reveal the location of the source of the at least one cardiac rhythm disorder. In a subsequent optional step (not shown in FIG. 4), method 200 further comprises ablating patient's heart 10 at the location of the source of the cardiac rhythm disorder indicated by the velocity vector map.

Algorithm or method 200 outlined in FIG. 4 presents one embodiment of a method of processing electrogram signals provided by one or more mapping catheters so as to transform time domain waveform information into space domain information, and then calculate velocity vector maps that correspond to normalized space potential profile movements for each point in space. For reasons that are explained below, algorithm or method 200 has the advantages that it is robust against artifacts and provides a virtual resolution that is higher than the actual electrode density employed to acquire the EP mapping data through the use of a fitting algorithm or method that determines the most likely mean spatial velocity map derived from hundreds of individual samples of amplitude patterns recorded by the mapping electrodes.

As described above, in step 210 of FIG. 4 the amplitudes of electrogram signals acquired from electrodes located inside the patient's heart are normalized or otherwise adjusted. In step 240, the amplitude-adjusted electrogram signals are processed across a 2D or 3D map to generate a plurality of three-dimensional electrogram surfaces, one surface being generated for each such discrete time. In one embodiment, the resulting individual time-slice surfaces can be strung together sequentially to provide a time-varying depiction of electrical activation occurring over the portion of the patient's heart that has been monitored. According to embodiments that have been discovered to be particularly efficacious in the field of intracardiac EP monitoring and data processing and analysis, at least portions of the electrogram surfaces are found to correspond to estimated wave shapes, and are generated using Green's function, which in some embodiments, and by way of non-limiting example, may be combined with two- or three-dimensional bi-harmonic spline interpolation functions to generate such surfaces.

In one embodiment, electrogram signal data acquired from the patient's heart 10 are not equidistantly sampled. For example, in one such embodiment, electrogram signal data acquired from the patient's heart 10 are not equidistantly sampled by mapping electrode assembly 120, and instead are assigned their respective chessboard locations A1 through H8 as approximations of electrode locations in a cylindrical 2D projection of a grid representative of the interior surface of the patient's heart that is being mapped. In many applications, it has been discovered that such approximations of electrode locations yield perfectly useable and accurate results when steps 230 through 250 are carried out after steps 210 and 230.

In another embodiment, when superimposing the acquired electrogram signal data onto a 2D or 3D map or grid in step 230, the electrogram signal data may be associated with their actual or more accurately estimated positions in the 2D projection of the grid using positional data provided by, for example, imaging or navigation system 70. Resampling of electrogram signals on the grid may also be carried out. Gridding may also be caried out such as by convolution-type filtering, Kriging, and using splines. Most gridding techniques operate on an equidistant grid and solve the equations governing the gridding process with either finite difference or finite element implementations.

One approach that has been discovered to work particularly well with electrogram signal data is to determine the Green's function associated with each electrogram value assigned to a given chessboard location, and then construct the solution as a sum of contributions from each data point, weighted by the Green's function evaluated for each point of separation. Biharmonic spline interpolation, which as described above may be employed in conjunction with Green's function, has also been discovered to work especially well in the context of processing and analyzing electrogram signal data. In some embodiments, undesirable oscillations between data points are removed by interpolation with splines in tension, also using Green's function. A Green's function technique for interpolation and surface fitting and generation of electrogram signal data has been found to be superior to conventional finite-difference methods because, among other things, the model can be evaluated at arbitrary x,y locations rather than only on a rectangular grid. This is a very important advantage of using Green's function in step 240, because precise evenly-spaced-apart grid locations, resampling of electrogram signals, and finite-difference gridding calculations are not required to generate accurate representations of electrogram surfaces in step 240.

In one embodiment, Green's function $G(x; x')$ is employed in step 240 for a chosen spline and geometry to interpolate data at regular or arbitrary output locations. Mathematically, the solution is $w(x) = \text{sum} \{c(i) G(x'; x(i))\}$, for $i=1, n$, and a number of data points $(x(i), w(i))$. Once the $n$ coefficients $c(i)$ have been calculated, the sum may be evaluated at any output point $x$. A selection is made between minimum curvature, regularized, or continuous curvature splines in tension for either 1-D, 2-D, or 3-D Cartesian coordinates or spherical surface coordinates. After removing a linear or planar trend (i.e., in Cartesian geometries) or mean values (i.e., spherical surfaces) and normalizing residuals, a least-squares matrix solution for spline coefficients c(i) may be determined by solving the n-by-n linear system w(j)=sum-over-i{c(i) G(x(j); x(i))}, for j=1, n; this solution yields an exact interpolation of the supplied data points. For further details regarding the algorithms and mathematics underlying Green's function, see, for example: (1) "Moving Surface Spline Interpolation Based on Green's Function," Xingsheng Deng and Zhong-an Tang, Math. Geosci (2011), 43:663-680 ("the Deng paper"), and (2) "Interpolation with Splines in Tension: A Green's Function Approach," Paul Wessel and David Bercovici, Mathematical Geology, 77-93, Vol. 30, No. 1, 1998 ("the Wessel paper"). The respective entireties of the Deng and Wessel papers are hereby incorporated by reference herein.

Still further details regarding the use of Green's function in interpolating and generating surfaces may be found in: Interpolation by regularized spline with tension: I. Theory and implementation, Mitasova, H., and L. Mitas, 1993, Math. Geol., 25, 641-655; Parker, R. L., 1994, Geophysical Inverse Theory, 386 pp., Princeton Univ. Press, Princeton, N.J.; Sandwell, D. T., 1987, Biharmonic spline interpolation of Geos-3 and Seasat altimeter data, Geophys. Res. Lett., 14, 139-142; Wessel, P., and J. M. Becker, 2008, Interpolation using a generalized Green's function for a spherical surface spline in tension, Geophys. J. Int, 174, 21-28, and Wessel, P., 2009, A general-purpose Green's function interpolator, Computers & Geosciences, 35, 1247-1254. Moving Surface Spline Interpolation Based on Green's Function, Xingsheng Deng, Zhong-an Tang, Mathematical Geosciences, August 2011, Volume 43, Issue 6, pp 663-680.

Note, however, that a number of different surface smoothing, surface fitting, surface estimation and/or surface/data interpolation processing techniques may be employed in step 240 of FIG. 4, which are not limited to Green's function, or use in conjunction with Green's function, and which include, but are not limited to, inverse distance weighted methods of interpolation, triangulation with linear interpolation, bilinear surface interpolation methods, bivariate surface interpolation methods, cubic convolution interpolation methods, Kriging interpolation methods, Natural Neighbor or "area-stealing" interpolation methods, spline interpolation techniques (including bi-harmonic spline fitting techniques and "spline with barriers" surface interpolation methods), global polynomial interpolation methods, moving least squares interpolation methods, polynomial least square fitting methods, simple weighted-average operator interpolation methods, multi-quadric biharmonic function interpolation methods, and artificial neural network interpolation methods. See, for example: "A brief description of natural neighbor interpolation (Chapter 2)," in V. Barnett. Interpreting Multivariate Data. Chichester: John Wiley. pp. 21-36.), and "Surfaces generated by Moving Least Squares Methods," P. Lancaster et al., Mathematics of Computation, Vol. 37, No. 155 (July, 1981), 141-158).

As described above, in step 250 of FIG. 4, the plurality of three-dimensional electrogram surfaces may be processed through time to generate a velocity vector map corresponding at least partially to the 2D (or 3D) map, the velocity vector map being configured to reveal the location of the source of the at least one cardiac rhythm disorder. According to embodiments that have been discovered to be particularly efficacious in the field of intracardiac EP monitoring and subsequent data processing and analysis, at least portions of the velocity vector map are generated using one or more optical flow analysis and estimation techniques and methods. Such optical flow analysis techniques may include one or more of Hom-Schunck, Buxton-Buston, Black-Jepson, phase correlation, block-based, discrete optimization, Lucas-Kanade, and differential methods of estimating optical flow. From among these various optical flow estimation and analysis techniques and methods, however, the Hom-Schunck method has so far been discovered to provide superior results in the context of processing and analyzing cardiac electrogram signals, for reasons that are discussed in further detail below.

Two papers describe the Hom-Schunck method particularly well: (1) "SimpleFlow: A Non-iterative, Sublinear Optical Flow Algorithm," Michael Tao et al., Eurographics 2012, Vol. 31 (2012), No. 2 ("the Tao paper"), and (2) "Hom-Schunck Optical Flow with a Multi-Scale Strategy," Enric Meinhardt-Llopis et al., Image Processing On Line, 3 (2013), pp. 151-172 ("the Meinhardt-Llopis paper"). The respective entireties of the Tao and Meinhardt-Llopis papers are hereby incorporated by reference herein.

In "Determining Optical Flow," by B. K. P. Horn and B. G. Schunck, Artificial Intelligence, Vol. 17, pp. 185-204, 1981, the entirety of which is also hereby incorporated by reference herein, a method for finding an optical flow pattern is described which assumes that the apparent velocity of a brightness pattern varies smoothly throughout most of an image. The Hom-Schunck algorithm assumes smoothness in flow over most or all of an image. Thus, the Hom-Schunck algorithm attempts to minimize distortions in flow and prefers solutions which exhibit smoothness. The Hom-Schunck method of estimating optical flow is a global method which introduces a global constraint of smoothness to solve the aperture problem of optical flow.

A description of some aspects of conventional application of the Hom-Schunck method is set forth in U.S. Pat. No. 6,480,615 to Sun et al. entitled "Motion estimation within a sequence of data frames using optical flow with adaptive gradients," the entirety of which is also hereby incorporated by reference herein. As described by Sun et al., the Hom-Schunck computation is based on the observation that flow velocity has two components, and that a rate of change of image brightness requires only one constraint. Smoothness of flow is introduced as a second constraint to solve for optical flow. The smoothness constraint presumes there are no spatial discontinuities. As a result, Horn and Schunck excluded situations where objects in an image occlude or block one another. This is because at object boundaries of an occlusion in an image, discontinuities in reflectance appear.

In conventional optical flow analysis, image brightness is considered at pixel (x,y) in an image plane at time t to be represented as a function I(x,y,t). Based on initial assumptions that the intensity structures of local time-varying image regions are approximately constant under motion for at least a short duration, the brightness of a particular point in the image is constant, so that dI/dt=0. Based on the chain rule of differentiation, an optical flow constraint equation (I) can be represented as follows:

$$Ix(x,y,t) \cdot u + Iy(x,y,t) \cdot v + It(x,y,t) = 0,$$

where $Ix=\partial I(x,y,t)/\partial x$=horizontal spatial gradient of the image intensity;

$Iy=\partial I(x,y,t)/\partial y$=vertical spatial gradient of the image intensity;

$It=\partial I(x,y,t)/\partial t$=temporal image gradient of the image intensity;

u=dx/dt=horizontal image velocity (or displacement); and
v=dy/dt=vertical image velocity (or displacement).

The above optical flow equation is a linear equation having two unknowns, (i.e., u and v). The component of motion in the direction of the brightness gradient is known to be It/(Ix 2+Iy 2)½. However, one cannot determine the component of movement in the direction of the iso-brightness contours at right angles to the brightness gradient. As a consequence, the optical flow velocity (u,v) cannot be computed locally without introducing additional constraints. Hom and Schunck therefore introduce a smoothness constraint. They argue that if every point of the brightness pattern can move independently, then there is little hope of recovering the velocities. However, if opaque objects of finite size are undergoing rigid motion or deformation, neighboring points on the objects should have similar velocities. Correspondingly, the velocity field of the brightness patterns in the image will vary smoothly almost everywhere.

Advantages of the Hom-Schunck algorithm include that it yields a high density of flow vectors, i.e., the flow information missing in inner parts of homogeneous objects is filled in from the motion boundaries. On the negative side, the Hom-Schunck algorithm can be sensitive to noise.

The foregoing discussion regarding how the Hom-Schunck optical flow technique typically focuses on conventional applications, where the brightness or intensity of an object changes over time (which is where the term "optical flow" is derived from). Here, the brightness or intensity of an object is not the issue at hand. Instead, the amplitudes of electrogram signals, and how they change shape and propagate in time and space over a patient's heart, are sought to be determined. One underlying objective of algorithm or method 200 is to produce a vector velocity map, which is a representation of electrographical flow (and not optical flow) within a patient's heart. Instead of looking for differences or changes in optical brightness or intensity, changes in the velocity, direction and shape of electrical signals (i.e., changes in electrographical flow) across a patient's heart are determined. That is, algorithm 200 does not process optical measurement data corresponding to intensity or brightness, but processes electrical measurement data corresponding to amplitude, potential shape, and/or voltage.

One reason why algorithm 200 works so well in detecting the locations of the sources of cardiac rhythm disorders and irregularities is that ion channels in a patient's heart produce action potential voltages that are relatively constant (except in areas of fibrosis). As described above, the Hom-Schunck method assumes "brightness constancy" as one of its key constraints. The normalized/amplitude-adjusted electrogram signals provided by step 210 help satisfy this key constraint of the Hom-Schunck method so that this method may be applied successfully in step 250.

In addition, because of the stability imparted to electrographical flow solutions determined using the Hom-Schunck method, artifacts and noise are generally low in velocity vector maps generated in step 250. In fact, it is believed that the Hom-Schunck method may generally be applied with greater success to electrographical flow data than to optical data because of the unique nature of action potential signals in the human heart, and the manner in which electrogram signals are processed and conditioned before an optical flow analysis is performed on them as described and disclosed herein.

Algorithm or method 200 described and disclosed herein also does not employ spatial derivatives of electrical potentials (as is done by Deno et al. and Kumaraswamy Nanthakumar using "omnipolar" signals) or time derivatives of electrogram signals (as is done in the TOPERA system). Time derivatives of signals are known to increase noise. Algorithm or method 200 has as its key inputs the potentials of electrogram signals (not their derivatives). As a result, algorithm or method 200 is notably free from the effects of spurious noise and artifacts introduced by time-derivative data processing techniques, including in step 250.

In another embodiment, the velocity vector map of step 250 is generated using the Lucas-Kanade optical flow algorithm, which is a differential method for optical flow estimation developed by Bruce D. Lucas and Takeo Kanade. It assumes that the flow is essentially constant in a local neighbourhood of a pixel under consideration, and solves the basic optical flow equations for all the pixels in that neighborhood using least squares criteria. By combining information from several nearby pixels, the Lucas-Kanade method can often resolve the inherent ambiguity of the optical flow equation. It is also less sensitive to image noise than point-wise methods. On the other hand, since it is a purely local method, it cannot provide flow information in the interior of uniform regions of the image. See "An Iterative Image Registration Technique with an Application to Stereo Vision," Bruce D. Lucase, Takeo Kanade, Proceedings of Imaging Understanding Workshop, pp. 121-130 (1981), the entirety of which is hereby incorporated by reference herein.

In yet another embodiment, various aspects of the Hom-Schunck and Lucas-Kanade algorithms are combined to yield an optical flow algorithm that exhibits the local methods inherent in Lucas-Kanade techniques and the global methods inherent in the Hom-Schunck approach and its extensions. Often local methods are more robust under noise, while global techniques yield dense flow fields. See, for example, "Lucas/Kanade Meets Hom/Schunck: Combining Local and Global Optic Flow Methods," Andrés Bruhn, Joachim Weickert, Christoph Schnorr, International Journal of Computer Vision, February 2005, Volume 61, Issue 3, pp 211-231, the entirety of which is hereby incorporated by reference herein.

Various embodiments of algorithm or method 200 feature several advantages with respect to prior art systems and methods that generate intracardiac images and attempt to detect the locations of cardiac rhythm disorders or irregularities. A key underlying assumption of signal processing techniques that employ Hilbert Transform, Discrete Fourier Transforms (DFTs) or Fast Fourier Transforms (FFTs) is that the signal to be transformed is periodic. As is well known in the field of digital signal processing, this underlying basic assumption is frequently incorrect, and can lead to problems such as spectral leakage. Contrariwise, in some embodiments of algorithm or method 200, an underlying assumption is that the electrical activity in a patient's heart is based upon ion channel activation, which is a stochastic and non-periodic process, and so strictly periodic behaviour is not assumed or required in subsequent data processing and manipulation steps.

Indeed, none of steps 210, 230, 240, or 250 of algorithm or method 200 absolutely requires the use of Hilbert or Fourier transforms to process data. Instead, in some embodiments each of these steps can be carried out in the time domain without the need for frequency domain or quadrature conversion. For example, in step 210 the amplitudes of the various traces or electrograms can be normalized or adjusted in the time domain according to a selected standard deviation. In another example, rotors detected by algorithm or method 200 are not assumed to be singularities in a phase map (as is assumed in techniques based upon frequency domain or Hilbert transform signal processing). This key difference also explains why the rotational direction of a rotor can be revealed or detected accurately by algorithm or method 200 (and not at all, or very unsatisfactorily, using the frequency domain or Hilbert transforms of other methods employed to detect rotors). Note that in some embodiments, however, Hilbert, DFT and/or FFT signal processing components may be or are included in the data processing flow of algorithm 200 (e.g., DSP filtering, deconvolution, etc.).

Referring now to FIG. 5(*a*), there is shown a simple rotor model. This model was used to generate simulated ECG signals sensed by an 8×8 array of virtual electrodes. The simple rotor model shown in FIG. 5(*a*) is from "Chaste: An Open Source C++ Library for Computational Physiology and Biology," Gary R. Mirams, et al. PLOS Computational Biology, Mar. 14, 2013, Vol. 9, Issue 3, e1002970, the entirety of which is hereby incorporated by reference herein.

FIG. 5(*b*) shows artifacts in electrogram signals derived from actual patient data, where 400 msec. traces were recorded using a 64-electrode basket catheter located in the left atrium of a patient suffering from atrial fibrillation. As shown in FIG. 5(*b*), the sensed artifacts in the electrogram signals include DC offsets of several millivolts that shift with time, a common far-field ventricular depolarization superimposed on the local potentials sensed by individual electrodes, and noise. Moreover, the amplitudes of the various sensed electrogram signals shown in FIG. 5(*b*) will be seen to vary considerably. These amplitude variations result at least in part on from varying degrees to which individual electrodes touch, or are physically coupled to, the patient's endocardial surface. Electrogram signals corresponding to electrodes in loose, poor or no contact with a patient's endocardium may be an order of magnitude smaller than those where electrodes are well coupled to the endocardial surface.

FIG. 5(*c*) shows the artifacts of FIG. 5(*b*) superimposed on the simulated ECG signals generated from the rotor model of FIG. 5(*a*). FIG. 5(*d*) shows a box plot corresponding to the 8×8 array of 64 electrode signals shown in FIG. 5(*a*) at a selected common time for all traces. Because of the artifacts from FIG. 5(*b*) introduced into the electrogram signals of FIG. 5(*c*), the box plot of FIG. 5(*d*) appears quite irregular and chaotic, and the original spiral shape of the underlying rotor of FIG. 5(*a*) is not discernable to the eye.

The data shown in FIG. 5(*c*) were used to perform an analysis in accordance with algorithm or method 200, which was carried out in three main steps: (1) normalization/ adjustment/filtering of electrogram signals: (2) generating three-dimensional smoothed electrogram surfaces for discrete times or time slices from the normalized/adjusted/ filtered electrogram signals generated in the first main step, and (3) generating a velocity vector map based on the smoothed electrogram surfaces generated in the second main step.

Described now is one embodiment and illustrative example of the first main step of the algorithm or method 200 (normalization/adjustment/filtering of electrogram signals), Referring now to FIG. 5(*e*), there are shown the data of FIG. 5(*d*) after they have been subjected to one embodiment of an electrode signal normalization, adjustment and filtering process. After normalization and filtering, the simple rotor structure shown in FIG. 5(*a*) becomes visible in FIG. 5(*e*). Uniform electrode signal amplitude minima and maxima were first calculated and then applied to individual electrogram signals to generate individual amplitude equalized electrogram signals. Unwanted artifacts such as ventricular depolarization signals were removed from the individual equalized electrogram signals by first averaging all electrogram signals to generate a common electrogram artifact signal, which was then subtracted from each of the equalized individual electrogram signals. The resulting equalized artifact-compensated electrogram signals were then high-pass filtered between 5 and 20 Hz to remove DC offsets from the electrogram signals such that the resulting filtered electrogram signals were approximately zeroed around the X (time) axis. These results are shown in FIG. 5(*e*).

Next, a sliding time window ranging between about 0.1 seconds and about to 1 second in length was applied to each filtered electrogram signal to generate individual amplitude-adjusted electrogram signals. (In some embodiments, the length of the sliding time window corresponds to, or is less than, the slowest repetition frequency expected to be present.) The resulting sliding-window amplitude-adjusted electrogram signals were then stored for later use to generate image backgrounds in velocity vector maps, where they could be used to show low amplitude areas indicative of valve defects/artifacts, loose electrode contact, and/or areas of fibrosis in the patient's myocardium. In the sliding-window amplitude-adjusted electrogram signals, the respective minima and maxima of each position of the sliding time window were used to normalize the amplitude values of all signals between zero and one (or 0 and 255 on an 8-bit integer numeric scale). Because the maximum and minimum values occurred at different time points for electrodes placed in different locations, this process yielded spatial information regarding action potential wave patterns for each sampled time point (more about which is said below).

Now I describe one embodiment and illustrative example of the second main step of the algorithm or method 200 (generating three-dimensional electrogram surfaces for discrete times or time slices, or estimation of spatial wave shapes). The second step of algorithm or method 200 takes the spatial distributions of all electrodes and their normalized voltage values at discrete times (e.g., the data represented by the box plots corresponding to selected discrete times within the selected time window over which electrogram signals were acquired and measured), and estimates or generates from such data or box plots corresponding to given discrete times respective continuous voltage surfaces (or action potential waveform estimates) in space. Because the electrode pattern density is limited, and depending on the method that is used to generate the estimated voltage surfaces, the estimated surfaces typically deviate to some extent from "true" surfaces. Such deviations are usually relatively small in magnitude, however, since the spatial size of the action potential wave given by its velocity (e.g., 0.5 to 1 m/sec.) times the action potential duration (e.g., 0.1 to 0.2 sec.) is much larger (e.g., 0.05 m) than the electrode spacing (e.g., about 1 mm to about 10 mm), and thus spatial aliasing generally does not occur. The electrode grid provided by catheter 110 thus permits relatively good estimates of action potential wave shapes or wavefronts in the form of smoothed electrogram surfaces to be obtained as they propagate across the myocardium. On the other hand, because of the fast sampling rate (which can, for example, range between about 0.25 milliseconds and about 8 milliseconds, and which in some embodiments is nominally about 1 millisecond), changes in the spatial shape or expression of the action potential wavefront from one sample to the next are typically relatively small (e.g., about 1 mm) compared to the electrode distances (which in some embodiments nominally range between about 2 mm and about 7 mm). Thus, algorithm or method 200 is capable of detecting spatial changes in action potential wavefronts or wave shapes using time domain information (i.e., small amplitude changes between time samples) to estimate changes in the spatial domain (where relatively small shifts in action potentials occur at given electrode measurement locations).

One embodiment of a method for estimating action potential wavefronts or wave shapes employs an 8×8 rectangular electrode grid (e.g., TOPERA®-iike) model, which operates in two principal steps. First, each electrode/electrogram signal value at a discrete moment in time defines the height of its respective box in the "chess field" box plots shown in FIGS. 5(*d*) and 5(*e*). Second, a smoothed electrogram surface is generated for each box plot (or discrete slice of time) by calculating for each horizontal x-y point (typically on a 300×300 grid) an average of neighboring z-values (or electrical potentials) in the box plot. In 3D models that take assumed or actual electrode positions and spacing into account (using, e.g., information from a navigation or imaging system), smoothed electrogram surfaces are generated using 20 biharmonic spline interpolation techniques in combination with Green's function. Using the foregoing simple averaging approach, the smoothed electrogram surface of FIG. 5(*f*) was generated from the data shown in FIG. 5(*e*). As shown in FIG. 5(*f*), a spatial wave shape estimate of a rotor appears prominently in the forward center portion of the resulting smoothed surface, which tracks closely the original spiral wave shown in FIG. 5(*a*).

Described now is one embodiment and illustrative example of the third main step of algorithm or method 200 (generating a velocity vector map based on the electrogram surfaces). The third main step of algorithm or method 200 uses the action potential wave shape estimates or electrogram surfaces generated at discrete times or time splices provided by the second main step to calculate a velocity vector map. For each sample interval a spatial wave shape or smoothed surface is calculated according to the second main step described above. Since the wave shapes differ only by a small delta between individual samples, and minimum and maximum values are normalized, shift vectors can be calculated at a spatial resolution that is higher than the spatial resolution of the electrodes (e.g., 30×30 samples), Since individual shifts between samples may differ according to random error, a velocity vector fit can be generated using 40 to 100 samples, where an average of observed shift vectors of the action potential wave shape care calculated. If the angle of a rotating wavefront is shifted by a few degrees per 2a sample, the vector arrows will exhibit a circular pattern and in fact can resolve circles that are much smaller than inter-electrode distances. In one embodiment, the third main step of the algorithm or method employs a vector pattern equation that best fits the observed movement of the evaluated spatial element or wavefront. In one embodiment that has been discovered to provide excellent results, and as described above, the velocity vector map is calculated using the Hom-Schunck optical flow method described above. That is, in one embodiment the Hom-Schunck optical flow method is used in the third main step of algorithm or method 200 to estimate the velocity and direction of wavefronts or wave shapes between sampled times. Velocities of 40 to 100 samples are typically averaged to yield the most stable results.

FIG. 5(*g*) shows the resulting wavefront velocity vectors, which are shown in FIG. 5(*g*) and elsewhere in the Figures as arrows 40 having directions and magnitudes associated therewith, calculated from a series of 60 averaged time slices of smoothed surfaces samples corresponding to the data shown in FIG. 5(*f*). An active rotor is distinctly visible in the right-hand central portion of FIG. 5(*g*), where arrows are flowing tightly in a counterclockwise direction. In FIG. 5(*g*), action potential wavefronts are seen to be moving outwardly away from the detected active rotor (as would be expected in the case of an active rotor)).

Figure 6A:
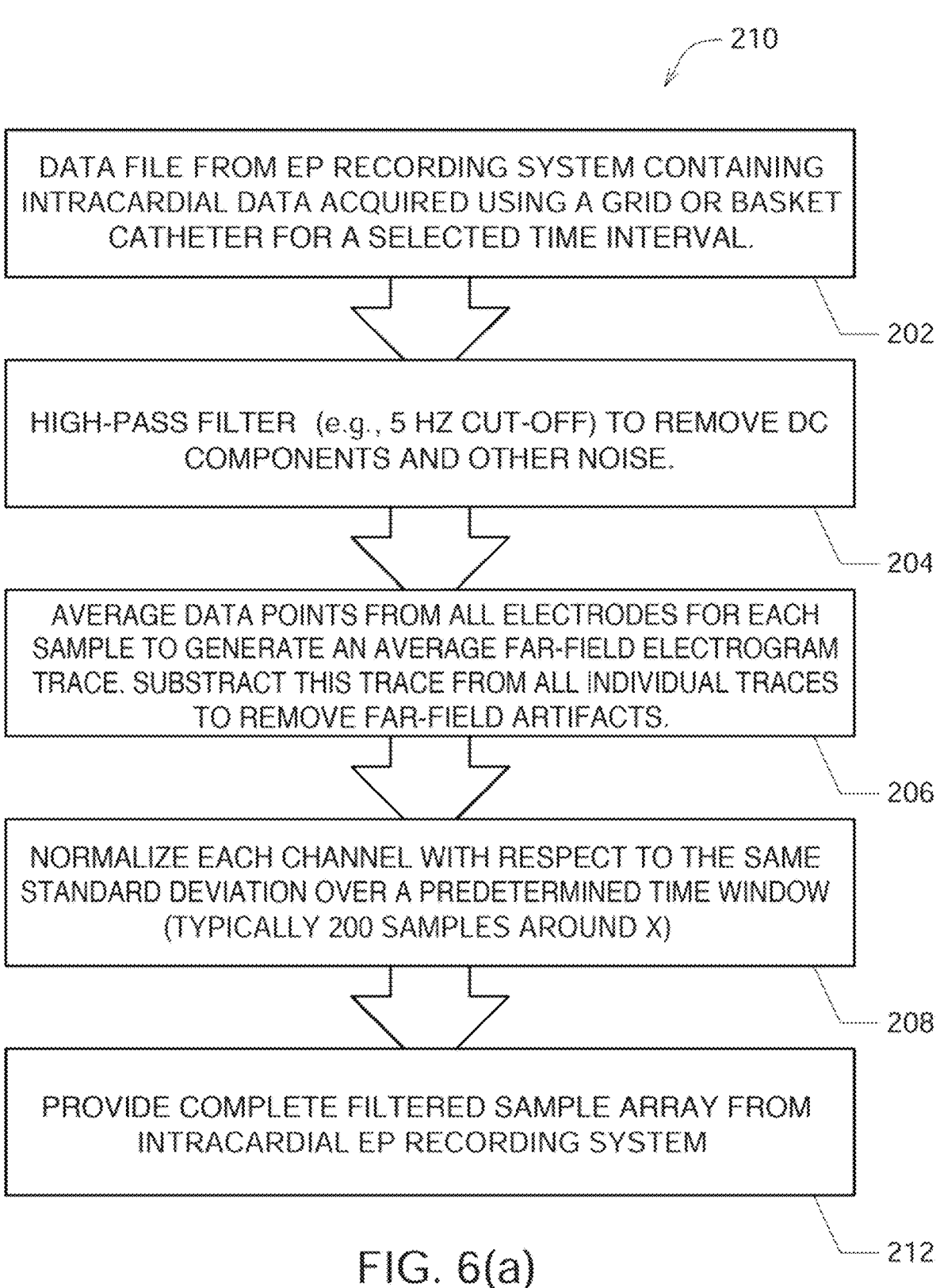
FIGS. 6(a) through 6(c) show details regarding one embodiment of a method or algorithm 200 shown in FIG. 4.
Figure 6B:
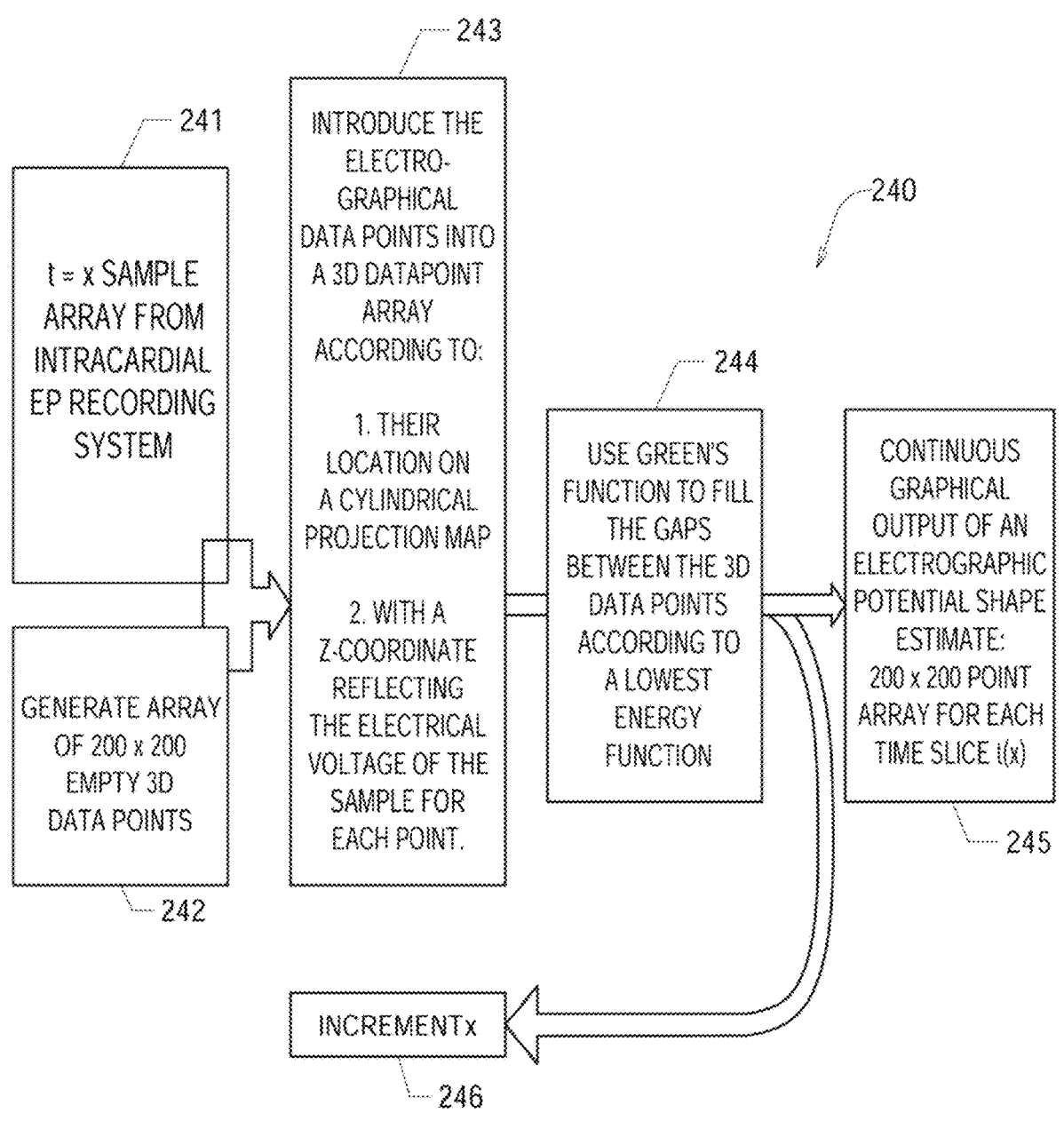
Figure 6C:
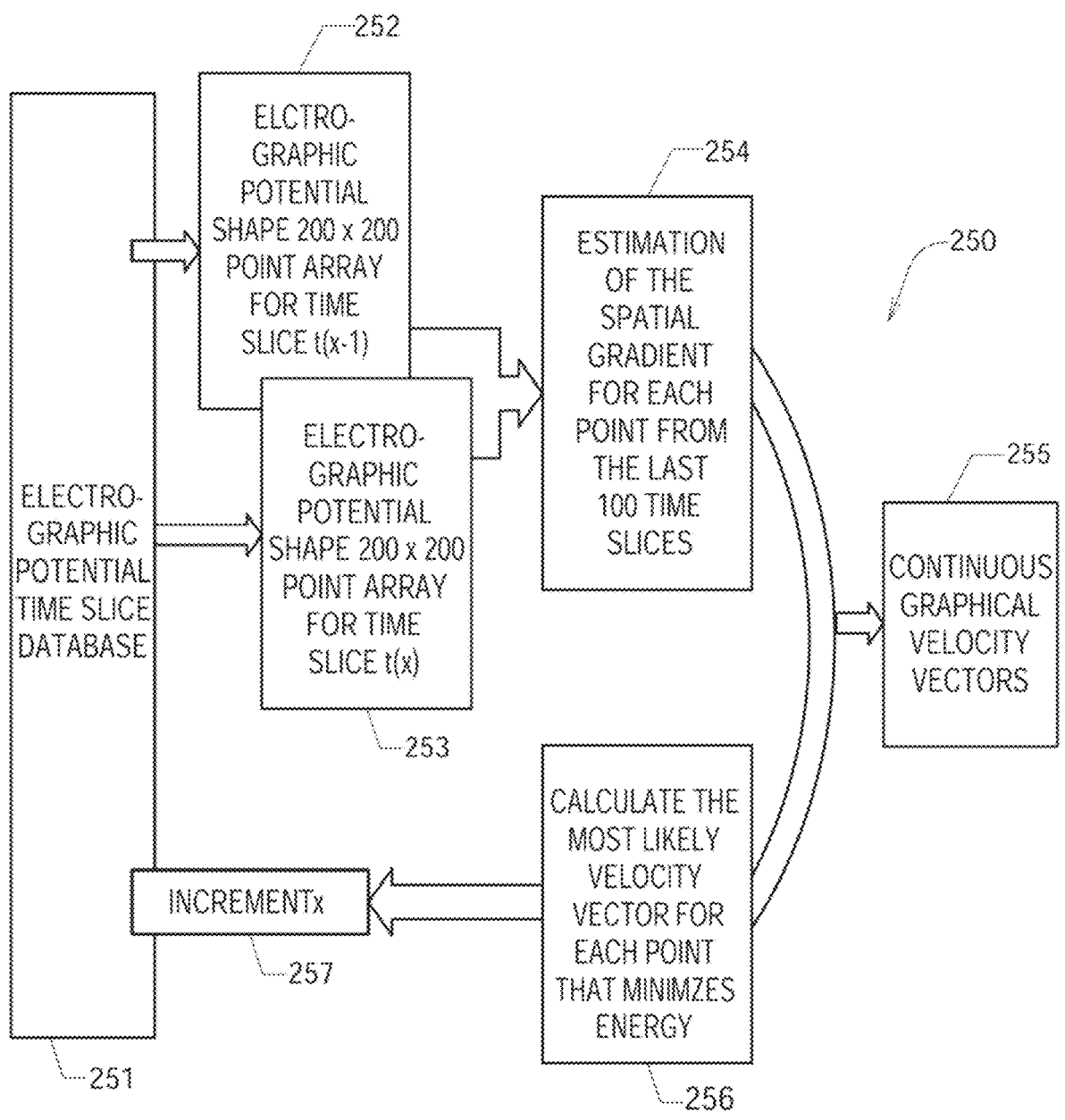
Figure 7A:
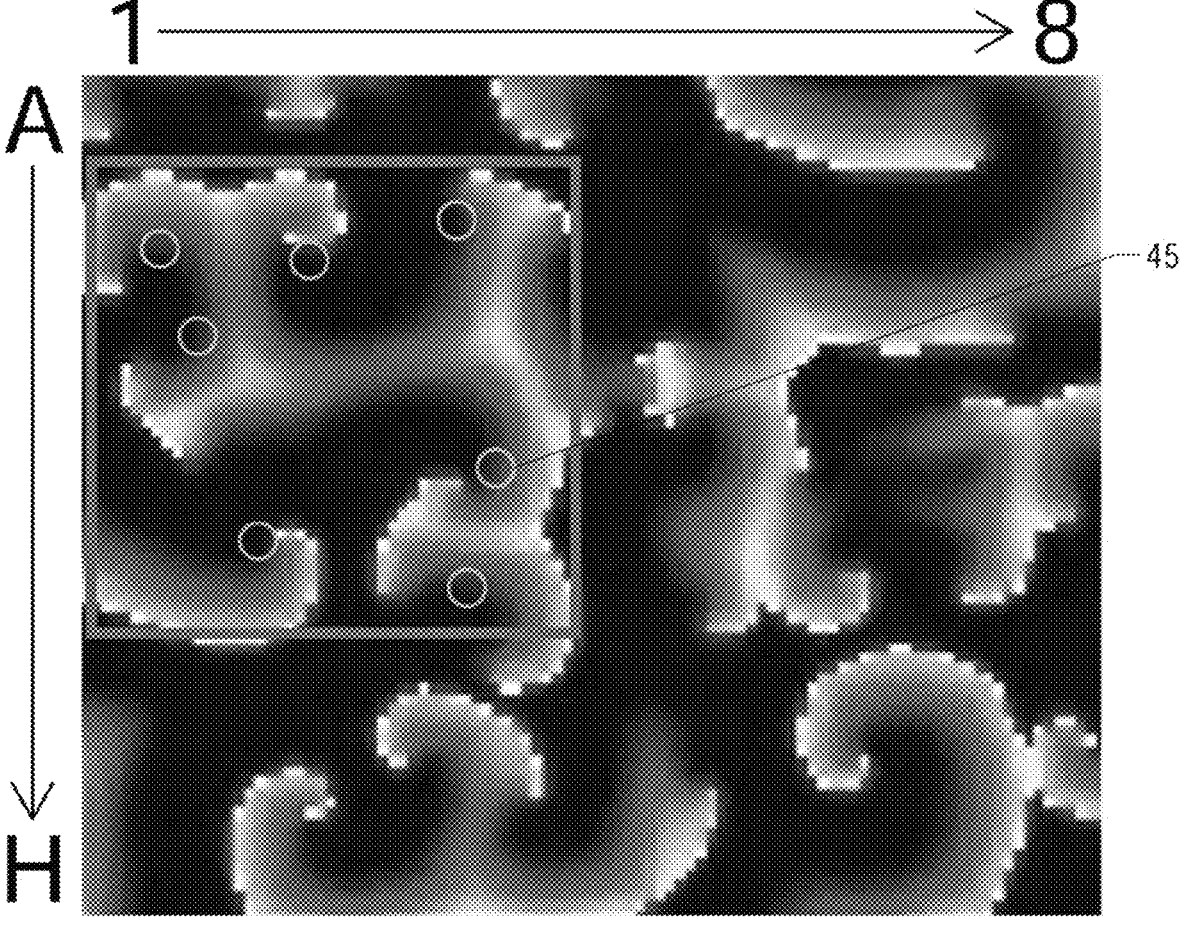
FIGS. 7(a) through 7(j) show the results of processing simulated atrial cardiac rhythm disorder data in accordance with one embodiment of method or algorithm 200.
Figure 7B:
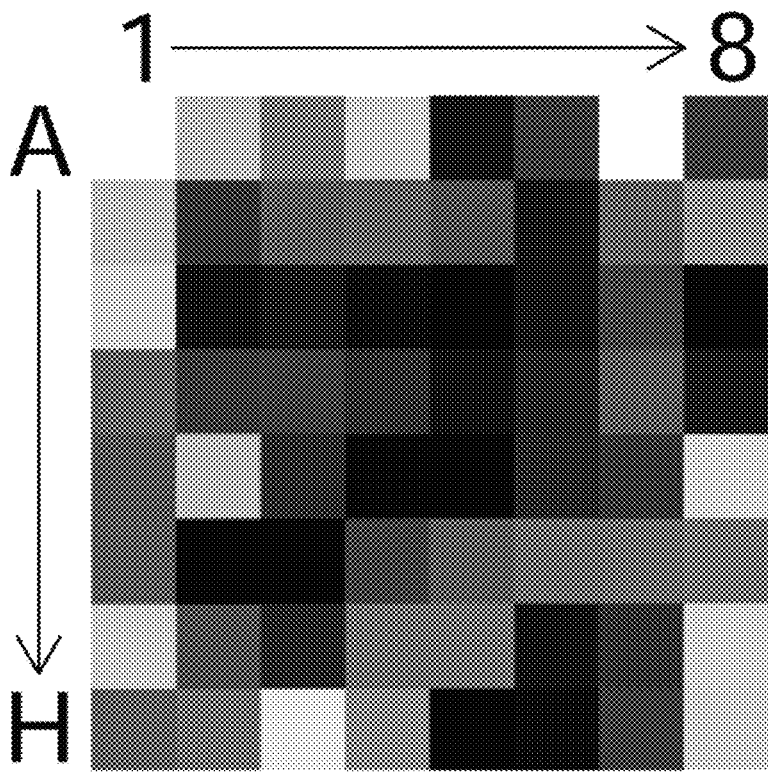
Figure 7C:
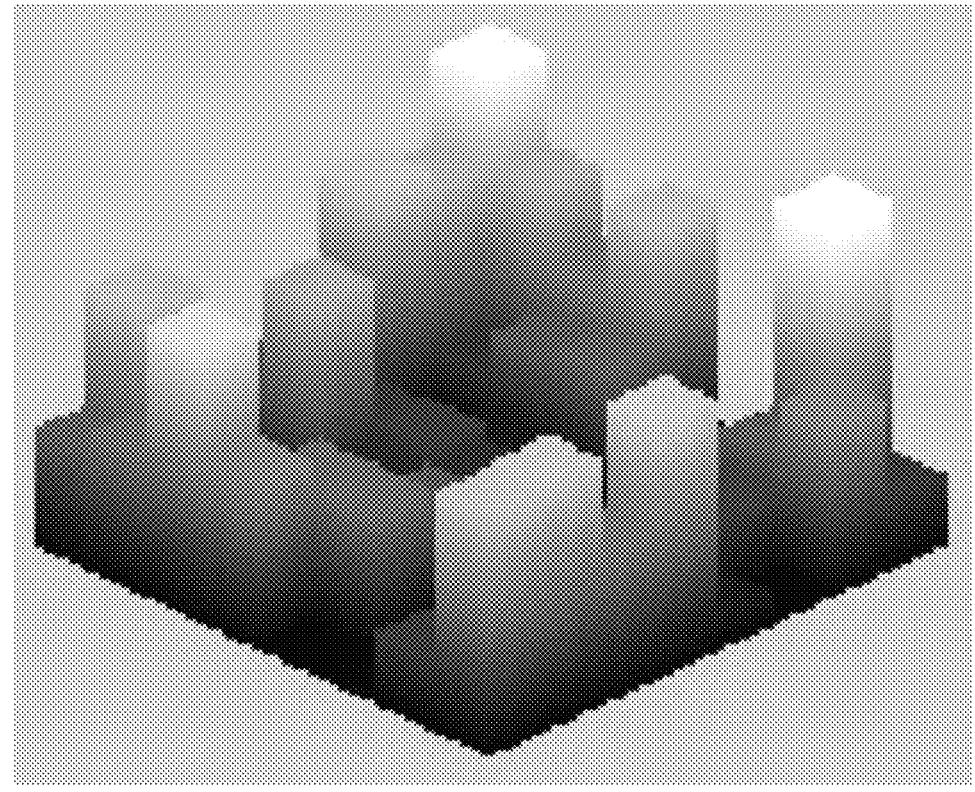
Figure 7D:
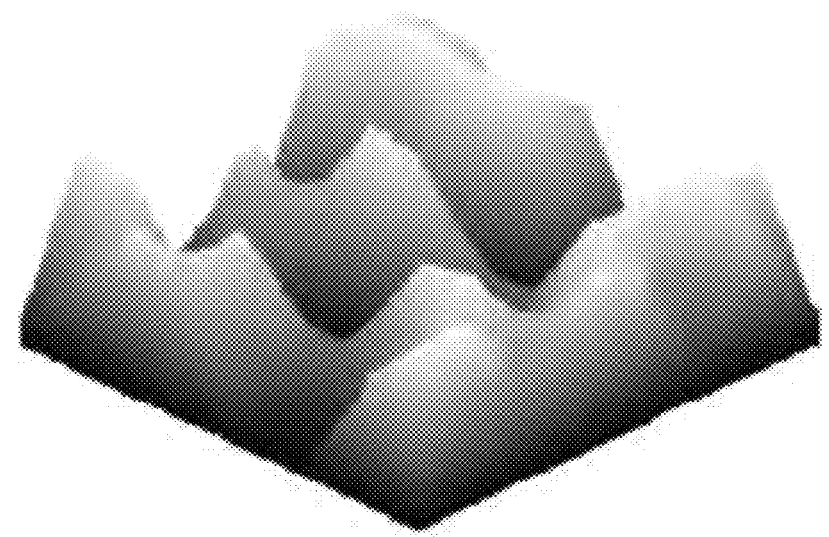
Figure 7E:
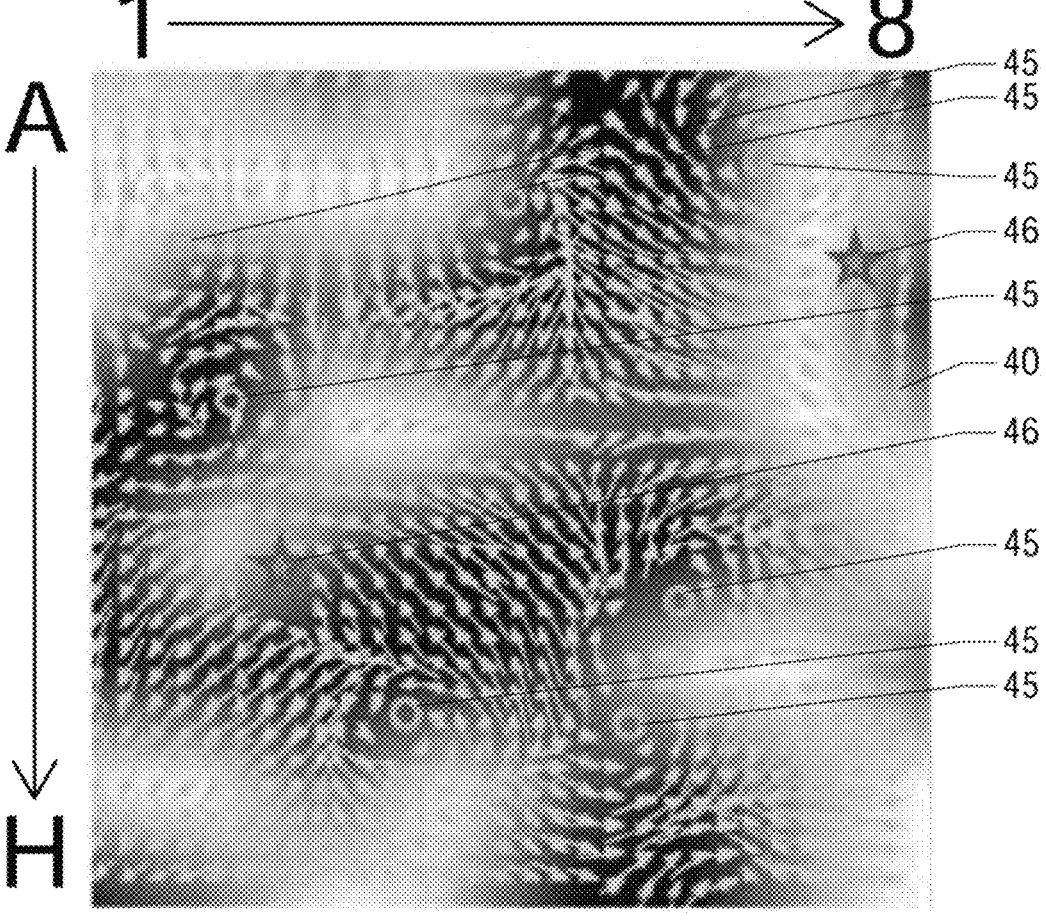
Figure 7F:
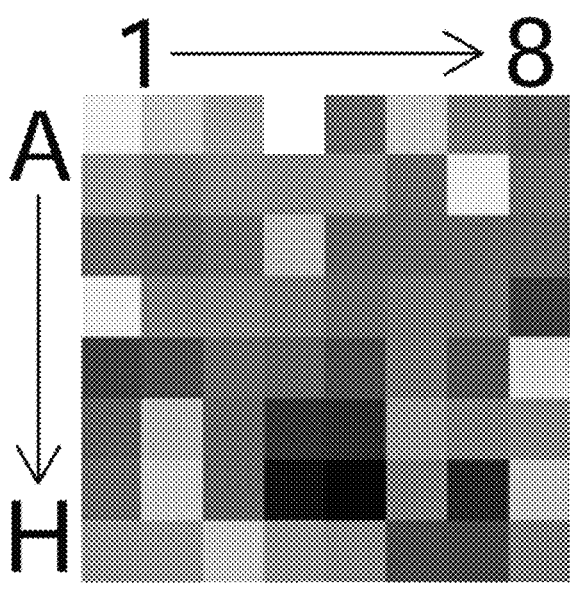
Figure 7G:
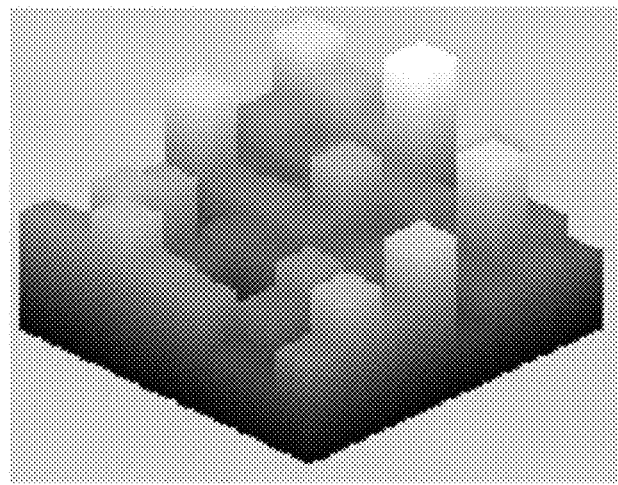
Figure 7H:
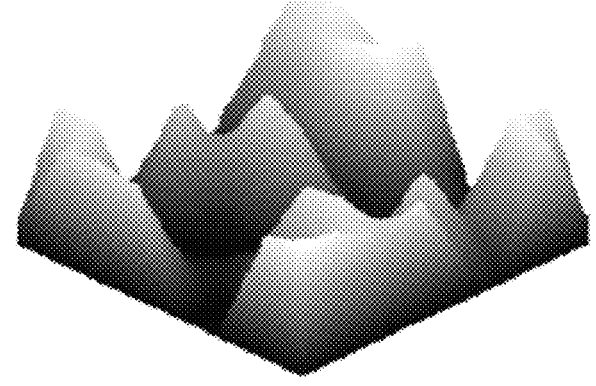
Figure 7I:
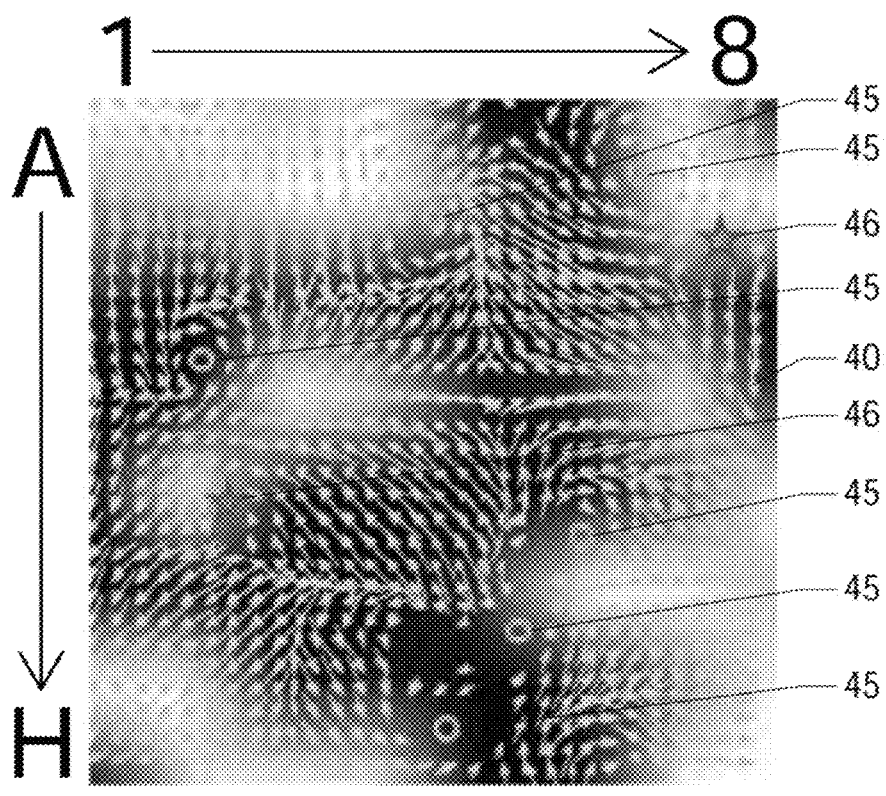
Figure 7J:
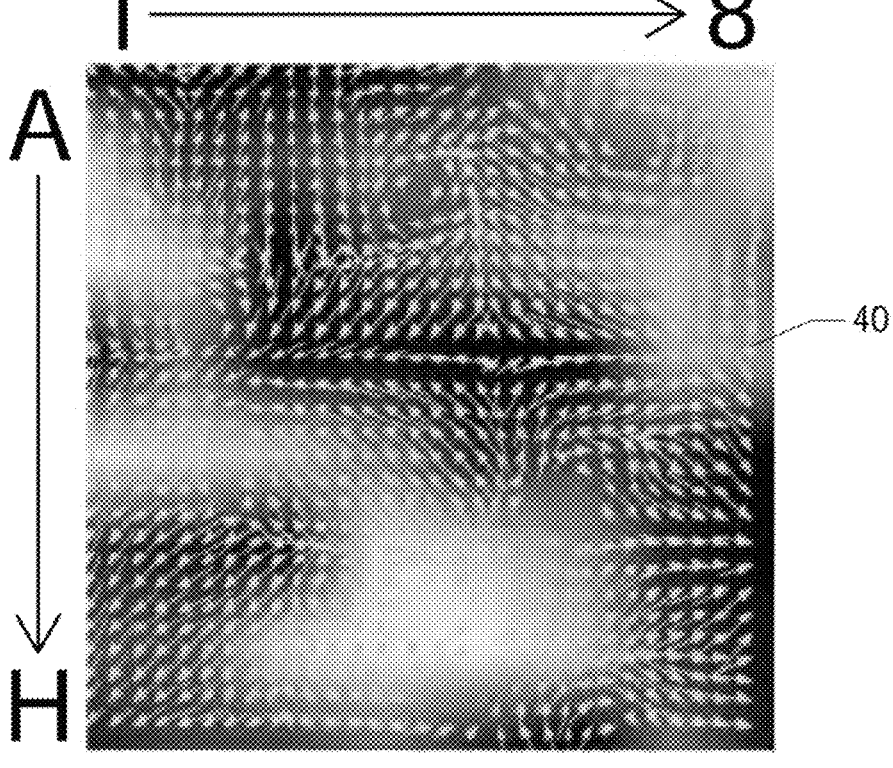

Referring now to FIGS. 6(*a*), 6(*b*) and 6(*c*), and with further reference to FIG. 4, there are shown some of the individual steps corresponding to the three main steps 230, 240 and 250 carried out according to one embodiment of algorithm or method 200 disclosed and described herein.

FIG. 6(*a*) shows one embodiment of steps 202 through 212 of main step 210 of FIG. 4 ("normalize/adjust amplitudes, filter electrogram signals). In FIG. 6(*a*), step 202 is shown as comprising receiving a data file corresponding to the EP recording of electrogram signals from a basket or other type of EP recording catheter positioned in a patient's heart 10. The time interval over which such electrogram signals are recorded inside the patient's heart 10 may, of course, vary according to, among other things, the requirements of the diagnosis, examination, monitoring and/or treatment that is to be performed, and/or the suspected or known cardiac rhythm disorder from which the patient suffers. Illustrative, but non-limiting, examples of such time intervals range between about a second and one minute or more. Bad or poor fidelity traces or electrograms may be selectively removed or edited at this stage.

At step 204, a high-pass filter is applied to the acquired EP data to remove DC offsets, as well as other undesirable low-frequency noise. In one embodiment, a 5 Hz high-pass filter is applied, although other filters, including band-pass filters, are contemplated, including, but not limited to, 10 Hz high-pass filters, 5-20 Hz band-pass filters, and 5-50 Hz band-pass filters. Notch- and low-pass filtering may also be applied in step 204. Hanning, trapezoidal and other digital filtering and/or Fast Fourier Transform (FFT) filtering techniques may also be applied.

At step 206, an average far-field electrogram signal is generated by stacking and averaging all electrogram traces. In the case of atrial EP recordings, the resulting estimate of a far-field ventricular depolarization is subtracted from each trace individually, thereby removing or at least reducing the far-field component therefrom.

At step 208, the amplitudes of individual filtered electrogram signals are normalized with respect to a given standard deviation occurring over a predetermined time window (e.g., a moving window of 200 samples around a time value "x").

At step 212, a complete filtered sample array from the grid or basket catheter is provided as an output from first main step 210.

Referring now to FIG. 6(*b*), there is shown one embodiment of the second main step 230 of algorithm or method 200 shown in FIG. 4 (processing amplitude-adjusted electrogram signals across the 2D or 3D representation, map or grid to generate a plurality of three-dimensional electrogram surfaces, one surface being generated for each selected or predetermined discrete time or time slice).

In FIG. 6(*b*), second main step 240 is shown as including steps 241 and 243, which according to one embodiment are performed in parallel or near-parallel. At step 241, digitally sampled and processed electrogram signals from step 212 of FIG. 6(*a*) are provided, and at step 242 an array of 200×200 empty 3D data points are generated, which correspond to the 2D or 3D representation, map or grid which is to be generated (or has already been generated). In one embodiment, such a representation, map or grid is formed by making a cylindrical projection representation, map or grid that corresponds to an approximate estimate or calculated map of the region of the patient's myocardial wall where the electrogram signals were acquired and measured (see step 243) by catheter 110. Positional data from imaging or navigation system 70 can be provided at this stage to improve the positional accuracy of the individual locations within such grid where electrogram signals were acquired. In one embodiment, for each time slice or sampled time, a Z-value or electrical potential corresponding to the normalized, adjusted and/or filtered measured voltage of each individual electrogram is assigned a location in the representation, map or grid.

At step 244, Green's function, or another suitable surface generating algorithm, is used to generate a surface of Z-values for each time slice or sampled time (more about which is said below). In one embodiment, the surface corresponding to the Z-values is smoothed.

At step 245, the calculated surface corresponding to each time slice or sampled time is provided as an output, with, for example, a 200×200 array of smoothed data points corresponding to the smoothed surface being provided for each time slice or sampled time. Note that in some embodiments the intervals at which time slices are selected, or the individual time slices themselves, may be predetermined, or may be selected automatically or by the user.

FIG. 6(*c*) shows step 250 corresponding to one embodiment of the third main step of FIG. 4 (processing the plurality of three-dimensional electrogram surfaces generated through time to generate a velocity vector map corresponding at least partially to the 2D or 3D map) carried out, by way of non-limiting example, using optical flow analysis and estimation techniques described and disclosed elsewhere herein. In FIG. 6(*c*), third main step 250 is shown as including step 251, which in one embodiment entails sequentially accessing the individual surfaces generated for selected time slices and/or discrete times in step 240. At steps 252 and 253, adjacent time slices are analyzed and processed sequentially. In step 254, a spatial gradient corresponding to each point of the representation, map or grid is calculated say over, for example, the last 100 time slices. At step 255, a continuous graphical output of calculated flow vectors can be provided as a real-time or near-real-time output. At step 256, the most likely flow vector magnitude (or velocity) and direction for each point that minimizes energy is calculated. At step 257, X (or time) is incremented, and the foregoing calculations are repeated and refined, the final output of which is a vector velocity map of the type shown, by way of non-limiting example, in FIGS. 5(*g*), 7(*e*), 7(*i*), 7(*j*), 7(*k*), 7(*l*), 8, 9, 10(*a*), 10(*c*), and 10(*e*).

FIGS. 7(*a*) through 7(*j*) show the results of processing simulated atrial cardiac rhythm disorder data using the methods and techniques described and disclosed above, where the concept of analyzing complex rotor structures was applied to a data set of simulated data. The simulated data shown in FIG. 7(*a*) primarily comprised stable active and passive rotors, as described in Carrick et al. in "Prospectively Quantifying the Propensity for Atrial Fibrillation: A Mechanistic Formulation," R. T. Carrick, P. S. Spector et al.; Mar. 13, 2015, PLOS ONE, DOI:10.1371, journal-.pone.0118746, the entirety of which is hereby incorporated by reference herein. From Carrick, et al.'s video corresponding to the foregoing publication, and referring now to FIG. 7(*a*) herein, stable rotor data were recorded for a frame delineated by the indicated blue square, where there are seven rotors. The recording was accomplished using the luminance of the video frame in an 8×8 matrix with an 8-bit signal depth, thereby to simulate electrogram signal data acquired using a conventional 64-electrode 8×8 basket catheter. The overall video comprised 90 frames. All data shown n FIG. 7(*a*) were taken from frame 60. Signal amplitudes from frame 60 are shown in the chess field and box plots of FIGS. 7(*b*) and 7(*c*), respectively.

In FIG. 7(*a*), 7 rotors are shown as green circles 45 lying within the blue rectangle. In FIG. 7(*b*), a box plot of 8×8 matrix amplitudes is shown having amplitudes corresponding to frame 60. FIG. 7(*d*) shows the estimated wavefront or smoothed surface corresponding to frame 60. FIG. 7(*e*) shows the vector velocity map generated from the data corresponding to FIG. 7(*a*) (which was generated on the basis of all 90 frames or times slices). Reference to FIG. 7(*e*) shows that seven active rotors (marked as green circles 45) are apparent, as are two passive rotors (marked as red stars 46).

Referring now to FIGS. 7(*b*) and 7(*c*), it will be seen that the 2D and 3D box patterns shown therein provide rough estimates of the spatial wavefronts shown in FIG. 7(*a*). In FIG. 7(*d*), however, the original data shown in FIG. 7(*a*) are reproduced fairly accurately, and also provide a good input to the vector velocity map of FIG. 7(*e*) (which nicely reveals the 7 active rotors visible in FIG. 7(*a*)). The yellow vector arrows in FIG. 7(*e*) not only show the rotational centers of the individual rotors, but also show that active rotors indicated by green circles are driving sources of the wave fronts because the calculated vectors of the active rotors always point centrifugally away from the rotor centers. In contrast, the two red stars shown in FIG. 7(*e*) indicate the locations of passive rotors or flow turbulences that, while circular in shape, have centripetal vector directions to at least on one side of the rotor centers associated therewith.

Discrimination between active and passive rotors is critical to making proper therapeutic decisions regarding the delivery of ablation therapy, which should only target structures underlying the drivers of atrial fibrillation (namely, active rotors only, and not passive rotors).

Next, the effects of typical artifact disturbances on the signals of the 64 channels of data shown in FIGS. 7(*a*) through 7(*d*) were determined by introducing simulated variable amplitude DC-offset noise and artifacts into the electrogram signals. The objective was to test the extent to which such artifacts and noise might impair or disable the ability of algorithm or method 200 to detect rotors in the data.

FIGS. 7(*f*) and 7(*g*) show the same box plot data as FIGS. 7(*b*) and 7(*c*), respectively, but with the foregoing-described superimposed and introduced artifacts. That is, FIGS. 7(*f*) and 7(*g*) show the chess field and box plots of the disturbed electrogram signals corresponding to frame 60. After filtering and normalization in step 210, the original rotor structure shown in FIG. 7(*a*) once again becomes visible in FIG. 7(*h*) following completion of the main second step 240 of the algorithm.

Upon applying smoothed surface calculations and fitting (as shown in FIG. 7(*i*)), algorithm or method 200 is seen to detect only five of the seven active rotors shown in FIG. 7(*a*). One additional active rotor, however, was detected at a different location (see FIG. 7(*i*)).

The largest variation in results was seen at positions where the introduction of the artifacts and noise reduced relative amplitude values by the greatest amount, as indicated by the white areas shown in FIG. 7(*j*). The white areas shown in FIG. 7(*j*) were generated by using the sliding-window amplitude-adjusted electrogram signal techniques described above, where electrograms processed using sliding-window techniques were used to generate the image background (including the white areas) shown in the velocity vector map of FIG. 7(*j*). The white areas in FIG. 7(*j*) thus correspond to low amplitude areas potentially indicative of valve defects or artifacts, loose electrode contact, and/or areas of fibrosis in the patient's myocardium. It is important to point out that the low-amplitude areas shown in white in the various velocity vector maps presented herein are not calculated using Green's function or optical flow data processing techniques. Instead, and as described above, these low-amplitude regions or areas may be detected by assessing the relative amplitudes of electrogram signals in step 210.

In the white areas of FIG. 7(*j*), the resulting velocity vector map shows that the active rotors indicated therein are slightly moved closer together than in FIG. 7(*i*), and on the left center side of FIG. 7(*j*) two rotors appearing in FIG. 7(*i*) are revealed as a single active rotor n FIG. 7(*j*). FIGS. 7(*a*) through 7(*j*) show that there are limits to the resolution that can be achieved using a conventional 8×8 array of sensing electrodes in a basket catheter having standard inter-electrode spacing. Thus, higher electrode densities and more recording channels could increase the resolution and accuracy of the results obtained using algorithm or method 200.

After confirming that algorithm or method 200 was capable of detecting complex rotor structures accurately in a patient's myocardium—even in the presence of strong artifacts and noise—algorithm or method 200 was applied to different time portions of the actual patient data shown in FIG. 5(*b*) so as to test further the algorithm's efficacy and accuracy. A velocity vector map corresponding to data acquired between 4,700 milliseconds and 5,100 milliseconds in the original EP recording of FIG. 5(*b*) is shown in FIG. 8(*a*).

Figure 8A:
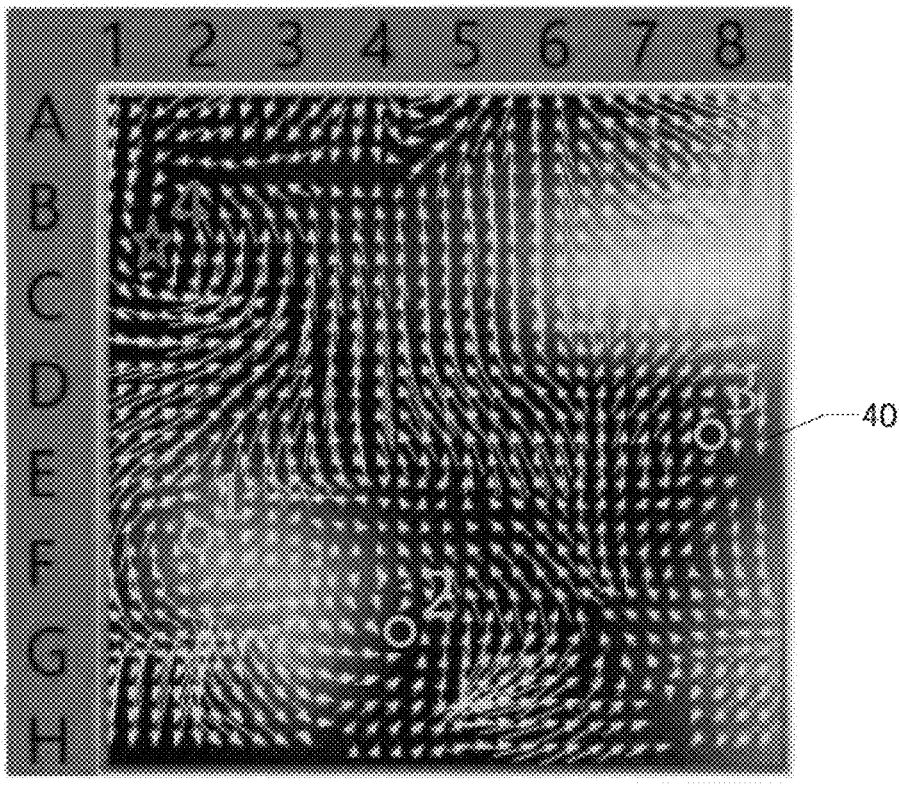
FIGS. 8(a) and 8(b) show velocity vector maps generated from actual patient data using different time windows and of method or algorithm 200.
Figure 8B:
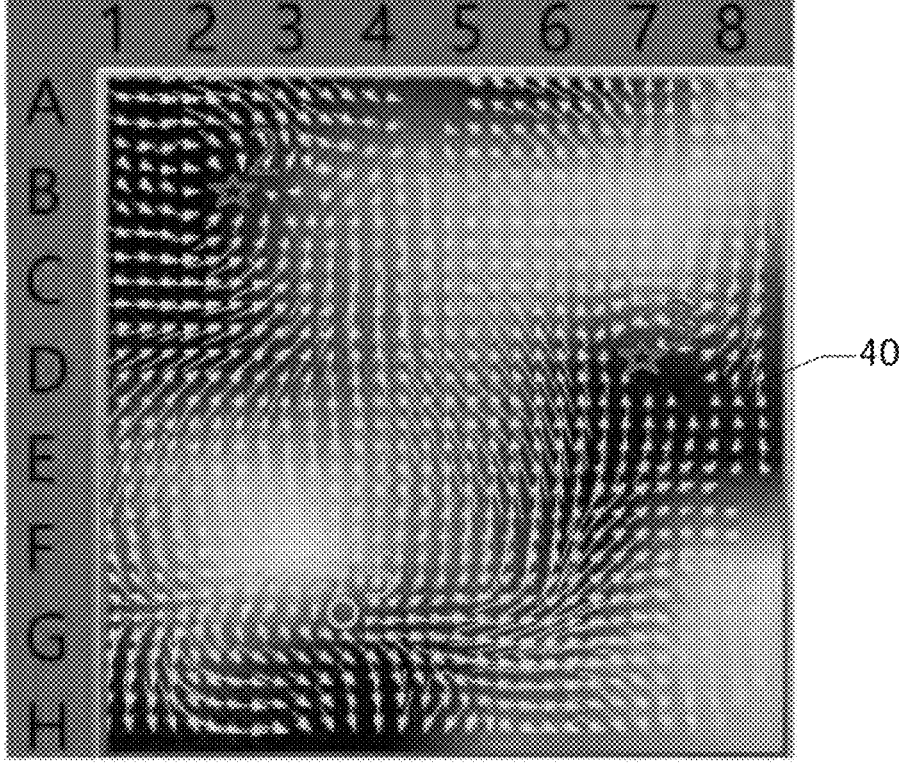

As shown in FIG. 8(*a*), four rotors indicated by circles 1, 2 and 3 and a star 4 were detected. Circles 1 and 2 in FIG. 8(*a*) appear to denote active rotors that are interacting with one another. Circle (3) in FIG. 8(*a*) may be an active rotor, but exhibits some centripetal components. Star 4 in FIG. 8(*a*) clearly corresponds to a passive rotor. Next, a velocity vector map corresponding to the same data set for data acquired between samples 0 seconds and 400 milliseconds was generated, the results of which are shown in FIG. 8(*b*).

Differences between the results shown in FIGS. 8(*a*) and 8(*b*) permit a deeper insight into the true rotor structure of this patient's myocardium, as best shown in FIG. 8(*b*). In the earlier time interval (0 msec. to 400 msec.) of FIG. 8(*b*), the two associated rotors 1 and 2 shown in FIG. 8(*a*) are not yet active, while there is only a single active rotor 5 in FIG. 8(*b*) located between the positions of rotors 1 and 2 shown in FIG. 8(*a*). Rotors 1 and 2 in FIG. 8(*b*) show up at slightly different positions, but now appear clearly as passive rotors representing likely turbulences generated at the border of a mitral valve artifact.

Thus, a health care professional can select differing time windows over which to apply algorithm or method 200 to an EP mapping data set as a means of gaining a better understanding of the behavior of active and passive rotors, fibrotic regions, areas affected by valve defects or artifacts, breakthrough points and areas or defects that are at work in the patient's myocardium. The velocity vector maps generated by algorithm or method 200 permit a health care professional to identify such cardiac rhythm disorders in a patient's myocardium with a degree of precision and accuracy that has heretofore not been possible using conventional EP mapping and intravascular basket or spline catheter devices and methods.

Figure 9:
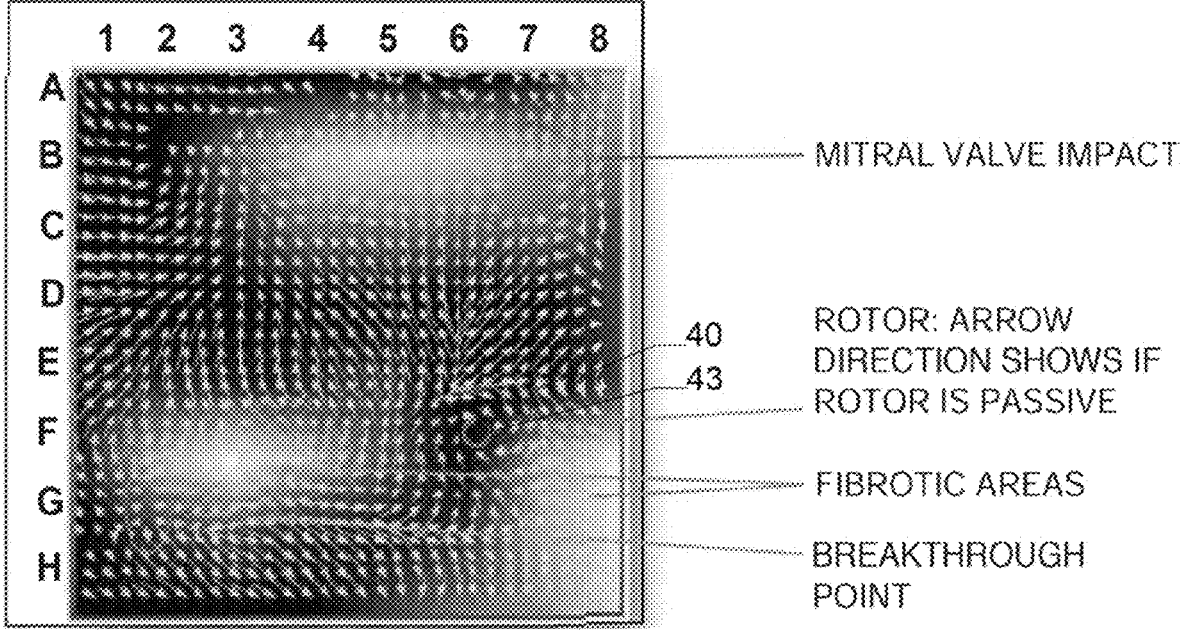
FIG. 9 shows another vector velocity map generated from actual patient data using of method or algorithm 200.
Figure 10A:
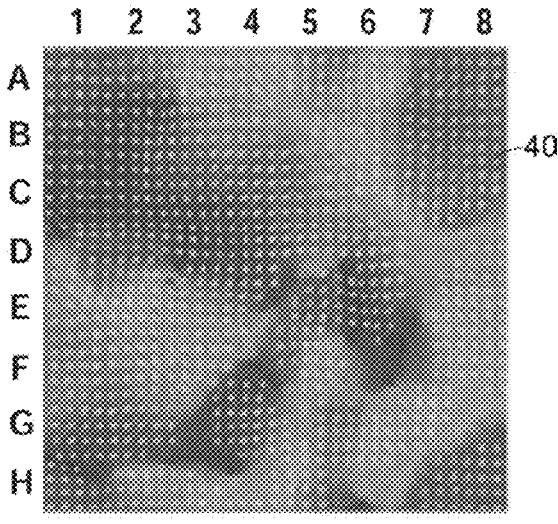
FIGS. 10(a) through 10(d) show further results obtained using actual patient data.
Figure 10B:
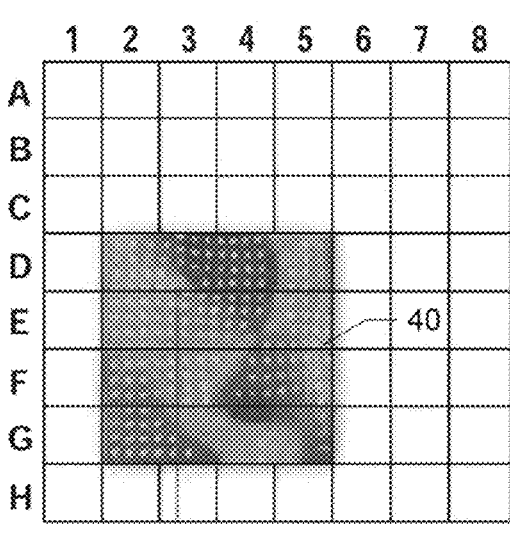
Figure 10C:
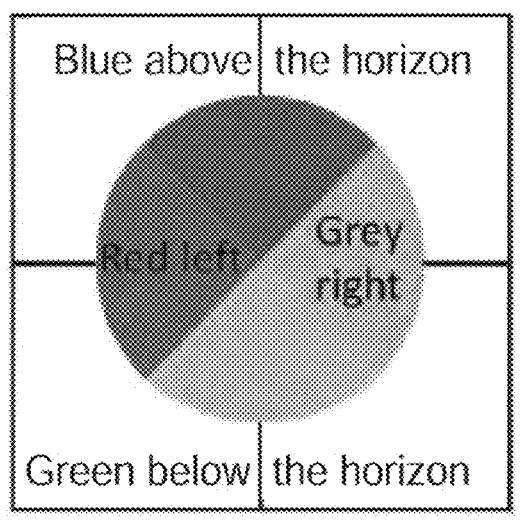
Figure 10D:
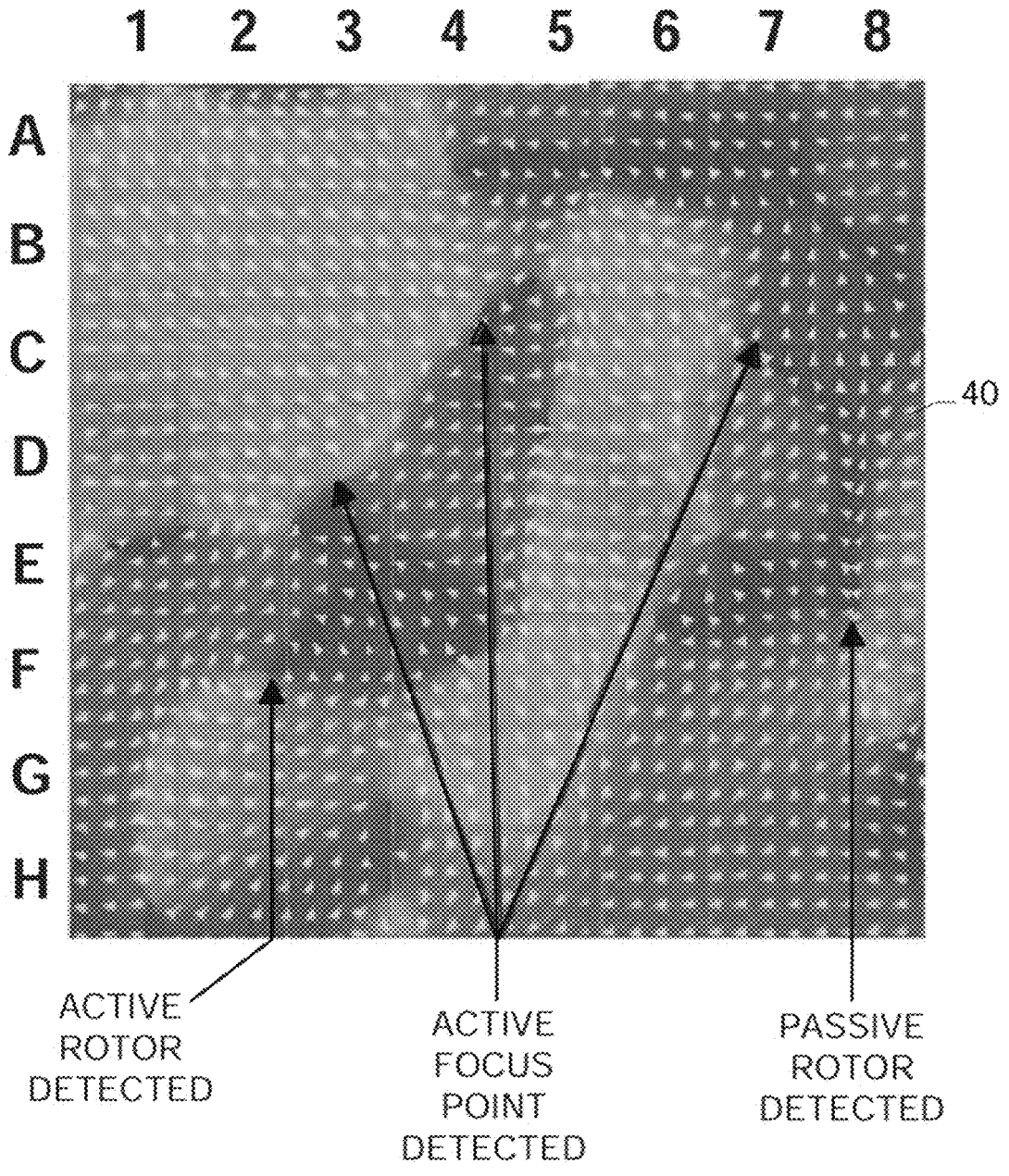

Referring now to FIG. 9, there is shown another example of a vector velocity map generated from actual patient data using algorithm or method 200. In FIG. 9, arrows 40 correspond to action potential wavefront velocity vectors, which as illustrated have differing magnitudes and directions associated herewith. As shown in FIG. 9, various cardiac rhythm defects and disorders become apparent as a result of the generated vector velocity map. The defects and disorders revealed by the vector velocity map of FIG. 9 include an active rotor (where the active rotor propagation direction is indicated in the bottom right of FIG. 9 by green circle 43 rotating in a clockwise or centrifugal direction), a breakthrough point in the bottom left of FIG. 9, fibrotic areas indicted by low-amplitude white areas in the lower portion of FIG. 9, and a mitral valve defect indicted by the white area in the upper portion of FIG. 9.

Referring now to FIGS. 10(*a*) through 10(*d*), there are shown further results obtained using the actual patient data. The raw data corresponding to FIGS. 10(*a*) through 10(*d*) were acquired from a single patient's right atrium using a 64-electrode basket catheter and corresponding EP mapping/recording system. Data were acquired at a 1 millisecond rate over a time period of 60 seconds in all 64 channels. FIGS. 10(*a*) and 10(*b*) correspond to one selected 2 second time window, and FIG. 10(*d*) corresponds to another time window from the same data set. FIG. 10(*d*) shows the color-schemes employed in FIGS. 10(*a*), 10(*b*), and 10(*d*).

The vector velocity map of FIG. 10(*a*) generated using algorithm or method 200 clearly reveals an active rotor located at chess board position D/E, 2/3. The vector velocity map of FIG. 10(*b*) was also generated using algorithm or method 200, but using data acquired from only 16 electrodes in grid D-G, 2-5. As shown in FIG. 10(*b*), the active rotor evident in FIG. 10(*a*) is nearly equally evident in FIG. 10(*b*) despite the significantly more sparse data grid employed to produce the velocity vector map. These remarkable results obtained using a sparse electrode grid are due in large part to the robustness, stability and accuracy of algorithm or method 200, as it has been applied to electrographical flow problems.

FIG. 10(*d*) shows another example of results obtained using algorithm 200 and EP mapping data obtained from the same patient as in FIGS. 10(*a*) and 10(*b*), but over a different time window. Note also that FIG. 10(*d*) shows that algorithm or method 200 has successfully detected one active rotor (at chess board location F2/3), three active focus points, and one passive rotor (at chess board location F8).

It will now be seen that algorithm or method 200 provides not only rotational direction information, but also provides high-resolution spatial information regarding the presence and location of rotors despite the use of sparse electrode grid spacing. Rotors can also move over time in a patient's myocardium, even during the time interval over which EP mapping is being carried out. The increased spatial and temporal resolution of algorithm or method 200 permits such shifts in rotor location to be detected.

In some embodiments, and as described above, multiple or different types of EP mapping and ablation catheters can be used sequentially or at the same time to diagnose and/or treat the patient. For example, a 64-electrode CONSTEL-LATION basket catheter can be used for EP mapping in conjunction with a PENTARAY16- or 20-electrode EP mapping catheter, where the PENTARAY EP mapping catheter is used to zero in on, and provide fine detail regarding, a particular region of the patient's myocardium that the basket catheter has revealed as the location of a source of a cardiac rhythm disorder or irregularity. In addition, catheter 110 or any other EP mapping catheter used in system 100 may be configured to provide ablation therapy (in addition to EP mapping functionality). The various catheters employed in system 100 may also include navigation elements, coils, markers and/or electrodes so that the precise positions of the sensing, pacing and/or ablation electrodes inside the patient's heart 10 are known. Navigational data can be employed by computer 300 in algorithm or method 200 to provide enhanced estimates of the locations of the electrodes in the representations, maps or grids generated thereby, which in turn increases the accuracy and efficacy of the resulting velocity vector maps generated in algorithm or method 200.

In another embodiment, computing device/system 300 is operably connected to a storage medium such as a hard drive or non-volatile memory located in, or operably connected to, data acquisition device 140, where computing device 300 is configured to trigger an external switch operably connected to data acquisition device 140 which permits the upload of conditioned electrogram signal data from data acquisition device 140 to computing device 300.

According to such a configuration, computing device 300 and data acquisition device 140 can remain galvanically isolated from one another, and the need to physically swap USB memory sticks between data acquisition device 140 and computing device 300 is eliminated. This, in turn, permits system 100 to operate more efficiently and quickly, and to provide vector velocity maps to the health care professional in near-real-time while the EP mapping procedure is being carried out within the patient's heart 10.

In some embodiments, in algorithm or method 200 electrogram signals and processed data may be delivered or communicated to system 100, e.g., via a data carrier, after they have been acquired by the electrodes and stored for later processing. The various steps recited in the claims, and the sub-steps recited in each step, need not necessarily be carried out in the precise order in which they are recited.

Now described and disclosed are some examples of the differential kinetic behavior of atrial fibrillation (AF) drivers and triggers, as revealed by selected embodiments of Electrographic Flow (EGF™) mapping, systems, devices, components and methods corresponding to which are described and disclosed herein. Briefly, various examples and embodiments of systems, devices, components and methods configured to detect a location of a source of at least one cardiac rhythm disorder in a patient's heart, and to classify same, are disclosed and described below. Velocity vector maps reveal the location of the source of the at least one cardiac rhythm disorder in the patient's heart, which may be, by way of example, an active rotor in the patient's myocardium and atrium. The resulting velocity vector map may be further processed and/or analyzed to classify the nature of the patient's cardiac rhythm disorder, e.g., as Type A, B or C atrial fibrillation. The resulting cardiac rhythm classification then can be used to determine the optimal, most efficacious and/or most economic treatment or surgical procedure that should be provided to the individual patient.

AF is the most common tachyarrhythmia worldwide, and its prevalence in the general population rises with increasing age, ranging from 0.7% in the age group 55-59 years to 17.8% in those older than 85 years. See, for example, R. H. Falk, Atrial fibrillation. N Engl J Med. 344, 1067-1078 (2001), and J. Heeringa, D. A. van der Kuip, A. Hofman, J. A. Kors, G. van Herpen, B. H. Stricker, T. Stijnen, G. Y. Lip, J. C. Witteman. Prevalence, incidence and lifetime risk of atrial fibrillation: the Rotterdam study. Eur Heart J. 27, 949-953 (2006).

AF causes substantial increase in morbidity and mortality and is a considerable financial burden on the healthcare system. See E. J. Benjamin, P. A. Wolf, R. B. D'Agostino, H. Silbershatz, W. B. Kannel, D. Levy, Impact of atrial fibrillation on the risk of death: the Framingham Heart Study. Circulation. 98.946-52 (1998), and S. S. Chugh, R. Havmoeller, K. Narayanan, D. Singh, M. Rienstra, E. J. Benjamin, R. F. Gillum, Y. H. Kim, J. H. McAnulty, Z. J. Zheng, M. H. Forouzanfar, M. Naghavi, G. A. Mensah, M. Ezzati, C. J. Murray. Worldwide epidemiology of atrial fibrillation: a Global Burden of Disease 2010 Study. Circulation. 129, 837-847 (2014).

While pulmonary vein ectopy as a trigger for paroxysmal atrial AF is well understood, the mechanism by which persistent AF is perpetuated remains unclear, with ongoing debate as to the prevalence and nature of AF drivers such as rotors or focal impulse. See, for example, R. A. Gray, A. M. Pertsov, J. Jalife. Spatial and temporal organization during cardiac fibrillation. Nature. 392, 75-78 (1998), and M. S. Guillem, A. M. Climent, M. Rodrígo, F. Fernández-Avilés, F. Atienza, O. Berenfeld. Presence and stability of rotors in atrial fibrillation: evidence and therapeutic implications. Cardiovasc Res. 109, 480-549 (2016). J. Seitz, C. Bars, G. Théodore, S. Beurtheret, N. Lellouche, M. Bremondy, A. Ferracci, J. Faure, G. Penaranda, M. Yamazaki, U. M. Avula, L. Curel, S. Siame, O. Berenfeld, A. Pisapia, J. Kalifa. AF Ablation Guided by Spatiotemporal Electrogram Dispersion Without Pulmonary Vein isolation: A Wholly Patient-Tailored Approach. J Am Coll Cardiol. 69, 303-321 (2017). J. M. Miller, V. Kaira, M. K. Das, R. Jain, J. B. Garlie, J. A. Brewster, G. Dandamudi. Clinical Benefit of Ablating Localized Sources for Human Atrial Fibrillation: The Indiana University FIRM Registry. J Am Coll Cardiol. 69, 1247-1256 (2017). H. S. Lim, M. Hocini, R. Dubois, A. Denis, N. Derval, S. Zellerhoff, S. Yamashita, B. Berte, S. Mahida, Y. Komatsu, M. Daly, L. Jesel, C. Pomier, V. Meillet, S. Amraoui, A. J. Shah, H. Cochet, F. Sacher, P. Jaïs, M. Haïssaguerre, Complexity and Distribution of Drivers in Relation to Duration of Persistent Atrial Fibrillation. J Am Coll Cardiol. 69, 1257-1269 (2017). M. Yamazaki, D. Filgueiras-Rama, O. Berenfeld, J. Kalifa. Ectopic and reentrant activation patterns in the posterior left atrium during stretch-related atrial fibrillation. Prog Biophys Mol Biol. 110, 269-277 (2012). S. Lee, J. Sahadevan, C. M. Khrestian, I. Cakulev, A. Markowitz, A. L. Waldo. Simultaneous Biatrial High-Density (510-512 Electrodes) Epicardial Mapping of Persistent and Long-Standing Persistent Atrial Fibrillation in Patients: New Insights Into the Mechanism of Its Maintenance. Circulation. 132, 2108-2117 (2015). S. M. Narayan, D. E. Krummen, K. Shivkumar, P. Clopton, W. J. Rappel, J. M. Miller. Treatment of atrial fibrillation by the ablation of localized sources: CONFIRM (Conventional Ablation for Atrial Fibrillation With or Without Focal Impulse and Rotor Modulation) trial. J Am Coll Cardiol. 60, 628-636 (2012). M. Haissaguerre, M. Hocini, A. Denis, A. J. Shah, Y. Komatsu, S. Yamashita, M. Daly, S. Amraoui, S. Zellerhoff, M. Q. Picat, A. Quotb, L. Jesel, H. Lim, S. Ploux, P. Bordachar, G. Attuel, V. Meillet, P. Ritter, N. Derval, F. Sacher, O. Bemus, H. Cochet, P. Jais, R. Dubois. Driver domains in persistent atrial fibrillation. Circulation. 130, 530-538 (2014).

EGF mapping is a novel technique of spatial and temporal reconstruction of electrographic potentials for in vivo characterization and continuous monitoring of AF sources. Among 20 persistent AF patients, more than half showed stable AF sources monitored for up to several hours. Most of these stable sources were not dominantly driving AF but showed a continuous On-Off switching behavior on a time scale of seconds. In the Off-interval, AF continued with virtually unchanged EGF patterns indicating that these sources are not perpetuating AF but rather play a trigger role by reinitiating AF like pulmonary vein sources in paroxysmal AF. Thus, long-term monitoring and characterization of AF sources using EGF mapping techniques permits better understand of the role AF sources play, and may help optimize subsequently-employed ablation strategies.

Referring now to FIGS. 11-14, data are shown that illustrate the quick and efficient classification of patients' heart conditions that are made possible using the ABLAMAP™ Electrographic Flow (EGF™) mapping techniques of ABLACON™ Inc., of Calistoga, CA, USA. These EGF techniques allow accurate in vivo characterization, continuous monitoring, and classification of the behavior of AF drivers in human atria, and can be performed using either extracorporeal or intracardiac electrocardiographic sensing techniques, or a combination of extracorporeal and intracardiac electrocardiographic sensing techniques.

EGF mapping is the first method that allows detailed characterization, classification, and long-term monitoring of the behavior of AF sources in human atria (see, for example, the above-referenced '1273 patent application). EGF mapping represents a full spatial and temporal reconstruction of electrographic potentials and their flow derived from endocardial unipolar electrogram data acquired using, in this particular non-limiting example, a 64-pole basket catheter (see, e.g., the '1273 patent application). In two-second EGF maps, excitation sources appear as quadri-point centers, where the four colors indicating flow direction (red=left, black=right, green=down and blue=up) adjoin and where the arrows indicating excitation velocity originate in all directions.

The data and results shown in FIGS. 11-14 were obtained from patients having persistent symptomatic, drug-refractory AF who underwent PVI. In all the patients, focal impulse and rotor modulation (FIRM) of the right and left atrium using the RhythmViewe System Version 5 (Fa. Abbott, USA) was performed, in addition to circumferential PVI using radiofrequency ablation. Epochal data from the patients were analyzed using the ABLAMAP™ System of ABLACON™ Inc., of Wheat Ridge, Colorado after the procedures had been performed. The working hypothesis was that the Ablamap system would identify and discriminate between active and passive AF drivers, and reveal focal impulse or rotational activity.

The EGF methodology employed in the study was as follows. Electrogram data traces of 60 seconds were used and low-pass filtered (4-pole Bessel) at 5 Hz, and an average of all 64 traces was subtracted from each trace to remove simple artefacts. For each far field artefact detected, a time interval of 250 ms starting at two samples before the time point of detection was cut out from the final analysis.

Next the Ablamap system was used to perform further data reduction by normalizing the amplitude value of each sample with respect to the plus/minus 4 times standard deviation amplitude range of the 400 next samples and by subsequently averaging 19 of those normalized consecutive samples to yield one so-called frame. Filtered, normalized and averaged data were stored as 8-bit 8×8 matrix frames comprising each a 19 ms time interval of recording. For far field artefacts the last frame before the artefact was repeated in the analysis 13-fold to cover the time frame of the artefact.

Proof of concept was performed in one patient having a sinus rhythm showing a focal impulse from the sinus node region that was visualized and confirmed using EGF techniques. Although both active and passive drivers could be discriminated using EGF, only active drivers were investigated for the characterization of the temporo-spatial behavior of AF drivers.

Previously, wavefronts emanating from foci and breakthrough sites identified during optical mapping or short episodes of epicardial mapping were thought to be indicative of persistent AF. Due to clinical tools having limitations in visualization and long-term analysis of AF drivers, it was thought that shorter periods for driver analysis might result in limited spatio-temporal differentiation, Consequently, it was believed that EGF might contribute to a deeper understanding of how AF drivers actually work, and therefore lead to better or more optimized ablation strategies.

Referring again to FIGS. 11-14, EGF maps were obtained in the atria of the patients, while AF ablation was performed. All patients were experiencing ongoing persistent AF. In only a few atria, EGF mapping showed a continuously active single driver (Type A) as shown in panel A of FIG. 11 (RA), Panel A of FIG. 12 (LA), and Panel A of FIG. 13 (three focal impulse sources and two rotors). In more atria, multiple AF sources formed a spatially stable pattern (Type B, Panels B in FIGS. 11 and 12). In the remaining atria (RA and LA), excitation originated from variable patterns of sources with varying rotational and non-rotational activity (Type C, Panel C in FIG. 1, Panel C in FIG. 12, and Panel A in FIG. 13).

Figure 12:
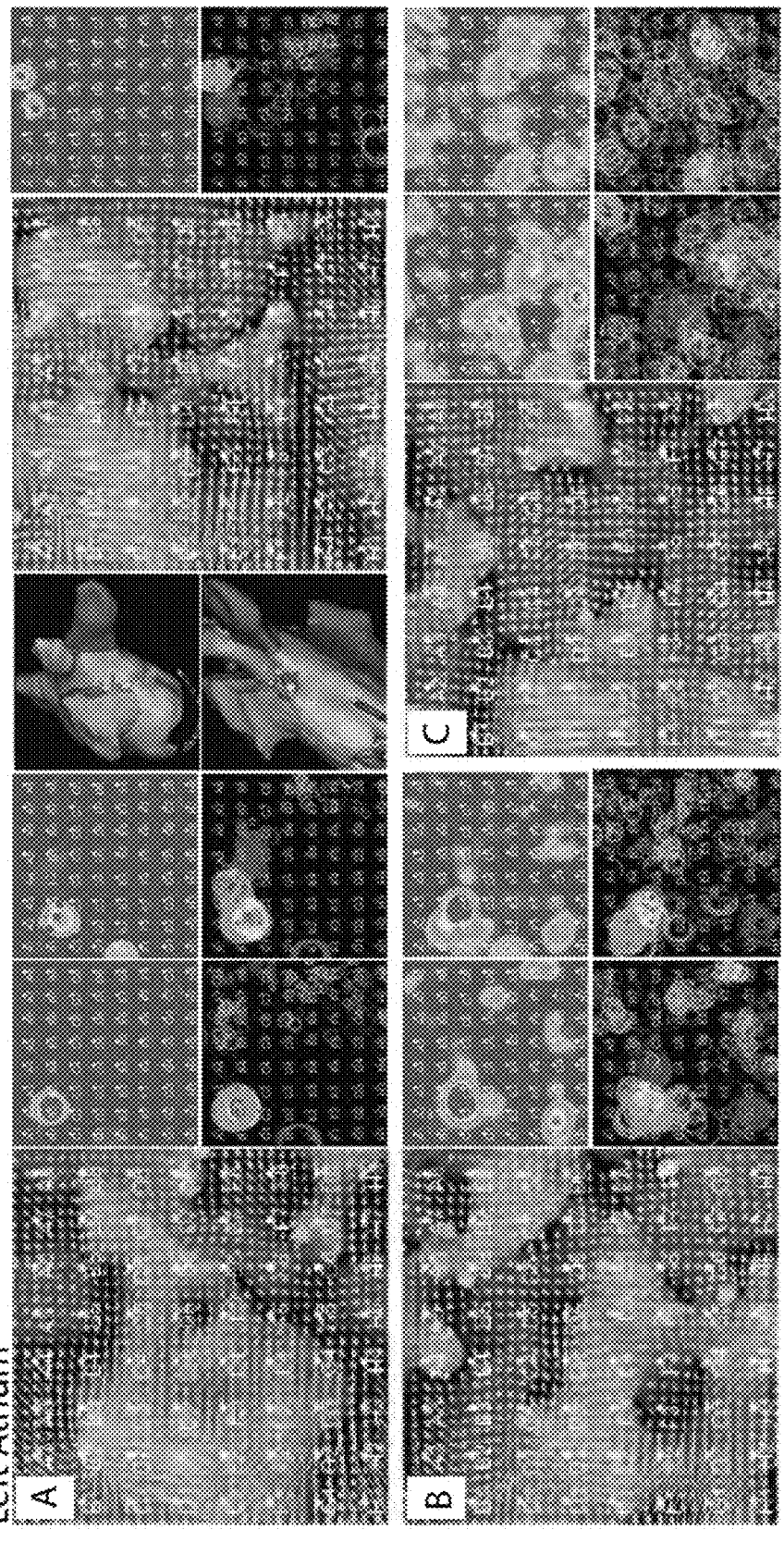

Panel A in FIG. 12 shows the long-term behavior of a Type A driver (clockwise rotor, yellow spot with green border) located at electrode B2 between the upper left pulmonary vein and the left atrial appendage at the start of a pulmonary vein isolation (PVI) procedure, which was found largely unchanged after 20 mins. However, 1 h and 10 mins later, after PVI using RF ablation was performed, which included ablation at the location of this driver, the B2 clockwise rotor disappeared and was replaced by a doublet rotor having clockwise and counter-clockwise rotation appearing at locations A4 and A6 near the PVI line below the left pulmonary veins, suggesting that the RF ablation led to the rotor's modification.

Figure 13:
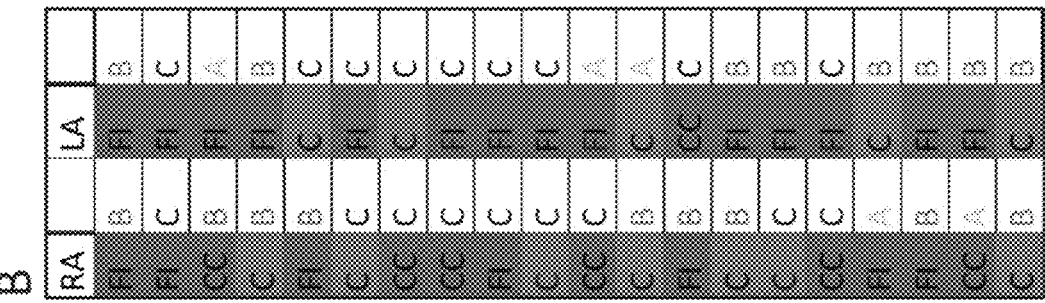

Panel B in FIG. 13 plots the prevalence in two-second EGF maps (temporal stability in percent) of the most prominent sources in an initial one-minute recording in an atrium versus the spatial stability between two one-minute recordings having intervals of 10 to 20 mins. The obtained results scatter in a wide spectrum between the left upper dot that shows 100% temporal stability (being constantly detectable during the one-minute recording) and spatial stability below 0.2 (spatial change of the center of the driver in electrode intervals). The lower right dot was visible during only 10% of the one-minute recording while showing a displacement of about 4 (half of the basket catheter size) in between the two recordings.

Figure 14:
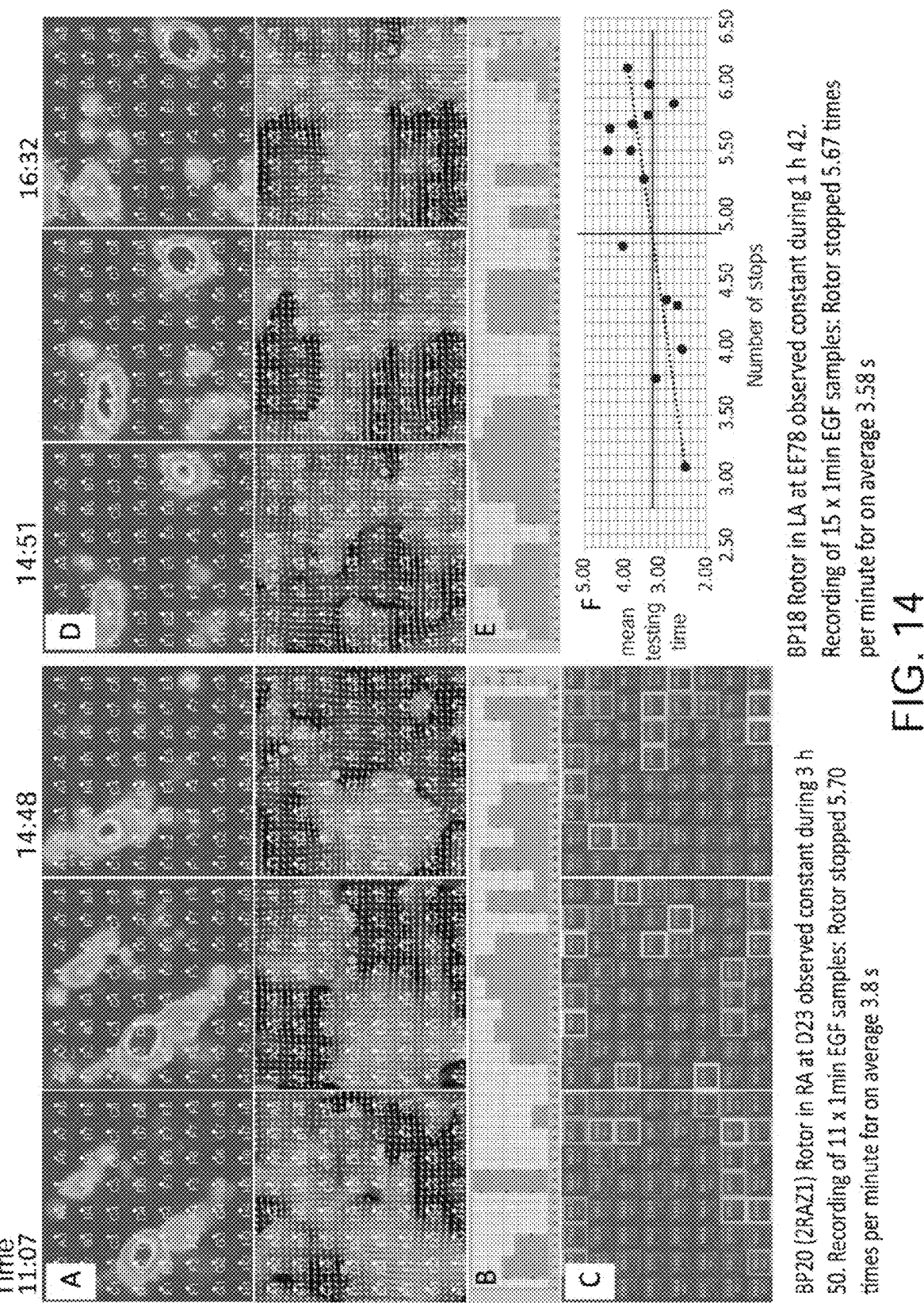

The absence of an expected strong correlation between temporal stability during a one-minute recording and the spatial stability of the pattern during a several minute recording suggests an additional kinetic behavior modulating the activity of the sources. Such behavior is shown in FIG. 14, where there are two examples of Type B atria with spatially stable driver patterns, where one atrium was observed over a period of more than three hours and another atrium was observed over a period of almost two hours. In these two atria, as in all Type B cases, an unexpected On-Off switching behavior was observed. Type B rotors were on average switched Off 4.95±0.98 times during one minute for an average period of 3.38±0.67 seconds (n=16 sources from 9 patients). In other words, Type B rotors are not present for about one third of the time as shown in Panels B and F in FIG. 14.

As demonstrated in Panels B and F in FIG. 14, the overall AF pattern stays largely unchanged during these Off-periods, indicating that these spatially stable Type B sources are not mandatory to maintain AF. This observation is further supported by the dominant frequency maps shown in Panel D of FIG. 14. While the Off-switching of the driver at C2 is clearly visible by a change from 160 to 270 ms and back in the On period 3:50 hours later, other positions such as at location E5 are constantly on at a high frequency with a periodicity of 150 ms. This suggests that sources like C2 in FIG. 14 may be triggers reinitiating AF, while perpetuation of persistent AF in type B atria seems to be due to unstable source patterns such as those shown in FIG. 12.

A clear explanation as to why On-Off switching occurs remains uncertain. The positive correlation (Panel F in FIG. 14) between the mean resting time (related to an assumed activation rate constant) and the number of stops or Off periods per minute (displaying the inactivation rate) could suggest metabolic fatigue, autonomous ganglia influence, or competitive interference with unstable sources as mechanisms underlying the observed On-Off behavior.

Figure 11:
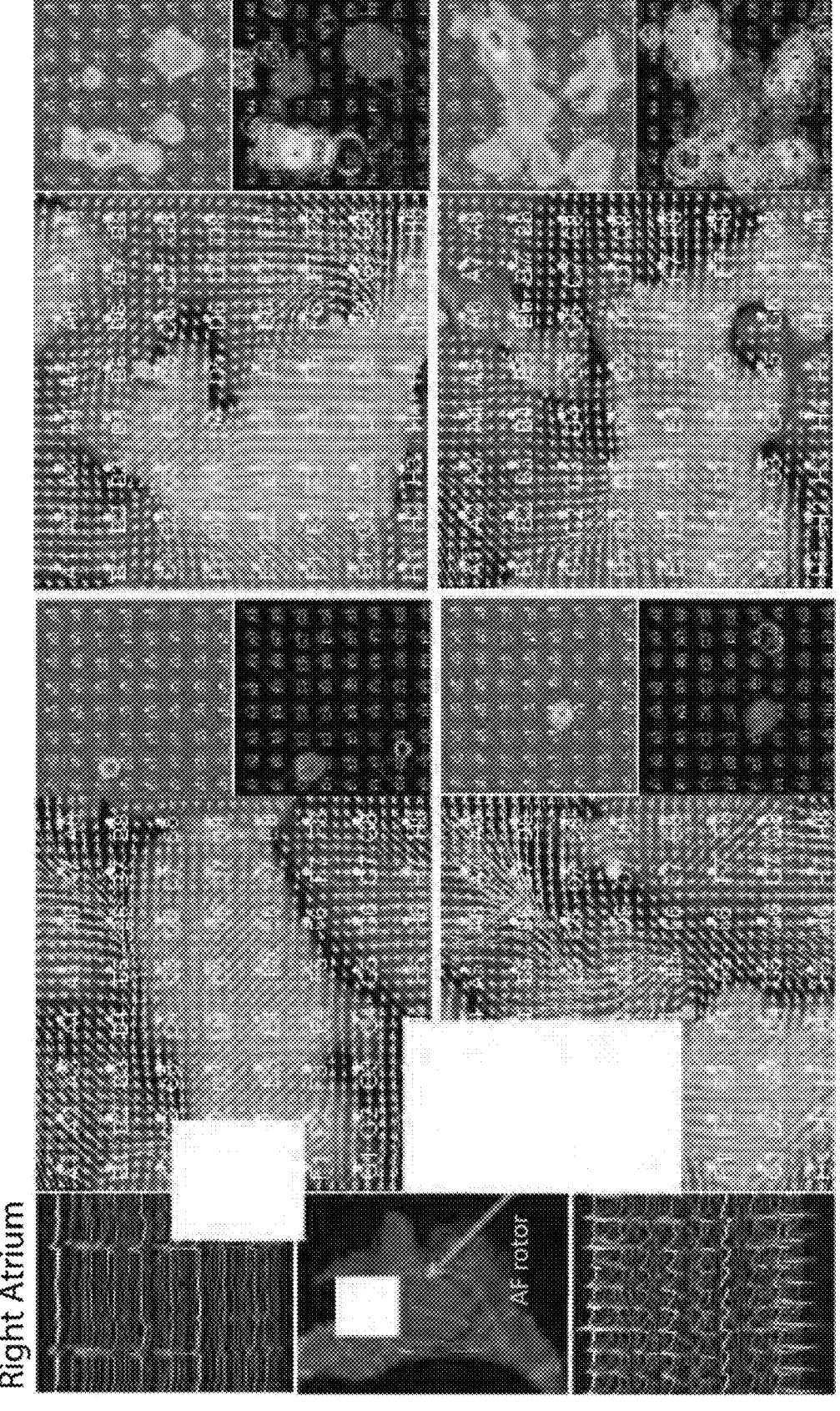
FIGS. 11-14 illustrate classification of patients' heart conditions using electrographic flow mapping techniques.

Continuing to refer to FIGS. 11-14, in Panel A of FIG. 11 there are shown EGF data from the right atrium (RA). Two-second EGF maps are shown of normal sinus rhythm (SR) (left upper display of Panel A) and AF (left lower display of Panel A), both recorded using a 64-pole basket catheter (see the left center display of Panel A and the middle displays of Panel A), after and before electrical cardioversion. The colors in FIG. 11 indicate the direction of electrographic flow (red=left, blue=up, black=right and green=down); arrows indicate relative velocity. Yellow spots indicate the position of a source where arrows propagate in all directions. Sinoatrial node break-through is seen to occur at C2 (see the upper central display of Panel A), while a stable counter-clockwise turning rotor is seen to occur in the lower central display of Panel A. A one-minute recording aimed at detecting the prevalence of the sinoatrial node endocardial break-through point (upper right blue display of Panel A) and its representation as a focal impulse (FI=red circles in upper right black display of Panel A) is also shown. The same one-minute recording of AF shows a single rotational source in the lower right blue display of Panel A, and its counter-clockwise orientation (see the blue circles in the lower right black display of Panel A).

In Panel B of FIG. 11, there is shown a two-second EGF recording in the RA of a typical patient with a spatially stable source pattern (left display of Panel B in FIG. 11). One-minute recordings show a stable distinct source pattern (upper right display of Panel B in FIG. 11) with constant turning behavior (lower right display of Panel B in FIG. 11). In Panel C of FIG. 11, there is shown a two-second EGF recording in the RA from a typical patient with an unstable source pattern (left display of Panel C in FIG. 11). One-minute recordings show a chaotic source pattern (upper right display of Panel C in FIG. 11) with variable turning behavior (lower right display of Panel C in FIG. 11).

Referring now to FIG. 12, there are shown further EGF results from the left atrium (LA). The small second and third center-left displays of Panel A show initial two-second EGF maps with a single source having clockwise rotation in a persistent AF patient. One-minute recordings taken at 20-minute intervals show the stability of the single source at location B2 (see small second and third upper center displays of Panel A) having clockwise rotation (see small second and third lower center displays of Panel A). The location of a basket catheter in the left atrium places electrode B2 between the left atrial appendage and the left upper pulmonary vein in a typical PVI line (see fourth center upper display in Panel A). Dots indicate PVI was performed by RF ablation (see fourth center lower display in Panel A). A two-second EGF image demonstrates a changed pattern after PVI (see the fifth display from the left in Panel A). Here, the original source at B2 is no longer present, while two slightly weaker rotational activities are noted near location A5 (see the right-most upper display in Panel A), which also exhibit different rotational orientations (see the right-most lower display in Panel A).

Continuing to refer to FIG. 12, in Panel B there are shown 2 second EGF recordings taken from the LA of a typical patient having a stable source pattern (see the left-most display of Panel B). Initial one minute and 10-minute recordings (left to right in Panel B) show a stable distinct source pattern (upper right display of Panel B) with constant turning behavior (lower right display of Panel B). In Panel C of FIG. 12 there are shown 2 second EGF recordings from the LA of a typical patient with unstable source patterns (see left display of Panel C). Initial one minute and 10-minute recordings (left to right in Panel C) show a chaotic source pattern (upper right display of Panel C) with variable turning behavior (lower right display of Panel C).

In FIG. 13 there are shown EGF statistics from persistent AF patients. Panel A of FIG. 13 shows the temporal and spatial stability of sources. For each atrium, the behavior of the initial strongest source is shown. Temporal stability is represented by the percentage of the 2 second time segments in which drivers were found to be active during one minute. Spatial stability is measured by the spatial distance in electrode distance units that the source has been dislocated between two one-minute recordings (recorded with a time interval of 10 to 20 minutes). As shown in FIG. 13, RA and LA data are scattered fairly evenly. The data can be classified into three types: Type A=high spatial stability (dislocation <1 electrode distance) and high temporal stability >33% prevalence; Type B=high spatial stability and low temporal stability, and Type C=low temporal and spatial stability.

Panel B of FIG. 13 shows source orientation and stability type in right and left atria. Some RA display FI, other RA display rotational characteristics, and still other LA display FI (while only a few show rotational characteristics). Types A, B and C show no preference for certain rotational behaviors. RA and LA of one and the same patient are typically either only spatially stable (type A and type B), or unstable (type C). Only a few of the patients showed differential spatial stability of RA and LA, Even fewer patients were borderline unstable with 1.1 and 1.4 electrode distance dislocations.

Panel C of FIG. 13 shows the distribution of spatially stable AF sources (types A and B) within regions of the RA and LA in the analysis. Red dots show focal impulse and turquoise dots show rotors of the leading source (the source with the highest prevalence value) of each atrium labeled for type of kinetics (Type SA or Type B). Additional stable sources in the same atria with lower prevalence values are indicated as circles; red (focal impulse) and turquoise (rotors).

FIG. 14 shows long-term stable sources displaying On-Off behavior on a time scale of seconds. In Panel A, one-minute EGF recordings in the RA from a persistent AF patient are shown, initially (left upper display in Panel A), after 10 minutes (middle upper display in Panel A) and after 3 and ½ hours (right upper display in Panel A), which reveals a constant presence of a leading clockwise rotating driver. Some 2 second EGF images show a very similar pattern initially (left lower display in Panel A) and after 3 and ½ hours (right lower display in Panel A). In many 2 second EGF recordings, the leading driver is not visible, while the overall EGF pattern is virtually unchanged (see middle lower display of Panel A), indicating that AF is not maintained by the driver presence.

Panel B of FIG. 14 shows temporal On-Off patterns during one-minute EGF recordings. Each bar represents the presence of the leading driver at D2 of the initial minute of recording 2 second segments. The biggest bars represent the largest prevalence of the driver signal in a 2 second segment, while empty bars indicate that the driver was being detected with a prevalence of less than 10% of the maximum prevalence during the recorded time segment. For each time segment, the EGF algorithm ran 110 tests for driver presence during two seconds. In most recordings, the large bars represent a detection rate above 100, while empty columns usually represent small numbers below 10. The leading driver analyzed here showed six Off intervals between 2 and 4 seconds in duration. An empty column at the end, at the beginning or both were equally counted as one Off interval. Because of the 2 second lengths of individual segments, stops shorter than 2 seconds were not resolved.

Referring now to Panel C of FIG. 14, there are shown frequency maps representing On- and Off-states during an initial minute of recording, and recording after 3 and ½ hours. Frequency values were determined by calculating a Fourier spectrum from a 2 second signal generated by subtracting the signals of two neighboring electrodes for a given location (thereby simulating bipolar recording). Peak frequencies were calculated as the highest frequency of the respective spectrum above a given threshold equal for all time segments compared. The frequency values are very similar in all three displays of Panel C, except around the location of the On-Off driver switching, giving independent evidence that the fibrillation behavior was not fundamentally changed by switching of the driver, even though the Off state is not only visible in EGF data, but is also visible in the frequency data.

Panel D of FIG. 14 shows one-minute EGF recordings in the LA for initial recordings (left upper display of Panel D), after 10 minutes (middle upper display of Panel D) and after 1 hour and 40 minutes (right upper display of Panel D). The three of displays of Panel D show the constant presence of a leading counter-clockwise rotating driver. Two second EGF images again show a very similar pattern initially (left lower display of Panel D) and after 1 hour and 40 minutes (right lower display of Panel D). In many 2 second EGF recordings of Panel D, the leading driver is not visible, but the overall EGF pattern remains virtually unchanged (see middle lower display of Panel D), indicating that AF is not maintained by the driver presence.

Panel E of FIG. 14 shows a temporal On-Off pattern during one-minute recordings corresponding to Panel D, and the correlation between mean resting time and number of stops, and shows that those sources which go to sleep more often tend also to sleep longer suggesting a mechanism related to fatigue of an underlying energy source.

In accordance with the EGF techniques described and disclosed herein, quick and efficient classification of the particular type of atrial fibrillation from which an individual patient suffers may be made according to Types A, B and C described above. Type A atrial fibrillation is the most common type of AF, and is characterized by stable rotors and drivers, and typically may be treated successfully using standard ablation techniques (e.g., radio frequency or other standard ablation techniques). Type C AF is typically characterized by chaotic atrial behavior, and may often be treated successfully using pulmonary vein isolation (PVI) ablation techniques. Type B AF, often characterized by rotors that switch on and off, is substantially more difficult to diagnose and treat successfully (at least, that is, with respect to prior art techniques). Unlike in the prior art, the EGF techniques described and disclosed herein permit Type B AF to be rapidly diagnosed, and the specific spatial locations within a patient's heart where the Type B rotors are switching on and off to be determined.

Thus, the EGF techniques described and disclosed herein can be used as a first classification step to determine rapidly, efficiently, and accurately the particular type of AF from which a patient suffers. Once the patient's AF type has been classified, the optimal, most efficacious and most economic treatment or surgical procedure for that patient can be selected (e.g., appropriate pharmaceutical drugs, PVI ablation, RF ablation, cryogenic ablation, further or more detailed electrocardiographic mapping in combination with intracardiac ablation, etc.).

As a result, the EGF classification systems and methods described and disclosed herein can be employed both to reduce the cost of treating a patient's AF, and to deliver the most efficacious treatment. The various systems, devices, components and methods described and disclosed herein, such as the EGF techniques described in detail above, may thus be configured for use in either intracardiac electrophysiological mapping applications, external/extracorporeal electrophysiological mapping applications, or in a combination of such internal and external electrophysiological mapping applications.

Referring now to FIGS. 15 through 31, there are shown, described and disclosed various aspects of some embodiments of the ABLAMAP™ atrial fibrillation mapping system.

FIG. 15 shows and describes one embodiment of an ABLAMAP mapping Electrographic Flow (EGF) mapping system, which is configured to permit the identification of AF sources and therapy guidance based on Ablacon's proprietary Electrographic Flow (EGF(D) algorithm technology. The embodiment of the system shown in FIG. 15 includes the following characteristics:

Sub-electrode spatial resolution

Patient classification based on long-term stability maps of AF sources

Distinction between active and passive Rotors, Drivers and Triggers

Continuous quantitative therapy monitoring during ablation, and

A Multi-Core Workstation

Figure 16:
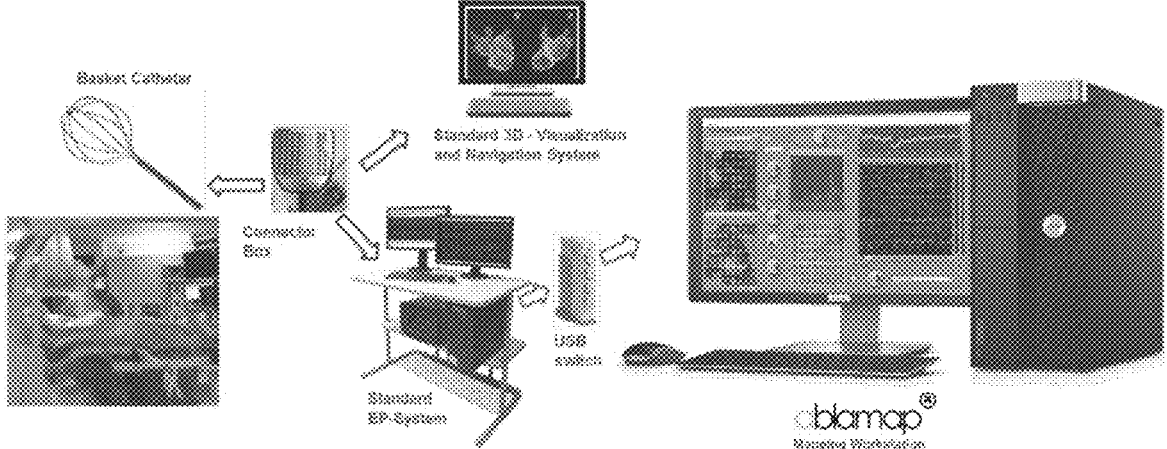

In FIG. 16, there is shown one embodiment of an ABLAMAP mapping Electrographic Flow (EGF) mapping system that is integrated into an EP laboratory (EP-Lab), and which in the disclosed embodiment comprises a basket catheter, a standard Boston Scientific (Bard) LABSYSTEM PRO™ with Navigation and 3D Visualization (Biosense Webster, St. Jude), and an ABLAMAP Mapping Workstation (OEM made by Dell).

FIGS. 17-31 illustrate various additional aspects of, and results obtained using, the ABLAMAP mapping system according to some embodiments.

In FIG. 17, there are described and illustrated the calculation of velocity vectors using optical flow methods according to some embodiments, and in one such embodiment the use of the Horn Schunck method of minimization in iterative optical flow calculations, where a scheme of successive iterations is employed.

Figure 18:
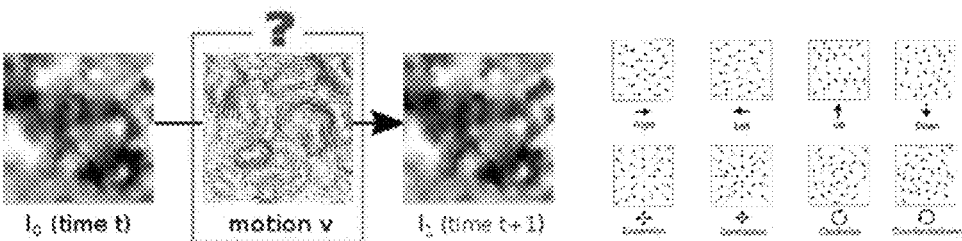

In FIG. 18 there is described one embodiment of a method for determining electrographic flow to recover apparent 2D motion that transforms a first image into a second image. In the illustrative example of FIG. 18, a set of flow vectors is determined that morphs one electrographic voltage profile into the next. An infinite number of solutions is available, and the best morphing appears to occur at minimal total vector amplitudes. Learning is shown to be accomplished in this example over 1.9 seconds worth of samples, where deviations are minimized with respect to previous obtained results.

Figure 19:
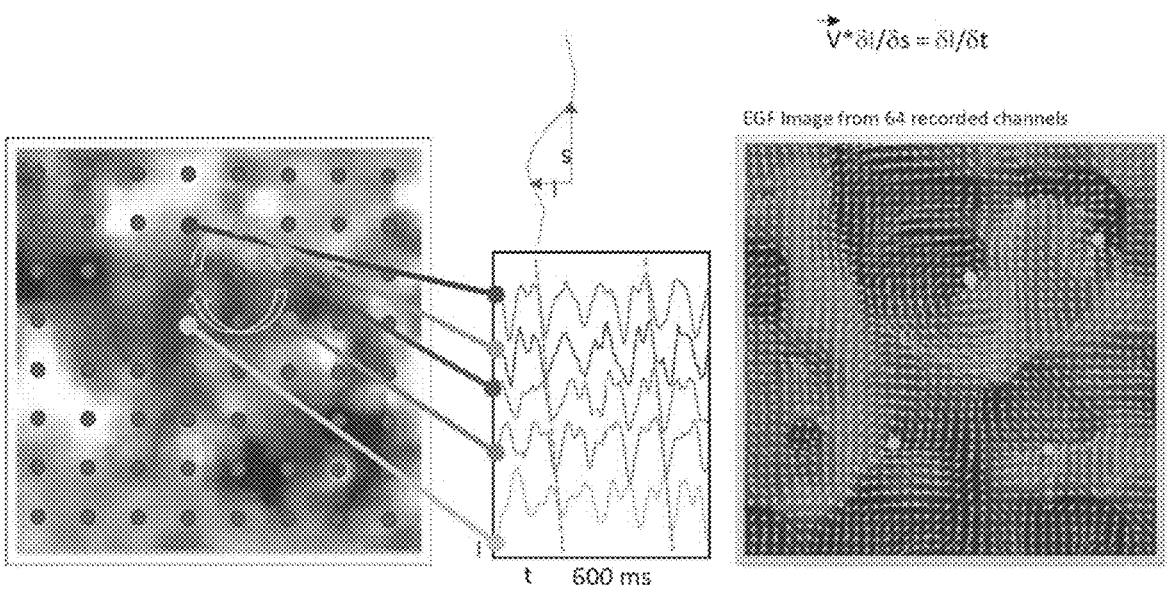

FIG. 19 shows an example of an ABLAMAP EGF solution obtained in a sheep heart, where optical mapping of action potentials was carried out using fluorescent dye, basket catheter data were simulated/generated based on the optical mapping results, and ABLAMAP EGF analysis was performed on the simulated basket catheter data.

FIG. 20 shows and describes another illustrative embodiment of some aspects of a method for ABLAMAP EGF mapping, comprising: (a) acquiring 2 seconds of electrogram data; (b) generating a one or more EGF Maps; (c) analyzing each EGF Map automatically with respect to active sources of EGF, source characteristics (e.g., rotors, focal impulses), and passive rotors; (d) generating 1 minute of EGF Maps (i.e., 29 maps) to yield a prevalence map (in some embodiments, prevalence maps are statistical summaries of EGF behavior occurring over, by way of example, one minute of time), and (e) generating active source maps, where different types of AF sources can be identified, and RF-ablated and ablation outcomes can be confirmed directly.

Figure 23:
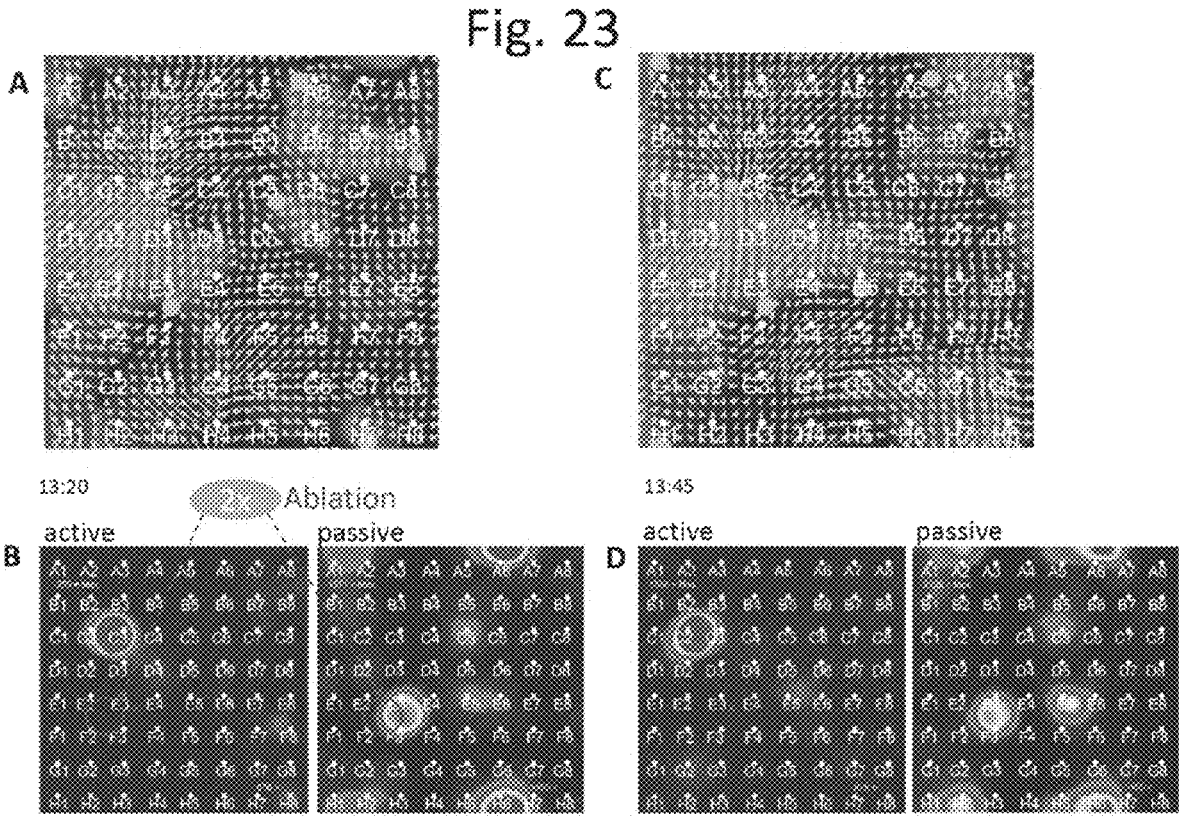

FIGS. 21 through 23 show various examples of ABLAMAP EGF results. FIG. 21 shows examples of EGF techniques employed to discriminate between sinus rhythm and atrial fibrillation (AF). FIG. 22 shows examples of EGF techniques employed to discriminate between active rotors and passive rotors. FIG. 23 shows examples of EGF techniques employed to show how passive rotors can be driven by focal impulses.

A publication presented by Bellmann et al. in 2017, "Electrographic Flow Mapping—A novel technology for endocardial driver identification in patients with persistent atrial fibrillation," a copy of which is filed in an Information Disclosure Statement (IDS) filed on even date herewith in the present patent application, and which is hereby incorporated by reference herein in its entirety, shows and describes various aspects of ABLAMAP EGF mapping. Discrimination between active and passive rotors, and the identification of non-rotational drivers, are discussed, where EGF techniques are employed with a view towards guiding AF ablation therapies that are to be delivered to patients. The objective and aim of the work described in this publication was to analyze changes in EGF during FIRM guided treatment in patients with persistent AF. Patients with persistent symptomatic drug refractory AF were included. In all patients, FIRM of the right and left atria was performed, plus circumferential PVI using radiofrequency ablation in conjunction with a 3D mapping system. Data were obtained using a 64-electrode FIRM mapping catheter. FIRM analysis for guidance of ablation was performed in all patients. In most patients, targets were identified and ablated.

Datasets of these patients were used for FIRM mapping before and after rotor ablation, and then underwent EGF analysis with the ABLAMAP System of ABLACON.

Continuing to refer to this publication, EGF mapping was carried out using the following parameters:

Unipolar electrograms recorded via basket catheter

Reconstruction of voltage shape using Green's minimal energy algorithm. Shapes resemble optical maps obtained with voltage sensitive dyes.

100 consecutive shapes processed to an EGF Map (Horn-Schunck algorithm, no phase mapping)

Each EGF Map was automatically analyzed with respect to active sources of EGF source characteristics (e.g., rotor, focal impulse) and passive rotors. All results were statistically summarized over one-minute intervals.

In the Bellmann publication's lower left corner, there are shown graphs corresponding to sinus rhythm vs AF in the right atrium (RA) of a persistent AF patient before and after cardioversion. Graph A) shows ECGs, and Graph B) shows two-second EGF maps of the sinus (or sine) Rhythm (left upper panel) and AF (left lower panel) recorded from a 64-pole basket catheter The left, middle panel in the lower left-hand corner shows before and after electrical cardioversion results. Colors indicate the direction of electrographic flow (red=left; blue=up; black=right; and green=down). Arrows indicate relative velocity. Sinoatrial node breakthrough is shown at C2 (upper central panel) and a stable counterclockwise turning rotor is shown in the lower central panel.

Still referring to the Bellmann publication, at the bottom central portion thereof, in the second panel from the left, there is shown Graph C), which shows one minute recording of detection prevalence of a sinoatrial node endocardial breakthrough point (upper left blue panel) and its representation as a focal impulse (FI=red circles in right upper black panel). The same one-minute recording in AF shows a single rotational source (lower left blue panel) and its counterclockwise orientation (blue circles in the lower right black panel). Graph D) shows the detail of a passive rotor (driven by flow) at C6 and C7 and an active rotor (which generates flow) at F4. On the right side are shown activation maps of both rotors. No differentiation between active and passive rotors is possible.

Continuing to refer to the Bellmann publication, at the bottom central portion thereof, in the third panel from the left, there are shown the results of unsuccessful ablation of passive rotors: an EGF map of an active FI at C3 in the left atrium of a persistent AF patient Induces a passive rotor at EF3 in Graphs A) and C). In Graph B) there are shown FIRM results with only the rotor at E3/F3 being detectable where ablation was carried out twice over 300 seconds. After 25 minutes, Graph D) shows that the active rotor at C3 is still detectable using EGF techniques (left panel). The passive rotor is now visible at E6 (right panel}. This example shows how important it is to distinguish between active and passive rotors to select the correct ablation target.

Still continuing to refer to the Bellman publication, in the lower right-hand corner thereof, there are shown the results of successful ablation of active sources, where active sources were successfully targeted by ablation. An EGF map of the left atrium exhibiting a counterclockwise rotor at CD23 and an F1 at GH23 is shown in Panel A (the initial situation before ablation). The two ablation target areas are shown by red circles. Panel B shows the results after ablation at sites 1 and 2. As shown, the rotor at CD23 has been eliminated, and the F1 at GH23 has now been shifted towards A2. A new ablation target at AB23 is indicated by FIRM results (not shown). Panel C shows that the F1 at is A2 still visible but much less active.

The results presented in the Bellman publication and described herein are that AF drivers were identified with EGF, were correlated with rotors identified on the FIRM maps, and EGF permitted differentiation between active and passive rotors, as well as between non-rotational AF drivers. Some of the rotors identified by FIRM mapping might be only passive according to results provided by EGF. Furthermore, EGF allowed monitoring of the stability of AF drivers over several minutes. In conclusion, valuable additional information is obtained using EGF techniques during endocardial AF driver analysis. Discrimination between active and passive rotors and non-rotational drivers by EGF can help optimize the guidance of AF ablation therapy. Long term stability of rotors may help to identify critical AF targets.

For further related information, see Bellmann et al. "Identification of active atrial fibrillation sources from passive rotors using electrographical flow mapping," Clinical research in Cardiology, 2018, November; 107(11):1021-1032, a copy of which is filed in an Information Disclosure Statement (IDS) filed on even date herewith in the present patent application, and which is hereby incorporated by reference herein in its entirety.

Figure 24:
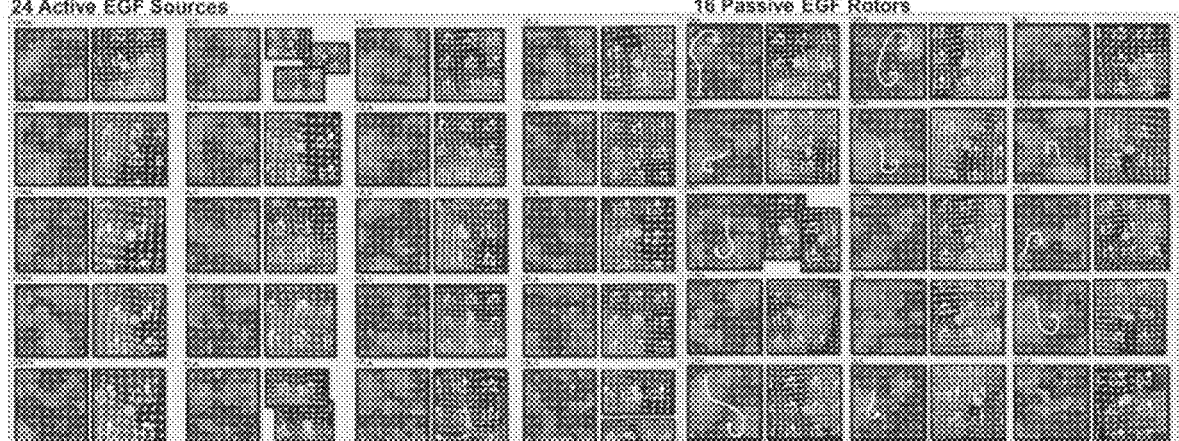

FIG. 24 shows the results of comparing FIRM and EGF results, where active and passive sources are discriminated from one another.

Figure 25:
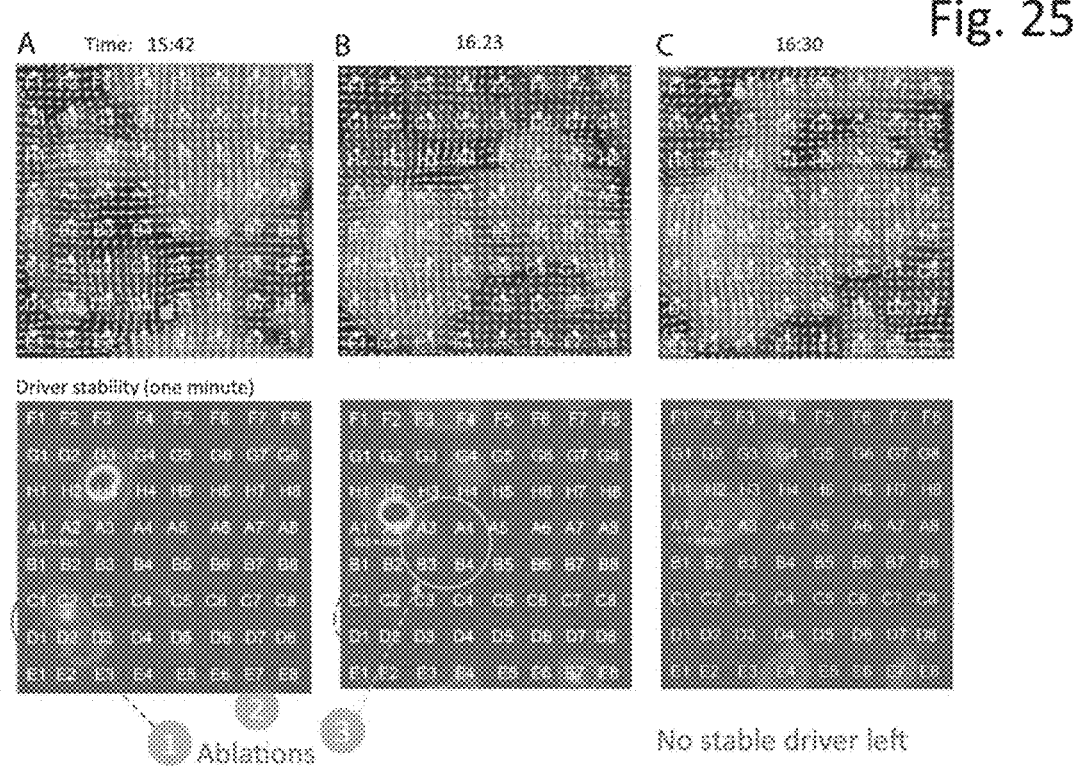

FIG. 25 shows an example of results obtained using long term EGF monitoring applied during RF ablation, where sources of excitation were successfully removed.

Figure 26:
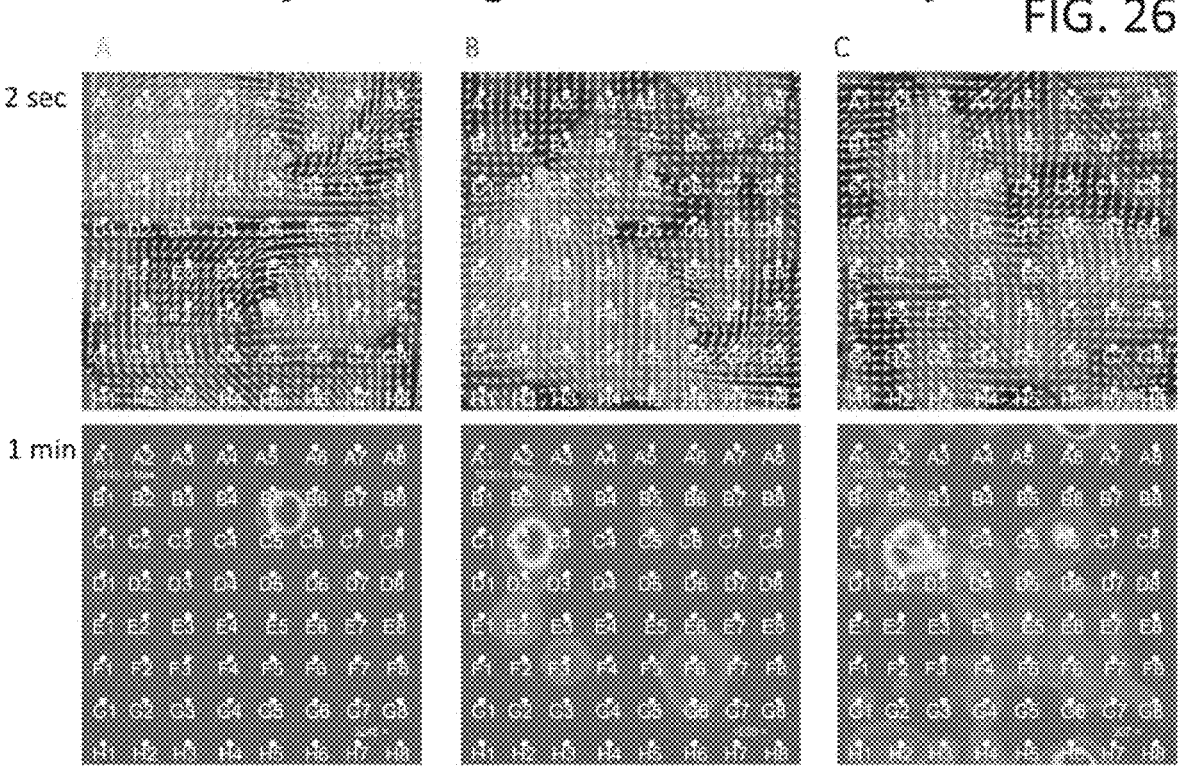

FIG. 26 shows examples of patient classification according to A, B and C categories (as described above) using "Leading Source EGF Stability techniques.

FIG. 27 shows an example of prognostic relevance (body surface), where nearly half of treated patients had a recurrence of AF. Retrospective EGF mapping using ABLAMAP techniques revealed that a few patients had A-types sources (drivers), more patients had on/off B-type sources (triggers), and a few patients had chaotic C-type sources.

FIG. 28 shows a comparison between FIRM results obtained using the Abbott TOPERA system and the ABLAMAP EGF system, where the same data from the same patient are used to obtain results from the two different systems using different techniques. As will be seen, the resolution provided by the ABLAMAP EGF system is much more detailed, specific and useful than that provided by the TOPERA system. In the ABLAMAP results, two sources are identified at E3 and A4, which together combine to cause the rotation shown in the comparatively lower-resolution TOPERA-generated image.

Figure 29:
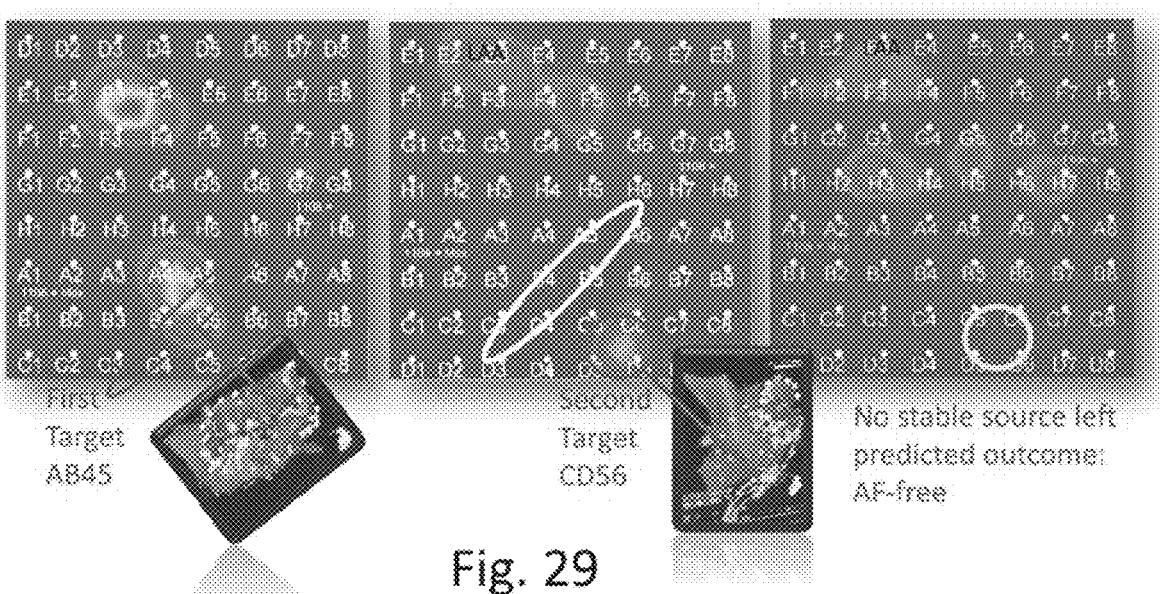
Figure 30:
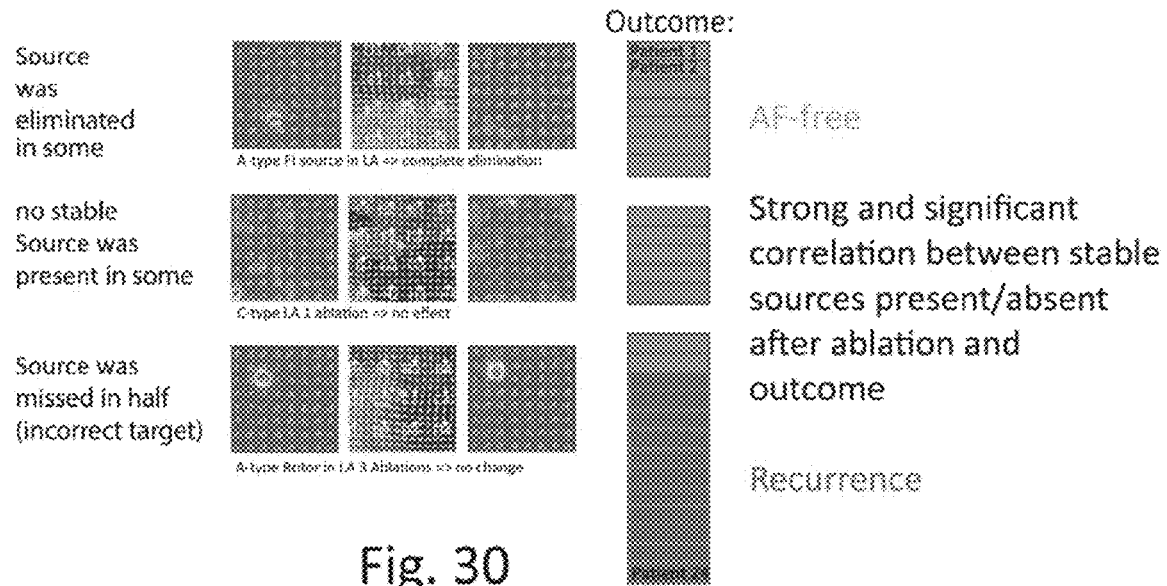

FIG. 29 shows an example of therapy guidance using one embodiment of ABLAMAP EGF systems and methods. A B-type patient is identified. A first target at AB45 is identified and removed using RF ablation, as is a second target at CD56. The patient then becomes AF-free when no stable source remains after ablation at the appropriate locations has been carried out. The importance of the improved accuracy and comparatively high-resolution results provided by ABLAMAP EGF systems and methods is emphasized by referring to FIG. 30, which summarizes outcomes obtained using the TOPERA/ABBOTT FIRM system, where the data acquired from patients were processed using ABLAMAP EGF methods. ABLAMAP EGF processing revealed that in some patients sources were eliminated, in other patients no stable source was present, and in most patients the sources were missed and an incorrect target was identified.

Electrographic Volatility Index

There are now described and disclosed various aspects, factors and details relating to a new metric we have developed called the "Electrographic Volatility Index" (or EVI). According to one embodiment, which is not intended to be limiting as to the number of parameters or mechanisms EVI may take into account in generating an EVI score or metric, or whether or not classification "types" of the kind disclosed and described herein (i.e., A, B, C, D and E types) are employed in generating EVI metrics or scores, and with reference to FIGS. 31 and 34 (described in further detail below), EVI can be based on three different mechanisms relating to AF:

1. Activity of sources (focal impulse and rotational sources, A- and B-type) and active sources (A- and B-type): Sources that drive or trigger AF;

2. Flow angle variability (FAV) of electrographic flow (EGF) patterns (D-type)—Stable Circuits (D-type): Stable reentry patterns, or stable flow fields or "passive" rotational phenomena;

3. Active fractionations (co-localization of fractionation and action potential origins, E-type): Highly fractionated areas that emanate action potentials.

A, B and C types are described in detail above. Types D and E are described in detail below. Note that such "types," when employed to segregate data when generating EVI are merely derived from metrics such as activity. EVI is thus a formula that takes activity and other metrics into account, and from such metrics EVI directly computes something useful. It should therefore be understood that in some embodiments the use of "types" in how the generation of EVI scores and metrics are computed is merely a means of providing to users a simple-to-understand mechanism of how EVI operates, but also that the use of such "types" is not required or necessary to generate EVI scores or metrics.

The "Electrographic Volatility Index" or EVI is a metric or score that can be calculated, which, according to one embodiment that is not intended to be limiting, may be represented as:

$$EVI = (1-p \ (\text{source activity}))^{\alpha} \cdot p \ (\text{flow angle variability})^{\beta} \cdot (1-p \ (\text{active fractionation}))^{\gamma},$$

where the symbol "·" denotes convolution, and where $\alpha$, $\beta$ and $\gamma$ are weighting or scaling numbers. In general, the concept of EVI is to create a statistical model that computes a score from the abovementioned (or additional) metrics. A statistical model can be this formula, which is parameterized by alpha, beta and gamma. These so-called hyper parameters can be tuned to achieve optimal significance of the statistical model. A neural network or any other machine learning model can beneficially be used to compute EVI scores. See, for example, FIGS. 38 and 40, where the results presented therein were generated using neural networks/machine learning. Other embodiments not explicitly disclosed or described herein of calculating an EVI metric or score will become apparent to those skilled in the art after having read and understood the specification, drawings and claims set forth herein, and the formula set forth above, and the use of "types" therein is not intended to be limiting. Furthermore, those skilled in the art will also understand that the use of types per se (i.e., A, B, C, D and/or E types) is not necessarily required to generate usable EVI scores or metrics, as the scores or metrics are based on, for example, detected activity, detected FAV, detected AFR, and so on. Instead, identifying the mechanisms of action at work in a given AF patient's heart by using EGF results to generate EVI scores or metrics that are generated from such results is what generally matters most.

The EVI metric or score may be used to predict the probability of freedom from AF for a given patient, more about which is said below. In one embodiment, we mechanistically discriminate three different probabilities based on the three mechanisms described above: (i) source activity—sources that trigger the transition into AF; (ii) EGF flow variability (Flow Angle Variability or FAV) which breaks AF stability, and terminates AF; and (iii) Fractionation dependent flow origins, which represent independent triggers of so-called Active Fractionation (AFR) areas that are typically not detected as sources, but which exist in in sick atria.

There are multiple mechanisms that can be the cause of atrial fibrillation. While sources are one of them (e.g., A and B types), not all patient conditions can be explained by sources. According to one embodiment, the EVI aims at unifying multiple causes into a score ranging from 0% to 100% where 100% correlates strongly with freedom of AF as an outcome and 0% with recurrences.

As described in detail above, EGF mapping is a novel method of visualizing in vivo, near real-time cardiac action potential flow, providing actionable information for targeting and eliminating active sources that drive AF. Using EGF mapping algorithms, we can calculate the different probabilities of achieving freedom from AF based on the contributions of three distinct electrographically determined mechanisms of AF and combine them into an AF risk prediction score, called the EVI.

EVI goes beyond the identification of AF sources, and is capable of identifying the underlying mechanistic patterns of AF disease. During a procedure, a patient's future outcome is not pre-determined, but rather can be optimized by using real-time actionable information about mechanistic AF disease patterns to customize a targeted ablation strategy for an individual patient. Using electrographic flow (EGF) mapping algorithms, we can mechanistically discriminate three different probabilities based on the three distinct mechanisms described above.

To validate the ability of EVI to predict the likelihood of freedom from AF based on invasively measured electrophysiologic and substrate data from both atria, we analyzed a cohort of many patients that underwent FIRM mapping and ablation. We retrospectively derived the EVI on a corresponding development cohort of many patients who underwent FIRM-guided ablation and from whom a final 1-minute recording of unipolar electrograms from a 64-electrode basket catheter was obtained after the last ablation lesion. Those patients were then prospectively validated in a test cohort of many patients who underwent FIRM-guided ablation and had a final 1-minute recording of unipolar electrograms from a 64-electrode basket catheter after the last ablation lesion.

The demographics of the development and validation cohorts were similar. Using EGF mapping to quantify source activity (SAC), flow angle stability (FAV), and active fractionation (FRC), which each correspond to different AF mechanisms as described above, we found that by combining the different probabilities of freedom from AF 12 months post-ablation associated with each electrographic flow parameter for the patients in the development cohort, we could calculate the EVI, which strongly correlated with an individual patient's likelihood of freedom from AF at 12 months post-procedure ($R^2=0.998$). We then prospectively applied the EVI to a corresponding validation cohort of many patients and found an equally strong correlation ($R^2=99.46$).

Based on multi-electrode catheter recordings of unipolar electrograms analyzed using EGF mapping, a multivariate composite scoring system accounting for electrophysiologic properties of the atria as well as the underlying atrial substrate was derived retrospectively and applied prospectively. EVI predicted freedom from AF after ablation in both development and validation cohorts. EVI was discovered to provide a real-world picture of an individual patient's atrial fibrillatory status both prior to and after ablation.

In one embodiment, an EVI matrix may be configured as follows:

1. Leading Source Activity/p(source)

When the source is 100% active, the probability of recurrence is high and the likelihood of Freedom from AF is very low.

When source activity is below 20% (Basal Activity: BaseAct) freedom from AF is uncertain and depends on Flow Angle Variability (FAV) and Active Fractionations (AFRs).

$$p(\text{source})=1-(\text{Activity}-\text{BaseAct})/(1-\text{BaseAct})$$

2. Flow Angle Variability/p(variability)

When Flow Angle Variability (FAV) is very low, AF once triggered is generally stable and p(variability) for freedom from AF is very low.

When FAV is at FAVmax, freedom from AF is uncertain and depends on Activity and Active Fractionations (AFRs).

$$p(\text{variability})=\text{FAV}/\text{FAVmax}$$

3. Active Fractionation/p(active_fractionation)

When Active Fractionation is at FracMax, the probability of recurrence is high and p(active_fractionation) for freedom from AF is very low.

When Active Fractionation is zero, AF is uncertain and depends on Act and FAV.

$$p(\text{active\_fractionation})=1-\text{Active Fractionation}/\text{FracMax}$$

Figure 32:
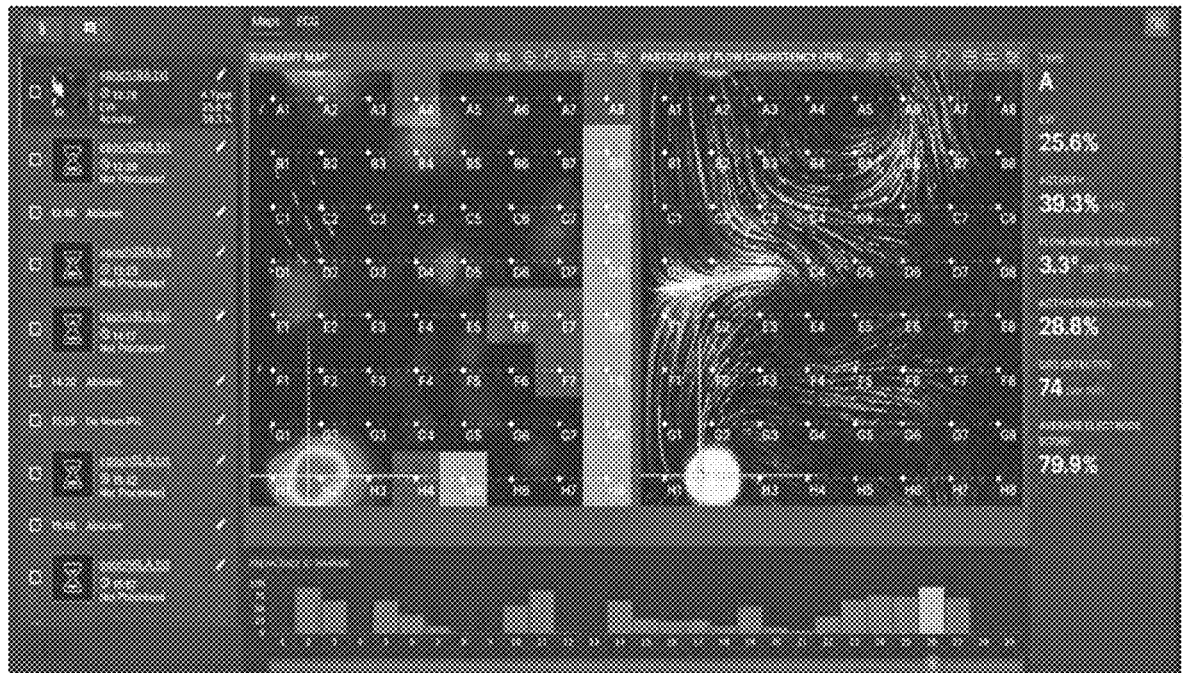
FIG. 32 shows one embodiment of an Electrographic Flow (EGF) and EVI display provided to a user by a computing device or computer 300.

FIG. 32 shows one non-limiting example or embodiment of a display on screen or monitor 324, which is provided to a user by a computing device or computer 300. Computer 300 and display 324 can form a portion of cardiac electrophysiological mapping (EP), pacing and ablation system 100 or a portion thereof. (See, for example, FIGS. 1(a), 1(b), 15, 16, and 20, and corresponding portions of the specification above as regards details concerning the operation and use of system 100, and the configuration thereof, as they may be applied in the context of computing and applying EVI scores or metrics.) Metrics shown in the example display of FIG. 33 include patient type estimation, EVI, Flow Angle Stability (FAS), Active Fractionation (AFR), and the number of QRS peaks detected per minute. Patient classification into A/B/C/D/E types is a method to simplify, summarize and quantify the typical characteristics of EP recordings that have been taken in a patient's atria. (Note, however, that in some cases the resulting classifications might not reflect what one might expect from a given type or patient. In the example display of FIG. 32, we show all values that go into the classification formula so the user can reconstruct which metric might have influenced a classification that could be erroneous.) According to one example embodiment not intended to be limiting, a method for the computation of patient classification may be represented by pseudo-code as follows:

```
c_type_evi_lower_bound=0.75
b_type_activity_lower_bound=0.27
a_type_activity_lower_bound=0.33
de_type_act_frac_lower_bound=0.36
de_type_fatv_upper_bound=0.0234
e_type_act_frac_lower_bound=0.4
d_type_fatv_upper_bound=0.02
if activity>a_type_activity_lower_bound:
    return PatientType.A
if activity>b_type_activity_lb:
    return PatientType.B
if  active_fractionation>de_type_act_frac_lower_bound
    and \
    fatv<de_type_fatv_upper_bound:
if active_fractionation>e_type_act_frac_lower_bound:
    return PatientType.E
if fatv<d_type_fatv_upper_bound:
    return PatientType.D
else:
    return PatientType.E
return PatientType.C
```

According to one example embodiment not intended to be limiting, a method for the computation of EVI may be represented by pseudo-code as follows:

```
activity_base=0.08
fatv_f2f_max=0.035
active_fractionation_max=0.8
alpha=3.65346372724238
beta=1.92044250052391
gamma=0.406325079335849
rescaling=1.99402775126509
offset=0.0757199300318663
p_source=(activity-self.activity_base)/(1-self.activity_
    base)
p_variability=fatv/self.fatv_f2f_max
p_active_fractionation=(
    act_frac
    /
    self.active_fractionation_max
)
multipliers, powers=zip(
    (1-p_source, self.alpha),
    (p_variability, self.beta),
    (1-p_active_fractionation, self.gamma)
)
res=np.float_power(np.clip(multipliers,  0,  np.inf),
    powers).prod ( )
return float(np.clip(self.rescaling*(res+self.offset), 0, 1))
```

Flow Angle Variability

Areas where the EGF is consistently going in the same direction over the course of a recording can be useful ablation targets. Flow angle variability measures the amount by which flow vectors change their direction at a given location. Low values correspond to stable flow, high values correspond to more chaotic, variable flow directions.

In one embodiment, for each (time-wise) subsequent pair of frames, we estimate a flow field. For each subsequent pair of flow fields, we compute the difference in degrees by which the vectors change their direction, typically taking the shortest angular distance. In one embodiment, therefore, one such flow angle variability map has the same dimensions as a single flow map, and has values between 0° and 180°.

In one embodiment, we now average all these flow angle variability maps over the entire recording, time-wise. The result is a map with the same dimensions as a single flow map, again with values between 0° and 180°, representing the average number of degrees that vectors at a given location change from frame to frame. Since in one embodiment the time delta between frames after subsampling is 19 ms, we report values for the mean flow angle variability in the following units: °/(19 ms). The metric shown in the right column in the recording view of FIG. 32 is the average of this. In one embodiment, in a summary map we use the flow angle variability to show static white arrows in the area of the most stable flow (lowest flow angle variability).

These metrics are computed after EGF estimation. If the EGF estimate is wrong, the resulting metrics will consequently be inaccurate. The main reason for inconsistent flow is bad electrode contact, which can be indicated to a user with an Electrode Score (see FIG. 32).

It is known that complex fractionated atrial electrograms (CFAEs) may represent important sites for AF perpetuation: See, for example, Konings et al., "Configuration of unipolar atrial electrograms during electrically induced atrial fibrillation in humans," Circulation 1997; 95:1231-41. Also, Kalifa et al. performed a computational study that showed that fractionation resulted from wave collisions from focal high frequency AF drivers in proximity to such fractionated potentials. See Kalifa et al., "Mechanisms of wave fractionation at boundaries of high frequency excitation in the posterior left atrium of the isolated sheep heart during atrial fibrillation," Circulation 2006; 113:626-33. See also, for example, Sohal et al., "Is Mapping of Complex Fractionated Electrograms Obsolete," Arrhythm. Electrophysiol. Rev. 2015 August; 4(2): 109-115; Atienza et al., "Mechanisms of Fractionated Electrograms Formation in the Posterior Left Atrium During Paroxysmal Atrial Fibrillation in Humans," J Am Coll Cardiol. 2011 Mar. 1; 57(9): 1081-1092; and Correa de Sa et al., "Electrogram Fractionation—The Relationship between Spatiotemporal Variation of Tissue Excitation and Electrode Spatial Resolution," Circ. Arrhythm. Electrophysiol. 2011 December; 4(6): 909-16. The foregoing Kalifa et al., Sohal et al., Atienza et al., and Correa de Sa et al. publications are cited in an IDS filed in the present patent application on even date herewith, and each such publication is hereby incorporated by reference herein, each in its respective entirety.

It has been discovered that deriving the amount of fractionation in a signal from the ratio of the signal that is not attributed to flow conduction or far field is important. See the following mathematical descriptions. Here, and according to one non-limiting embodiment, we define fractionation as follows:

$$F = \frac{E_{frac}}{E_{signal}},$$

where $E_{frac}=E_{signal}-E_{conduction}$ in areas dominated by conduction.

$E_{frac}=E_{signal}-E_{instantaneous}$ in areas dominated by the far field.

$$E_{signal} = \sum_{t=1}^{\#samples} (s[t])^2$$

In one embodiment, the instantaneous component between signals picked up by two neighbouring electrodes is computed as correlation between those signals:

$$E_{instantaneous}(s1, s2) = \sum_{t=1}^{\#samples} s1[t]s2[t]$$

In one embodiment, the instantaneous component of an electrode is an average of $E_{instantaneous}$ between the signals picked up by the electrode and its neighbours respectively.

Figure 33:
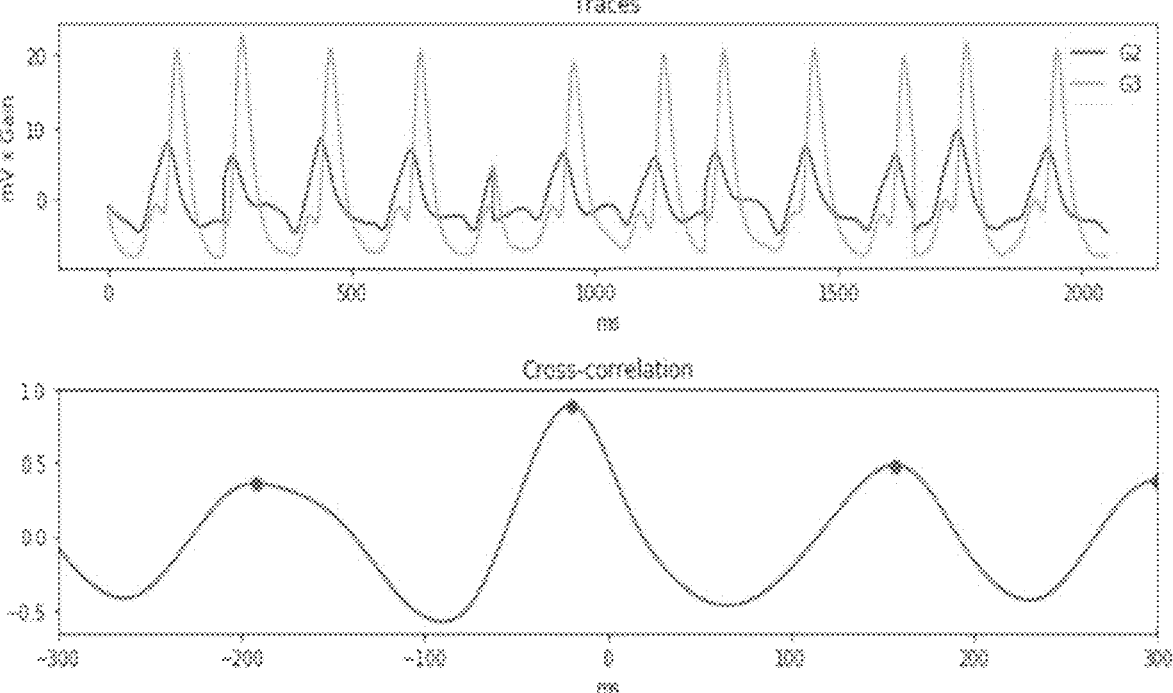
FIG. 33 shows example electrogram signals obtained from intra-cardiac electrodes G2 and G3, and their corresponding cross-correlation.

In one embodiment, the conduction component between two signals is determined by the biggest peak in cross-correlation between these two signals (see FIG. 33).

$$E_{conduction}(s1, s2) = \frac{max_{\Delta t}\left(\sum_{t=1}^{\#samples} s1[t]s2[t + \Delta t]\right)}{\sqrt{\sum_{t=1}^{\#samples}(s1[t])^2}\sqrt{\sum_{t=1}^{\#samples}(s2[t])^2}}$$

In one embodiment, the conduction component is undefined if:

there is another peak in cross-correlation with smaller $\Delta t$ or $\Delta t > 50$ ms or $\Delta t < 5$ ms (correlation is not attributed to conduction from electrode 1 to electrode 2 (too slow or too fast for conduction respectively)).

and $$E_{conduction} = E_{signal}(s1)E_{conduction}(s1, s2),$$

where s2 are neighbors of s1 such that $E_{conduction}(s1,s2)$ is defined as shown above.

Referring to the example of FIG. 33, and according to one embodiment, ECG traces picked up by neighboring electrodes G2 and G3 (in units of amplifier gain×V) and a normalized correlation between them depend on the time offset between the signals. The largest and closest to 0 peak is at $\Delta t = -20$ ms. This indicates conduction from G2 to G3, and in this example it takes 20 ms for action potentials to travel from G2 and G3.

Active Fractionation

In some patients' atria, it is believed that there exist areas with a high degree of fractionation which emanate action potentials. These might not be detected as sources due to the inherently asymmetrical nature of such sources of action potential flow. The active fractionation (AFR) metric aims at quantifying the amount of action potential flow originating from areas of high fractionation. This metric may be computed from two components: fractionation (described above) and streamline origin density (SOD). The SOD is derived by tracing back the flow field until convergence to identify origins of EGF.

For each flow field (e.g., 29 in a 60 second recording), we follow all arrows against their directions. When this tracing converges, we record this as a streamline origin point. Finally, we report the average fractionation value at the location of these streamline origins. If the streamline origins are mostly at sources without fractionation, this value will be close to 0. In the other case, the result will be up to 100%. Generally, the AFR metric is not used for ablation guidance at this point. The fractionation amount can always be verified in the ECG view. In addition, to analyze the flow of action potentials in the atria, it is preferred to separate atrial action potentials (or p waves) from the QRS complex far field.

Referring now to FIG. 34, and as described partially above, there is shown a representation of how EVI scores or metrics can be derived according to one embodiment.

Figure 35:
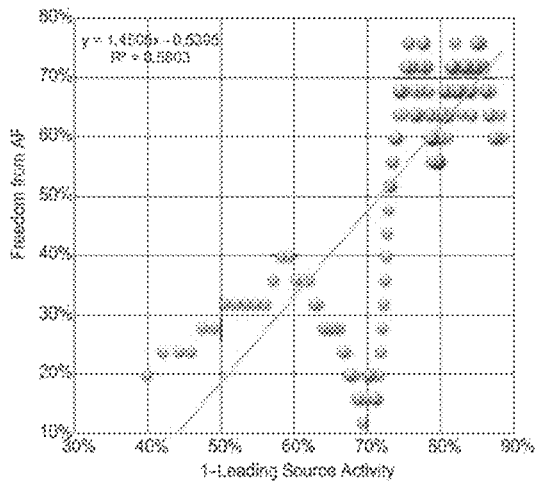
FIG. 35 shows the results of generating probability of freedom from AF statistics from an AF patient population using EGF source activity.

In FIG. 35, there are shown the results of EP data acquired from many patients, which were subsequently processed and analyzed to yield the probability of freedom from AF results displayed therein. FIG. 35 shows that EGF source activity (Types A and B) alone cannot provide a complete picture of a patient's AF Status. In FIG. 35, active PV-type, A-type, and B-type sources were targeted and eliminated in patients prior to EP data being acquired and subjected to EGF and EVI processing, classification, and display. In the displayed probability results of FIG. 35, Activity R2=0.58, and Binary Prediction Correctness=70%.

Figure 36:
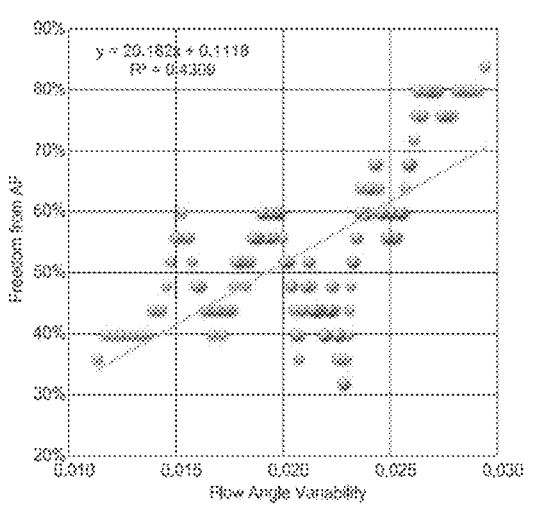
FIG. 36 shows the results of generating probability of freedom from AF statistics from an AF patient population using EGF flow angle variability.
Figure 37:
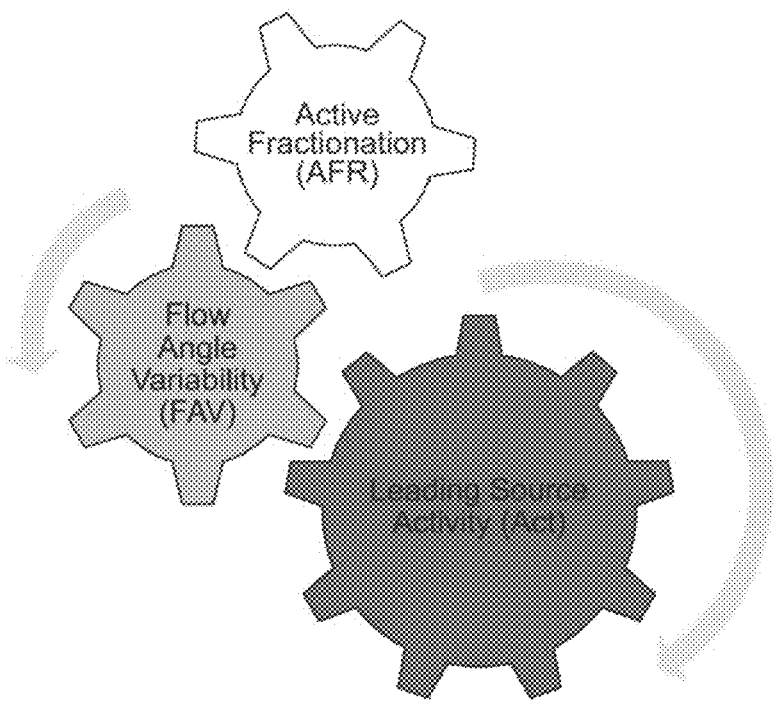
FIG. 37 shows a schematic representation of three mechanisms that can be employed to generate an Electrographic Volatility Index (EVI)

In FIG. 36, there are shown the results of EP data acquired from many patients, which were subsequently processed and analyzed to yield the probability of freedom from AF results displayed therein. FIG. 36 shows that EGF flow angle variability alone cannot predict freedom from AF (Type D). In FIG. 37, D-type sources were targeted and eliminated in patients prior to EP data being acquired and subjected to EGF and EVI processing, classification, and display. In the displayed probability results of FIG. 36, FAV correlation $R^2=0.43$, and Binary Prediction Correctness=63%. FIG. 36 also demonstrates that stable D-type circuits can be simulated and form a circuitry that can be understood and quantitatively analyzed.

FIG. 37 shows a schematic representation of an effective method of analyzing a patient's EP data using EGF and EVI techniques, where leading source activity (ACT) or types A and B, flow angle variability (FAV) or type D, and active fractionation (AFR) or Type E are all employed to arrive at an optimum EVI score or metric for a patient potentially suffering or known to suffer from AF. With continued reference to FIG. 37, and in the context of predicting a probability of freedom from AF, using EGF mapping, and according to one embodiment, we can mechanistically discriminate and calculate the different probabilities of achieving freedom from AF based on the contribution of three mechanisms:

1. EGF-identified AF source activity (Act): Active sources trigger the transition into AF Leading Source Activity/p(source):

When the source is 100% active, the probability of recurrence is high and the likelihood of Freedom from AF is very low.

When the source activity is below 20% (Basal Activity: BaseAct), freedom from AF is uncertain and depends on flow angle variability and active fractionations.

$$p(source)=1-(Activity-BaseAct)/(1-BaseAct)$$

2. EGF variability (Flow Angle Variability, FAV): destabilizes and terminates AF Flow Angle Variability/p(variability):

When Flow Angle Variability (FAV) is very low, AF once triggered is stable and p(variability) for Freedom from AF is very low.

When FAV is at FAVmax, Freedom from AF is uncertain and depends on Activity and Active Fractionations.

$$p(variability)=FAV/FAVmax$$

3. Active fractionation (AFR); action potential flow in areas of high fractionation Active Fractionation/p(active fractionation):

When Active Fractionation is at FracMax probability of recurrence is high and p(active_fractionation) for Freedom from AF is very low.

When Active Fractionation is zero AF is uncertain and depends on Act and FAV

FIG. 38 shows freedom from AF probability results obtained with many patients separated into development and validation cohorts, where all three ACT, FAV and AFR metrics were used to generate EVI scores or metrics. In the development cohort, an optimization for linear relationship between the EVI score and freedom from AF provided results of Slope=0.9, $R^2$=0.88, WeightA=2.4, and WeightB=0.89. In the internal validation cohort, calculated with a formula fitted to the development cohort, the results were a Slope=0.8, and $R^2$=0.88. The same correction coefficients were used as in the development cohort.

FIG. 39 illustrates the effects of adding an active fractionation parameter to EVI analyses. As described above, E-type highly fractionated areas emanate action potentials that can be detected by a combination of fractionation and action potential origins (Active Fractionation). As shown in FIG. 39, no significant source activity in shown in the standard EGF map, but co-localization exists as between the Active Fractionation Score (above 0.8) and high action potential flow origin density. The high active fractionation score means that 80% of the shown high-amplitude signal at location D5 in the EGF map is not correlated with adjoining electrodes. In other words, vexatious type E areas can be reliably quantified and analyzed using the EGF and EVI techniques and methods described herein.

Referring now to FIG. 40, there are shown results obtained with many patients separated into development and validation cohorts. FIG. 40 shows that in the training population, a least square fit of EVI vs. Outcome (% AF-free), with a sliding average over 25 patients, $R^2$=0.9066. In the validation population of FIG. 40, the fit result parameters from the development population or cohort was employed, which provided even better correlation ($R^2$=0.9371, with no overfitting).

Figure 41:
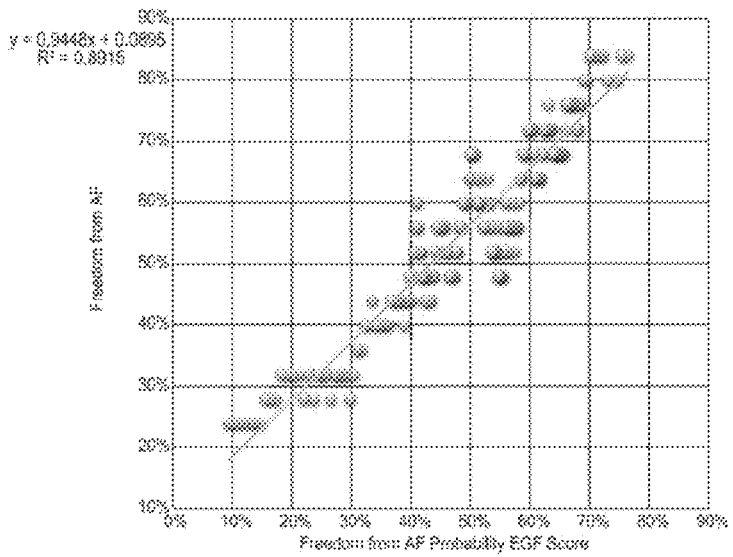
FIG. 41 shows results obtained by generating probability of freedom from AF statistics from combined development and validation cohorts.

FIG. 41 shows results obtained from the same populations of FIG. 40, but where the populations are combined. Here, a least square fit of EVI vs. Outcome (% AF-free), with a sliding average over 25 patients, provides an $R^2$=0.8915.

Figure 42:
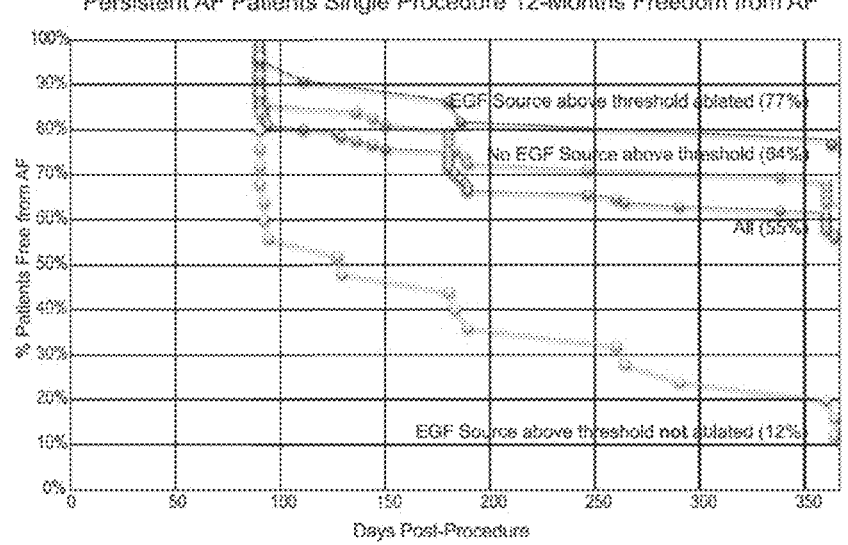
FIG. 42 shows results obtained in a retrospective EVI analysis of AF patients.
Figure 45:
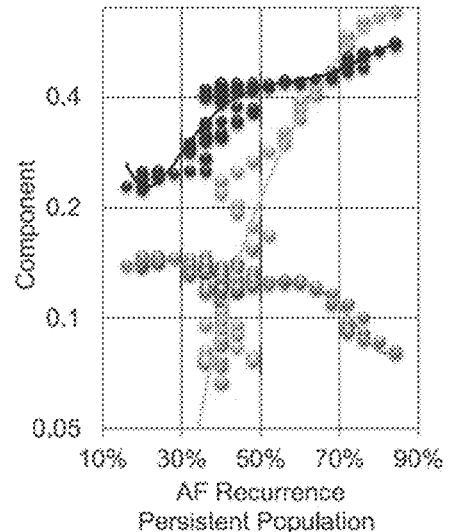
Figure 47:
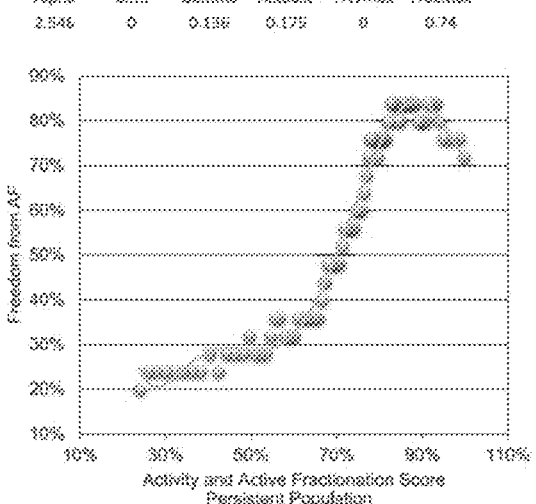

FIG. 42 shows that EGF-identified sources mattered according to a retrospective data analysis performed on a population of persistent AF patients who had undergone a single ablation procedure, and who remained AF-free for 12 months. Ablation of sources above a threshold resulted in incremental improvement in 12-month freedom from AF compared to all corners or those patients without any sources above the threshold. If a source above the threshold was not ablated, the chance or probability of recurrence of AF was very high. The results shown in FIG. 42 are statistically summarized in FIG. 43.

FIGS. 44-48 show EVI score comparisons between re-do AF patients and patients clinically diagnosed with persistent AF. Here, re-do patients are AF patients who underwent a first ablation procedure and had a recurrence of AF, and who therefore received a second ablation treatment. FIG. 49 summarizes the results shown in FIGS. 44-48, where: (1) an EGF/EVI score or metric can successfully classify a wide spectrum of AF patients using its three computational components; (2) De novo persistent AF patients are dominated by the existence of focal or rotational sources (A- and B-type); stable circuits maintaining AF play an inferior role in such patients, and AF fractionation comprises only a small component of the detected activity; and (3) In re-do AF patients, in contrast, active sources are shown to play only a minor role. AF recurrence depends on stable circuits maintaining AF, and on active fractionation.

Using the EGF and EVI techniques described above, an arrhythmia mapping system can be provided that provides in-vivo, real-time visualization of cardiac action potential flow (EGF Mapping), and that is capable of providing actionable information that a physician can use to target and eliminate active AF sources that matter. Diagnostic and prognostic mapping tools can be provided that generate real-time panoramic electrographic data and analytics specific to individual patients, and that are actionable during a patient's procedure. This minimizes empirical and/or unnecessary ablations, thereby reducing potential complications, improving individual patients' outcomes post-ablation, and providing a quantitative and reasonably accurate "picture" of patients' responses to ablation therapy. In addition, the EGF and EVI techniques described and disclosed herein can be used to provide a "picture" of an individual's baseline or chronic disease state, and iterative "pictures" of disease after each intervention in step-wise fashion for longitudinal management of the chronic disease. Data aggregation can be leveraged over time to assess and even compare previous strategies to provide tailored and timely recommendations to inform treatment strategy. Pharmaceutical therapy data for individual patients can also be added to the statistical analyses that are carried out. Speed and efficacy can be improved, costs of procedures can be reduced, and expert decision-making intelligence can be employed to inform complex ablation strategies. EGF and EVI, used in combination, can harness the power of longitudinally-collected, and unifying/comparative real-world procedural, data across operators, hospitals, centers, ablation techniques, energy modalities and lesion sets into a single cloud-based database, which may then be employed to inform clinical decision-making, patient management, and population-based research.

It will now also be seen that EVI can be employed to predict the probability of freedom from AF after a catheter ablation procedure has been carried out. Currently, patients with a variety of clinical presentations undergo a wide range of ablation procedures with varying ablation techniques, ablation energy sources, and combinations of lesion sets. Using electrographic flow (EGF) mapping algorithms, we can mechanistically discriminate three different probabilities based on three mechanisms (1) source activity as sources trigger the transition into AF; (2) EGF flow variability or flow angle variability, which reduces AF stability and terminates AF; and (3) fractionation-dependent flow origins, which represent independent triggers not detected as sources, but influencing the nature of action potential flow in the atria. As shown above, we have validated the ability to predict the likelihood of freedom from AF using a clinical scoring system, where EP mapping data were collected using unipolar basket catheter electrodes. Based on multi-electrode catheter recordings of unipolar electrograms analyzed using EGF mapping, a multivariate composite scoring system accounting for electrophysiologic properties of the atria as well as the underlying atrial substrate was derived retrospectively and applied prospectively. EVI predicted freedom from AF after ablation in both a development cohort and a validation cohort of patients undergoing ablation for AF. EVI is shown to provide a real-world picture of an individual patient's atrial fibrillatory status both prior to and after ablation.

In some embodiments, there are provided systems configured to generate an estimate or probability of a patient being free from atrial fibrillation (AF), the systems comprising at least one computing device comprising at least one non-transitory computer readable medium configured to store instructions executable by at least one processor to determine the source and location of the atrial fibrillation in the patient's heart, the computing device being operably connected to a display or monitor, the computing device being configured to: (a) receive electrogram signals; (b) assign positions of the electrodes on a mapping electrode assembly employed to acquire the electrogram signals to their corresponding electrogram signals; (c) provide or generate a map, representation, or data set of the electrode positions; (d) process the electrogram signals to generate a plurality of electrogram surfaces corresponding at least partially to the map, representation, or data set; (e) process the plurality of electrogram surfaces through time to generate at least one electrographical flow (EGF) map, representation, pattern, or data set; (f) process the at least one EGF map, representation, pattern, or data set to determine at least two of source activity levels, flow angle variability (FAV) levels, and active fractionation (AFR) levels corresponding thereto; (g) determine and generate, on the basis of a combination of the determined at least two of source activity levels, FAV levels, and AFR levels, an electrographical volatility index (EVI) representative of the estimate or probability of the patient being free from AF, wherein at least one of the EVI and the estimate or probability of the patient being free from AF is presented on a display, monitor, or printer to a user.

In some embodiments, the foregoing systems can further comprise any one or more of: (a) the computing device being configured to convolve at least two of the determined source activity levels, the determined flow angle variability levels, and the determined active fractionation levels with one another to provide the estimate or probability of the patient being free from AF; (b) the determined source activity levels corresponding to at least one of Type A atrial behavior exhibiting stable rotors and drivers and Type B atrial behavior where rotors switch on and off; (c) the determined flow angle variability levels corresponding to Type D atrial behavior exhibiting stable reentry patterns with low FAV; (d) the determined active fractionation levels corresponding to Type E atrial behavior exhibiting a combination of active fractionation and action potential flow origins; (e) the activity level corresponding to a percentage of time a detected source is determined to be on or active; (f) when the percentage of time the detected source is on or active is greater than about 25% the activity level is deemed to be high, and the probability the patient is free from AF is lower; (f) when the percentage of time the detected source is on or active is greater than between about 26% and about 30% the activity level is deemed to be high; (g) when the percentage of time the detected source is on or active is less than about 30% the activity level is deemed to be low, and the probability the patient is free from AF is deemed to be higher; (h) when the percentage of time the detected source is on or active is less than between about 26% and about 30% the activity level is deemed to be low, and the probability the patient is free from AF is deemed to be higher, (i) the flow angle variability level corresponding to one or more EGF flow angles computed over a predetermined period of time; (j) a flow angle level exceeding a range between about 4 and 5 degrees measured over about 20 milliseconds is deemed to be high, and the probability the patient is free from AF is deemed to be higher; (k) a flow angle level less than a range between about 4 and 5 degrees measured over about 20 milliseconds is deemed to be low, and the probability the patient is free from AF is deemed to be lower; (l) the active fractionation level corresponds to a combination of measuring divergence in EGF flow patterns indicative of action potential origins and measuring a percentage of a surface area of the patients atrium determined to be fractionated on the basis of divergent EGF flow patterns; (l) when the active fractionation level exceeds a level between about 27 percent and about 31 percent of a surface area of an analyzed portion of the patient's atrium exhibiting divergence in EGF flow patterns over a predetermined period of time, the probability the patient is free from AF is lower; (m) when the active fractionation level falls below a level between about 27 percent and about 31 percent of a surface area of an analyzed portion of the patient's atrium exhibiting divergence in EGF flow patterns over a predetermined period of time, the probability the patient is free from AF is higher; (n) the EVI is generated in accordance with the formula: $EVI=(1-p \text{ (source activity)})^{\alpha} \cdot p \text{ (flow angle variability)}^{\beta} \cdot (1-p \text{ (active fractionation)})^{\gamma}$, where the symbol "$\cdot$" denotes convolution.

In further embodiments, there are provided methods of generating an estimate or probability of a patient being free from atrial fibrillation (AF), the method employing at least one computing device comprising at least one non-transitory computer readable medium configured to store instructions executable by at least one processor to determine the source and location of the atrial fibrillation in the patient's heart, the computing device being operably connected to a display or monitor, the methods comprising: (a) receiving electrogram signals acquired from electrodes located inside the patient's heart; (b) using the computing device, assigning positions of the electrodes on a mapping electrode assembly employed to acquire the electrogram signals to their corresponding electrogram signals; (c) using the computing device, providing or generating a map, representation, or data set of the electrode positions; (d) using the computing device, processing the electrogram signals to generate a plurality of electrogram surfaces corresponding at least partially to the map, representation, or data set; (e) using the computing device, processing the plurality of electrogram surfaces through time to generate at least one electrographical flow (EGF) map, representation, pattern, or data set; (f) using the computing device, processing the at least one EGF map, representation, pattern, or data set to determine at least two of source activity levels, flow angle variability (FAV) levels, and active fractionation (AFR) levels corresponding thereto; (g) using the computing device, determining and generating, on the basis of a combination of the determined at least two of source activity levels, FAV levels, and AFR levels, an electrographical volatility index (EVI) representative of the estimate or probability of the patient being free from AF, and (h) presenting at least one of the EVI and the estimate or probability of the patient being free from AF on a display, monitor, or printer to a user.

In some embodiments, such foregoing methods can further comprise any one or more of: (a) the computing device convolving at least two of the determined source activity levels, the determined flow angle variability levels, and the determined active fractionation levels with one another to provide the estimate or probability of the patient being free from AF; (b) the determined source activity levels corresponding to at least one of Type A atrial behavior exhibiting stable rotors and drivers and Type B atrial behavior where rotors switch on and off; (c) the determined flow angle variability levels corresponding to Type D atrial behavior exhibiting stable reentry patterns with low FAV; (d) the determined active fractionation levels corresponding to Type E atrial behavior exhibiting a combination of active fractionation and action potential flow origins; (e) the activity level corresponding to a percentage of time a detected source is determined to be on or active; (f) when the percentage of time the detected source is on or active is greater than about 25% the activity level is deemed to be high, and the probability the patient is free from AF is lower; (g) when the percentage of time the detected source is on or active is greater than between about 26% and about 30% the activity level is deemed to be high; (h) when the percentage of time the detected source is on or active is less than about 30% the activity level is deemed to be low, and the probability the patient is free from AF is deemed to be higher; (i) when the percentage of time the detected source is on or active is less than between about 26% and about 30% the activity level is deemed to be low, and the probability the patient is free from AF is deemed to be higher; (j) the flow angle variability level corresponds to one or more EGF flow angles computed over a predetermined period of time; (k) a flow angle level exceeding a range between about 4 and 5 degrees measured over about 20 milliseconds is deemed to be high, and the probability the patient is free from AF is deemed to be higher; (l) a flow angle level less than a range between about 4 and 5 degrees measured over about 20 milliseconds is deemed to be low, and the probability the patient is free from AF is deemed to be lower; (m) the active fractionation level corresponds to a combination of measuring divergence in EGF flow patterns indicative of action potential origins and measuring a percentage of a surface area of the patient's atrium determined to be fractionated on the basis of divergent EGF flow patterns; (n) when the active fractionation level exceeds a level between about 27 percent and about 31 percent of a surface area of an analyzed portion of the patient's atrium exhibiting divergence in EGF flow patterns over a predetermined period of time, the probability the patient is free from AF is lower; (o) when the active fractionation level falls below a level between about 27 percent and about 31 percent of a surface area of an analyzed portion of the patient's atrium exhibiting divergence in EGF flow patterns over a predetermined period of time, the probability the patient is free from AF is higher; and (p) generating the EVI is determined in accordance with the formula: EVI=(1−p (source activity))$^{\alpha}$·p (flow angle variability)$^{\beta}$·(1−p (active fractionation))$^{\gamma}$, where the symbol "·" denotes convolution.

Further embodiments will become apparent to those skilled in the art after having read and understood the claims, specification and drawings hereof.

The various systems, devices, components and methods described and disclosed herein may also be adapted and configured for use in electrophysiological mapping applications other than those involving the interior of a patient's heart. These alternative applications include EP mapping and diagnosis of a patient's epicardium, a patient's spinal cord or other nerves, or a patient's brain or portions thereof, more about which is said below.

It will now be seen that the various systems, devices, components and methods disclosed and described herein are capable of detecting with considerable accuracy and precision the locations and types of sources of cardiac rhythm disorders in a patient's heart, diagnosing same, and making better informed and more accurate and likely-to-succeed treatment decisions for patients.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing description and disclosure outline features of several embodiments so that those skilled in the art may better understand the detailed description set forth herein. Those skilled in the art will now understand that many different permutations, combinations and variations of hearing aid 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

We claim:

1. A system configured to generate an estimate or probability of a patient being free from atrial fibrillation (AF) so that an appropriate ablation therapy can be delivered to the patient, comprising:

at least one computing device comprising at least one non-transitory computer readable medium configured to store instructions executable by at least one processor to determine the source and location of the atrial fibrillation in the patient's heart, the computing device being operably connected to a display or monitor, the computing device being configured to:

(a) receive electrogram signals;

(b) assign positions of electrodes on a mapping electrode assembly employed to acquire the electrogram signals to their corresponding electrogram signals;

(c) provide or generate a map, representation, or data set of the electrode positions;

(d) process the electrogram signals to generate a plurality of at least one interpolated, fitted, smoothed and estimated electrogram surfaces for discrete times of the electrogram signals corresponding at least partially to the map, representation, or data set;

(e) process the plurality of electrogram surfaces through time using optical flow analysis and estimation techniques to generate at least one electrographical flow (EGF) map, representation, pattern, or data set;

(f) process the at least one EGF map, representation, pattern, or data set to determine at least two of source activity levels, flow angle variability (FAV) levels, and active fractionation (AFR) levels corresponding thereto;

(g) determine and generate, on the basis of a combination of the determined at least two of source activity levels, FAV levels, and AFR levels, an electrographical volatility index (EVI) representative of the estimate or probability of the patient being free from AF, wherein at least one of the EVI and the estimate or probability of the patient being free from AF is presented on a display, monitor, or printer to one or more users, and further wherein on the basis of the estimate or probability the one or more users can determine whether to deliver an ablation therapy to the patient.

2. The system of claim 1, wherein the computing device convolves at least two of the determined source activity levels, the determined flow angle variability levels, and the determined active fractionation levels with one another to provide the estimate or probability of the patient being free from AF.

3. The system of claim 1, wherein the determined source activity levels correspond to at least one of Type A atrial behavior exhibiting stable rotors and drivers and Type B atrial behavior where rotors switch on and off.

4. The system of claim 1, wherein the determined flow angle variability levels correspond to Type D atrial behavior exhibiting stable reentry patterns with low FAV.

5. The system of claim 1, wherein the determined active fractionation levels correspond to Type E atrial behavior exhibiting a combination of active fractionation and action potential flow origins.

6. The system of claim 1, wherein the activity level corresponds to a percentage of time a detected source is determined to be on or active.

7. The system of claim 6, wherein when the percentage of time the detected source is on or active is greater than about 25% the activity level is deemed to be high, and the probability the patient is free from AF is lower.

8. The system of claim 6, wherein the percentage of time the detected source is on or active is greater than between about 26% and about 30% the activity level is deemed to be high.

9. The system of claim 6, wherein when the percentage of time the detected source is on or active is less than about 30% the activity level is deemed to be low, and the probability the patient is free from AF is deemed to be higher.

10. The system of claim 6, wherein when the percentage of time the detected source is on or active is less than between about 26% and about 30% the activity level is deemed to be low, and the probability the patient is free from AF is deemed to be higher.

11. The system of claim 1, wherein the flow angle variability level corresponds to one or more EGF flow angles computed over a predetermined period of time.

12. The system of claim 11, wherein a flow angle level exceeding a range between about 4 and 5 degrees measured over about 20 milliseconds is deemed to be high, and the probability the patient is free from AF is deemed to be higher.

13. The system of claim 11, wherein a flow angle level less than a range between about 4 and 5 degrees measured over about 20 milliseconds is deemed to be low, and the probability the patient is free from AF is deemed to be lower.

14. The system of claim 1, wherein the active fractionation level corresponds to a combination of measuring divergence in EGF flow patterns indicative of action potential origins and measuring a percentage of a surface area of the patient's atrium determined to be fractionated on the basis of divergent EGF flow patterns.

15. The system of claim 14, wherein when the active fractionation level exceeds a level between about 27 percent and about 31 percent of a surface area of an analyzed portion of the patient's atrium exhibiting divergence in EGF flow patterns over a predetermined period of time, the probability the patient is free from AF is lower.

16. The system of claim 14, wherein when the active fractionation level falls below a level between about 27 percent and about 31 percent of a surface area of an analyzed portion of the patient's atrium exhibiting divergence in EGF flow patterns over a predetermined period of time, the probability the patient is free from AF is higher.

17. The system of claim 1, wherein the EVI is generated in accordance with the formula: $EVI=(1-p$ (source activity)) $\alpha \cdot p$ (flow angle variability)$\beta \cdot (1-p$ (active fractionation))$\gamma$, where the symbol "·" denotes convolution.

18. A method of generating an estimate or probability of a patient being free from atrial fibrillation (AF) so that an appropriate ablation therapy can be delivered to the patient, the method employing at least one computing device comprising at least one non-transitory computer readable medium configured to store instructions executable by at least one processor to determine the source and location of the atrial fibrillation in the patient's heart, the computing device being operably connected to a display or monitor, the method comprising:

(a) receiving electrogram signals acquired from electrodes located inside the patient's heart;

(b) using the computing device, assigning positions of the electrodes on a mapping electrode assembly employed to acquire the electrogram signals to their corresponding electrogram signals;

(c) using the computing device, providing or generating a map, representation, or data set of the electrode positions;

(d) using the computing device, processing the electrogram signals to generate a plurality of at least one of interpolated, fitted, smoothed and estimated three-dimensional electrogram surfaces for discrete times of the electrogram signals corresponding at least partially to the map, representation, or data set;

(e) using the computing device, processing the plurality of three-dimensional electrogram surfaces through time using optical flow analysis and estimation techniques to generate at least one electrographical flow (EGF) map, representation, pattern, or data set;

(f) using the computing device, processing the at least one EGF map, representation, pattern, or data set to determine at least two of source activity levels, flow angle variability (FAV) levels, and active fractionation (AFR) levels corresponding thereto;

(g) using the computing device, determining and generating, on the basis of a combination of the determined at least two of source activity levels, FAV levels, and AFR levels, an electrographical volatility index (EVI) representative of the estimate or probability of the patient being free from AF;

(h) presenting at least one of the EVI and the estimate or probability of the patient being free from AF on a display, monitor, or printer to one or more users, and (i) on the basis of the estimate or probability the one or more users determine whether to deliver an ablation therapy to the patient.

19. The method of claim 18, further comprising the computing device convolving at least two of the determined source activity levels, the determined flow angle variability levels, and the determined active fractionation levels with one another to provide the estimate or probability of the patient being free from AF.

20. The method of claim 18, wherein the determined source activity levels correspond to at least one of Type A atrial behavior exhibiting stable rotors and drivers and Type B atrial behavior where rotors switch on and off.

21. The method of claim 18, wherein the determined flow angle variability levels correspond to Type D atrial behavior exhibiting stable reentry patterns with low FAV.

22. The method of claim 18, wherein the determined active fractionation levels correspond to Type E atrial behavior exhibiting a combination of active fractionation and action potential flow origins.

23. The method of claim 18, wherein the activity level corresponds to a percentage of time a detected source is determined to be on or active.

24. The method of claim 23, wherein when the percentage of time the detected source is on or active is greater than about 25% the activity level is deemed to be high, and the probability the patient is free from AF is lower.

25. The method of claim 23, wherein when the percentage of time the detected source is on or active is greater than between about 26% and about 30% the activity level is deemed to be high.

26. The method of claim 23, wherein when the percentage of time the detected source is on or active is less than about 30% the activity level is deemed to be low, and the probability the patient is free from AF is deemed to be higher.

27. The method of claim 23, wherein when the percentage of time the detected source is on or active is less than between about 26% and about 30% the activity level is deemed to be low, and the probability the patient is free from AF is deemed to be higher.

28. The method of claim 18, wherein the flow angle variability level corresponds to one or more EGF flow angles computed over a predetermined period of time.

29. The method of claim 28, wherein a flow angle level exceeding a range between about 4 and 5 degrees measured over about 20 milliseconds is deemed to be high, and the probability the patient is free from AF is deemed to be higher.

30. The method of claim 28, wherein a flow angle level less than a range between about 4 and 5 degrees measured over about 20 milliseconds is deemed to be low, and the probability the patient is free from AF is deemed to be lower.

31. The method of claim 18, wherein the active fractionation level corresponds to a combination of measuring divergence in EGF flow patterns indicative of action potential origins and measuring a percentage of a surface area of the patient's atrium determined to be fractionated on the basis of divergent EGF flow patterns.

32. The method of claim 31, wherein when the active fractionation level exceeds a level between about 27 percent and about 31 percent of a surface area of an analyzed portion of the patient's atrium exhibiting divergence in EGF flow patterns over a predetermined period of time, the probability the patient is free from AF is lower.

33. The method of claim 31, wherein when the active fractionation level falls below a level between about 27 percent and about 31 percent of a surface area of an analyzed portion of the patient's atrium exhibiting divergence in EGF flow patterns over a predetermined period of time, the probability the patient is free from AF is higher.

34. The method of claim 18, further comprising generating the EVI is determined in accordance with the formula: EVI=(1−p (source activity))α·p (flow angle variability)β· (1−p (active fractionation))γ, where the symbol "·" denotes convolution.

\* \* \* \* \*